(12) United States Patent
Hedrick et al.

(10) Patent No.: US 8,470,891 B2
(45) Date of Patent: Jun. 25, 2013

(54) BIODEGRADABLE BLOCK POLYMERS FOR DRUG DELIVERY, AND METHODS RELATED THERETO

(75) Inventors: James Lupton Hedrick, Pleasanton, CA (US); Alshakim Nelson, Fremont, CA (US); Chuan Yang, Singapore (SG); Yi Yan Yang, Singapore (SG)

(73) Assignees: International Business Machines Corporation, Armonk, NY (US); Agency for Science, Technology and Research, Singapore (SG)

( * ) Notice: Subject to any disclaimer, the term of this patent is extended or adjusted under 35 U.S.C. 154(b) by 722 days.

(21) Appl. No.: 12/646,024

(22) Filed: Dec. 23, 2009

(65) Prior Publication Data

US 2011/0152167 A1    Jun. 23, 2011

(51) Int. Cl.
| | | |
|---|---|---|
| A61K 47/34 | (2006.01) |
| A61K 9/127 | (2006.01) |
| A61K 48/00 | (2006.01) |
| A61K 38/00 | (2006.01) |

(52) U.S. Cl.
    USPC ......... 514/772.1; 424/450; 514/1.1; 514/44 R

(58) Field of Classification Search
    USPC ....................................... 514/772.1; 424/450
    See application file for complete search history.

(56) References Cited

U.S. PATENT DOCUMENTS

| | | |
|---|---|---|
| 6,413,539 B1 | 7/2002 | Shalaby |
| 6,521,736 B2 | 2/2003 | Watterson et al. |
| 6,699,724 B1 | 3/2004 | West et al. |
| 2008/0281044 A1 | 11/2008 | Monahan et al. |
| 2009/0208553 A1 | 8/2009 | Kemp et al. |
| 2009/0247666 A1 | 10/2009 | Yu et al. |
| 2010/0015433 A1 | 1/2010 | Arfsten et al. |

FOREIGN PATENT DOCUMENTS

| | | |
|---|---|---|
| WO | 2007106997 A1 | 9/2007 |

OTHER PUBLICATIONS

Bae, Y.H., J. Control. Release, Jan. 5, 2009, 133(1), p. 2-3.*
Majer et al., J. Org. Chem., 1994, 59, p. 1937-1938.*
Buchel, K.H., Pestic. Sci., 1972, 3, p. 89-110.*
Hu et al., Biomacromolecules, 2008, 9, p. 553-560.*
Australian Patent Office, International Preliminary Report on Patentability, dated Feb. 23, 2011, PCT/SG2010/000485, Filed Dec. 9, 2011.
PCT/SG2010/000485, PCT Demand filed with Australian Patent Office, dated Oct. 21, 2011.
Biela, et al., "One-Pot Synthesis of Star-Shaped Aliphatic Polyesters with Hyperbranched Cores and Their Characterization with Size Exclusion Chromatography," J.Polymer Science PartA Polymer Chemistry, vol. 44, 4214-4221 (2006).
Bourissou, et al., "Recent advances in the controlled preparation of poly(a-hydroxy acids): Metal-free catalysts and new monomers," Comptes Rendus Chimie, vol. 10 (2007), 775-794.
Coulembier, et al., "From controlled ring-opening polymerization to biodegradable aliphatic polyester: Especially poly(b-malic acid) derivatives," Prog. Polym. Sci., vol. 31 (2006), 723-747.
Dove, "Controlled ring-opening polymerisation of cyclic esters: polymer blocks in self-assembled nanostructures," Chem. Commun., 2008, 6446-6470.
Jerome, et al., "Recent advances in the synthesis of aliphatic polyesters by ring-opening polymerization," Adv. Drug Delivery Reviews, vol. 60 (2008), 1056-1076.
Kamber, et al., "Organocatalytic Ring-Opening Polymerization", Chem. Rev., 2007, 107, 5813-5840.
Kamber, et al., "N-Heterocyclic Carbenes for the Organocatalytic Ring-Opening Polymerization of #-Caprolactone," Macromolecules, 2009, 42(5), 1634-1639).
Pounder, et al., "Metal free thiol—maleimide 'Click' reaction as a mild functionalisation strategy for degradable polymers", Chem. Commun., 2008, 5158-5160.
Radowski, et al., "Supramolecular Aggregates of Dendritic Multishell Architectures as Universal Nanocarriers," Angew. Chem. Int. Ed. 2007, 46, 1265-1269.
Wiltshire, et al., "Degradable Core Cross-Linked Star Polymers via Ring-Opening Polymerization," Macromolecules, 2006, 39 (13), 4282-4285.
Xiong, et al., "Synthesis of PEG-Armed and Polyphosphoester Core-Cross-Linked Nanogel by One-Step Ring-Opening Polymerization," Macromolecules, 2009, 42 (4), 893-896.
"Functional polycarbonates and their self-assemblies as promising non-viral vectors" Seow, Wei Yang; Yang, Yi Yan, J. of Controll. Release (2009) pp. 1-8.
"Quaternized Polyamidoamine Dendrimers as Novel Gene Delivery System: Relationship between Degree of Quaternization and Their Influences" Lee et al., Bull. Korean Chem. Soc. 2003, vol. 24, No. 11, pp. 1637-1640.
"Polyethylenimine-grafted polycarbonates as biodegradable polycations for gene delivery" Wang et al., Biomaterials 30 (2009) pp. 4824-4832.
"Nonviral Vectors for Gene Delivery" Mintzer, Meredith A.; Simanek, Eric E., Chem. Rev. 2009, 109, pp. 259-302.
"Synthesis, characterization and surface modification of low moduli poly(ether carbonate urethane)ureas for soft tissue engineering" Wang, et al., J. Acta Biomaterialia, 2009, pp. 1-12.
"Tagging alcohols with cyclic carbonate: a versatile equivalent of (meth)acrylate for ring-opening polymerization" Pratt, et al., J. Chem. Commun., 2008, pp. 114-116.
"Mixed Micelle Formation through Stereocomplexation between Enantiomeric Poly(lactide) Block Copolymers" Kim, et al., Macromolecules 2009, 42, pp. 25-29.

(Continued)

*Primary Examiner* — Shaojia Anna Jiang
*Assistant Examiner* — Jonathan S Lau
(74) *Attorney, Agent, or Firm* — Michael R. Roberts

(57) ABSTRACT

A biodegradable block copolymer is disclosed, comprising a hydrophilic block derived from a polyether alcohol; and a hydrophobic block comprising a first repeat unit derived by ring opening polymerization of a first cyclic carbonyl monomer initiated by the polyether alcohol, the first repeat unit comprising a side chain moiety comprising a functional group selected from the group consisting of i) urea groups and ii) mixtures of urea groups and carboxylic acid groups. No side chain of the hydrophobic block comprises a covalently bound biologically active material. The block copolymer self-assembles in water forming micelles suitable for sequestering a biologically active material by a non-covalent interaction, and the block copolymer is 60% biodegraded within 180 days in accordance with ASTM D6400.

44 Claims, 10 Drawing Sheets

OTHER PUBLICATIONS

"Urea-bearing copolymers for guest-dependent tunable self-assembly" Kamps, et al., J. Chem. Commun., 2007, pp. 954-956.

Nanotechnology in Drug Delivery, Melgardt M. de Villiers, Pornanong Aramwit, Glen S. Kwon, Biotechnology: Pharmaceutical Aspects, V 10, of Biotechnology (Arlington, VA.), 2009, Chap. 13, p. 401.

"Amphiphilic Triblock Copolycarbonates with Poly(glycerol carbonate) as Hydrophilic Blocks" Zhang et al., J. Macromolecules 2009, 42, pp. 1010-1016.

"Chemical Structure of Cationic Groups in Amphiphilic Polymethacrylates Modulates the Antimicrobial and Hemolytic Activities" Palermo, Edmund F.; Kuroda, Kenichi, J. Biomacromolecules 2009, 10, pp. 1416-1428.

"The Chemistry and Applications of Antimicrobial Polymers: A State-of-the-Art Review" Kenawy et al., Biomacromolecules, vol. 8, No. 5, May 2007, pp. 1359-1384.

"Synthesis and Characterization of Novel Glycerol-Derived Polycarbonates with Pendant Hydroxyl Groups" Mei, et al., Macromol. Rapid Commun. 2006, 27, 1894-1899.

"Organocatalytic Ring Opening Polymerization of Trimethylene Carbonate" Nederberg et al., Biomacromolecules, 2007, 8, 153-160.

Fukushima, 235th ACS National Meeting, New Orleans, LA United States, Apr. 6-10, 2008, Poly-277 [online], retrieved on Feb. 9, 2011]. Retrieved from the Internet URL: <http://oasys2.confex.com/acs/235nm/techprogram/P1152261.htm>.

Guan, et al., "Synthesis and Characterization of Novel Biodegradable Block Copolymer Poly(ethylene glycol)-block-poly (L-lactide-co-2-methyl-2-carboxyl-propylene carbonate)", Journal of Polymer Science: Part A: Polymer Chemistry, vol. 43, 4771-4780 (2005).

Australian Patent Office, Written Opinion and International Search Report, dated Feb. 23, 2011, PCT/SG2010/000485, Filed Dec. 23, 2010.

* cited by examiner

BIODEGRADABLE BLOCK POLYMERS FOR DRUG DELIVERY, AND METHODS RELATED THERETO

BACKGROUND

The present invention relates to biodegradable block polymers, and more specifically, loaded micelles thereof formed with biologically active materials, for use in drug delivery.

The majority of clinically used drugs are low molecular weight polymer compounds (<500 daltons) that exhibit a short half-life in the blood stream and high clearance rates. These small molecules diffuse rapidly through the body in both healthy and diseased tissue often causing serious side effects. Moreover these therapeutic agents have limited solubility and stability and they are often toxic, making efficient drug delivery systems to overcome these transport problems of critical interest. Polymer therapeutics (including polymeric drugs, polymeric-drug conjugates, polymer-protein conjugates, polymer-DNA conjugates and polymeric micelles to which drugs are covalently bound or physically incorporated) is an ongoing area of research.

The most widely studied delivery agents are supramolecular structures generated from block copolymers where one block is selectively solvated in water. These micelles form core-shell or compartmentalized morphologies capable of sequestering hydrophobic cargos, and are typically several tens of nanometers in diameter with a relatively narrow size distribution. The major obstacle for supramolecular drug-delivery systems based on a non-covalent entrapment of drugs into core-shell architectures is the lack of stability of polymer micelles at high dilution and low drug loading levels. Improvement in stability has been achieved by cross-linking the core or shell of premixed micelles, or by structural designs promoting non-covalent interactions between blocks, including, for example, polyelectrolyte complexation between oppositely charged block ionomers, stereocomplexation, or hydrogen bonding. Despite the improved stability from the chemical cross-linking, this approach may not be optimal for the encapsulation of a guest molecule, or for biodegradability.

In addition, non-covalent interactions can also be used to enhance carrier-cargo complexes to improve loading levels and mitigate cargo release kinetics. For example, interaction between an ammonium ion and a carboxylate anion with the formation of an ion-pair complex is an important type of molecular recognition process. This acid-base motif has been exploited for supramolecular assembly of gels, controlling diblock copolymer self-assembly to form domain patterns, small molecule mixtures, interfaces, surfactant/polymer/dendrimer supramolecular complexes, liquid crystal/polymer complexes, thermally responsive gels, etc. Specific acid-base interaction between hydrophobic drug molecules ($R_1$—COOH) and polymer segments ($NH_2$—$R_2$) improved the drug loading capacity of block copolymer micelles in aqueous media. Similarly, core/shell micelles with acid functionalities in the core sequestered high loading levels of DOX, but unfortunately DOX molecules had to be chemically linked to the core through the acid groups, which did not show biological activity in cancer treatment. Similarly, the use of another non-covalent interaction, stereocomplexation, has been used to significantly bolster drug loadings as well as to control the release rates.

Micelle stability in ultradilute conditions and enhanced cargo-carrier loading levels remain important challenges for drug delivery systems.

SUMMARY

Accordingly, in an embodiment, a biodegradable block copolymer is disclosed, comprising:

a hydrophilic block derived from a polyether alcohol; and
a hydrophobic block comprising a first repeat unit derived by ring opening polymerization of a first cyclic carbonyl monomer initiated by the polyether alcohol, the first repeat unit comprising a side chain moiety comprising a functional group selected from the group consisting of urea groups, a carboxylic acid groups, and mixtures thereof;

wherein no side chain of the hydrophobic block comprises a covalently bound biologically active material, and the block copolymer self-assembles in water, forming micelles suitable for sequestering a biologically active material by a non-covalent interaction, and wherein the block copolymer is 60% biodegraded within 180 days in accordance with ASTM D6400.

In another embodiment is disclosed a method of forming a biodegradable block polymer, the method comprising:

forming a block copolymer by ring opening polymerization of a first cyclic carbonyl monomer initiated by a polyether alcohol, wherein the block copolymer comprises a hydrophilic and a hydrophobic block, the hydrophilic block derived from the polyether alcohol, and the hydrophobic block comprising a first repeat unit comprising a side chain comprising a functional group selected from the group consisting of urea groups, carboxylic acid groups, and mixtures thereof;

wherein the hydrophobic block comprises no side chain comprising a covalently bound biologically active material, the block copolymer forms micelles in water suitable for sequestering a biologically active material by a non-covalent interaction, and the block copolymer is 60% biodegraded within 180 days in accordance with ASTM D6400.

In another embodiment is disclosed a micelle, comprising:

a biodegradable first block copolymer, the first block copolymer comprising a hydrophilic block derived from a polyether alcohol; and a hydrophobic block comprising a first repeat unit derived by ring opening polymerization of a first cyclic carbonyl monomer initiated by the polyether alcohol, the first repeat unit comprising a side chain comprising a functional group selected from the group consisting of urea groups, carboxylic acid groups, and mixtures thereof; wherein no side chain of the hydrophobic block comprises a covalently bound biologically active material, the block copolymer is suitable for sequestering a biologically active material by a non-covalent interaction, and the block copolymer is 60% biodegraded within 180 days in accordance with ASTM D6400.

In another embodiment is disclosed a method of treating a cell, comprising:

contacting a cell with an aqueous mixture comprising nanoparticles of a loaded micelle, the loaded micelle comprising:

a biodegradable first block copolymer, the first block copolymer comprising a hydrophilic block derived from a polyether alcohol, and a hydrophobic block comprising a first repeat unit derived by ring opening polymerization of a first cyclic carbonyl monomer initiated by the polyether alcohol, wherein the first repeat unit comprises a side chain comprising a functional group selected from the group consisting of urea groups, carboxylic acid groups, and mixtures thereof; and a biologically active material;

wherein the first block copolymer is suitable for sequestering the biologically active material by a non-covalent interaction, no side chain of the hydrophobic block is covalently bound to the biologically active material, and the first block copolymer is 60% biodegraded within 180 days in accordance with ASTM D6400.

The above-described and other features and advantages of the present invention will be appreciated and understood by those skilled in the art from the following detailed description, drawings, and appended claims.

DETAILED DESCRIPTION

Figure 1A:
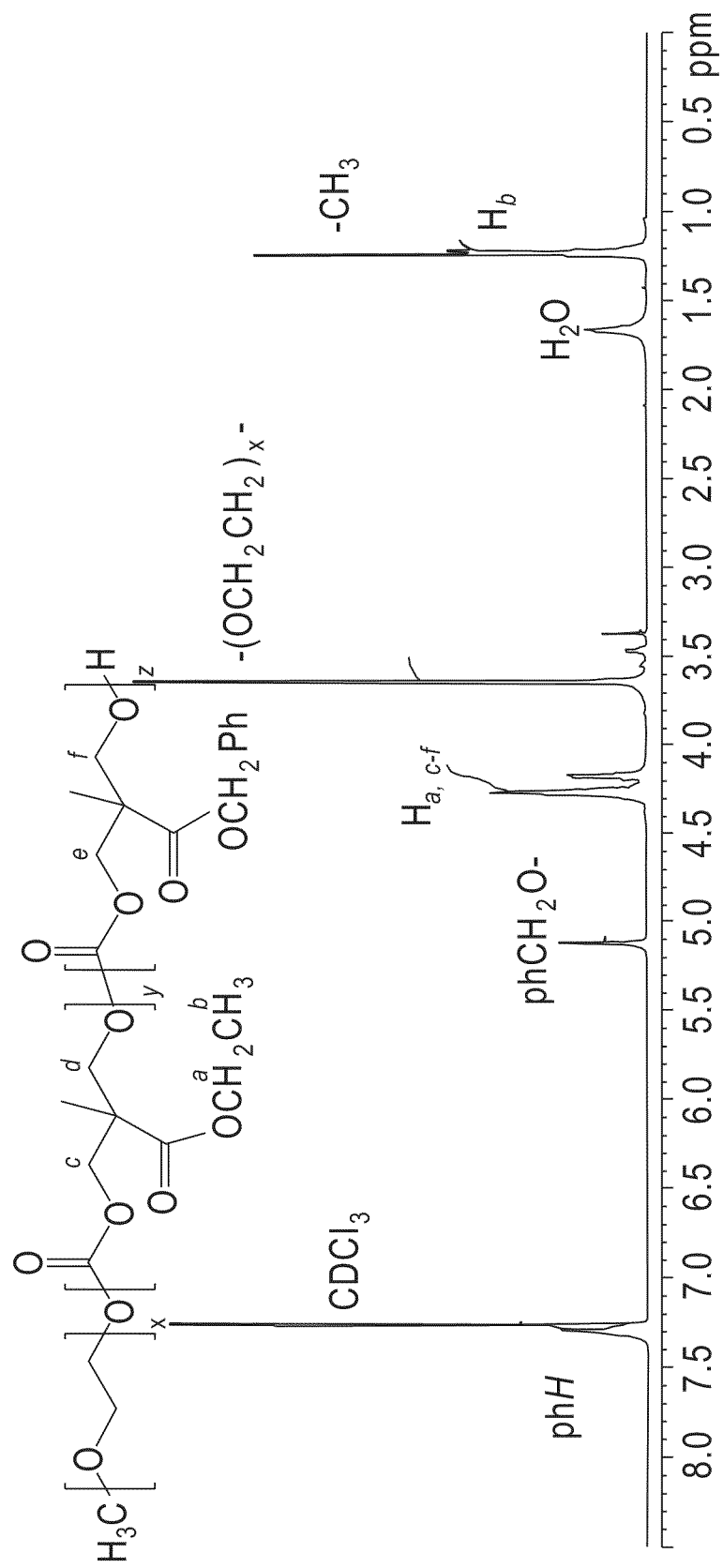
FIG. 1A is a $^1$H NMR spectrum of protected block copolymer Example 3.

Biocompatible and biodegradable block copolymers are disclosed that form micelles in water suitable for sequestering a biologically active material (also referred to as biologically active material herein) by non-covalent interaction. The block polymers comprise a hydrophilic block comprising a polyether backbone, and a hydrophobic block comprising a first repeat unit derived by ring opening polymerization (ROP) of a first cyclic carbonyl monomer comprising a pendant moiety comprising a functional group selected from the group consisting of urea groups, carboxylic acid groups, and mixtures thereof. The hydrophobic block has no biologically active material (e.g., a drug, a peptide, a nucleotide, or a material capable of some cell specific interaction) covalently bound to any side chain. The block copolymers are monodisperse, amphiphilic and exhibit 0% to 20% cytotoxicity, more particularly no cytotoxicity.

The term "biodegradable" is defined by the American Society for Testing and Materials as a degradation caused by biological activity, especially by enzymatic action, leading to a significant change in the chemical structure of the material. For purposes herein, a material is "biodegradable" if it undergoes 60% biodegradation within 180 days in accordance with ASTM D6400.

More specifically, the block copolymers comprise a hydrophilic block derived from a polyether alcohol, which can be a glycol or a mono-alcohol. The polyether alcohol is used to initiate ring-opening polymerization of one or more cyclic carbonate monomers to form the hydrophobic block. The hydrophobic block can be derived from a first cyclic carbonyl monomer comprising a functional group selected from the group consisting of urea groups, carboxylic acid groups, and mixtures thereof. A latent carboxylic acid group is an ester group that can be converted to a carboxylic acid group after the ring-opening polymerization without degrading the main chain. For example, a latent carboxylic acid group can be a protected ester that can be deprotected after the ring opening polymerization.

More particularly, the hydrophobic block further comprises a second repeating unit derived from a second cyclic carbonyl monomer that does not comprise any of the following functional groups: carboxylic acid group, latent carboxylic acid group, or a urea group. The combination of cyclic carbonyl monomers provides control of hydrophobicity, self-association behavior of the block copolymer, and non-covalent binding interactions of the block copolymer with a biologically active "cargo" material, such as a drug. Thus, the block copolymers can be designed to achieve particular micelle forming properties or modulate the non-covalent binding interactions involved in loading and/or releasing a particular biologically active material.

The first cyclic carbonyl monomer can also contain both a urea group and a latent carboxylic acid group, if desired. Urea groups can associate via bifurcated hydrogen bonding, and the hydrogen bond strength exceeds that of amides and urethanes. Urea self-recognition (i.e., urea functionalities interacting with other urea functionalities (A-A system)) simplifies the synthetic procedure compared to conventional A-B pairs (i.e., urea interacting with a different functional group such as a ketone). Ureas can also bind non-covalently to carboxylate derivatives and their isosteres (such as sulfonates, phosphonates, and phosphates), to improve micelle stability and drug loading.

In aqueous solution, the block copolymers reversibly self-associate to form nano-sized micelles having a lower critical micelle concentration (CMC) compared to micelles formed from block copolymers lacking a pendant urea and/or carboxylic acid group. The block copolymers can be used singly to form homo-micelles, or in combination to form mixed micelles. In particular, carboxylic acid-containing block copolymers can be used to form mixed micelles with urea-containing block copolymers. The urea and carboxylic acid mole fractions of the mixed micelles can be adjusted advantageously, through formulation rather than synthetic modification, to allow optimization of drug loading, chain aggregation number, critical micelle concentration, and drug release properties of the micelle forming composition. The block copolymers reversibly associate with a cargo material to form nano-sized loaded micelles. High loadings of low molecular weight cargo (M$_n$<300 dalton) have been achieved. Surprisingly, the average size of a loaded micelle (also referred to as a block copolymer-cargo conjugate) is about 100 nm at drug loadings of about 10 wt. % to 40 wt. % based on dry weight of the loaded micelle.

The micelle forming block copolymers have the general formula (1):

$$A'\text{-b-}[P(Monomer1, \ldots)] \tag{1}$$

where A' represents a hydrophilic block derived from a polyether alcohol, "-b-" indicates a block boundary, and [P(Monomer1, . . . )] represents the hydrophobic block formed by ring opening polymerization of one or more cyclic carbonyl monomers. The brackets "[ ]" indicate the hydrophobic block and the "P( )" indicates ring opening polymerization of the one or more cyclic carbonyl monomers contained within the parentheses. The hydrophobic block can comprise a polymer chain comprising a homopolymer formed from a single cyclic carbonyl monomer, a random copolymer formed from two or more cyclic carbonyl monomers (indicated by "-r-" separating the monomer names in formula (1)), a block copolymer formed from two or more cyclic carbonyl monomers (indicated by "-b-" separating the two or more cyclic carbonyl monomers), or a mixture of thereof. That is, the hydrophobic block can itself comprise any one of, or a mixture of, these polymer chain types.

For example, a block copolymer described further below is represented by the formula MPEG1-b-[P(MTCOEt-r-MTCU)], where the hydrophilic block is derived from monomethyl poly(ethylene glycol) (MPEG1), and the hydrophobic block consists of a random copolymer derived from two cyclic carbonyl monomers MTCOEt and MTCU having the following structures:

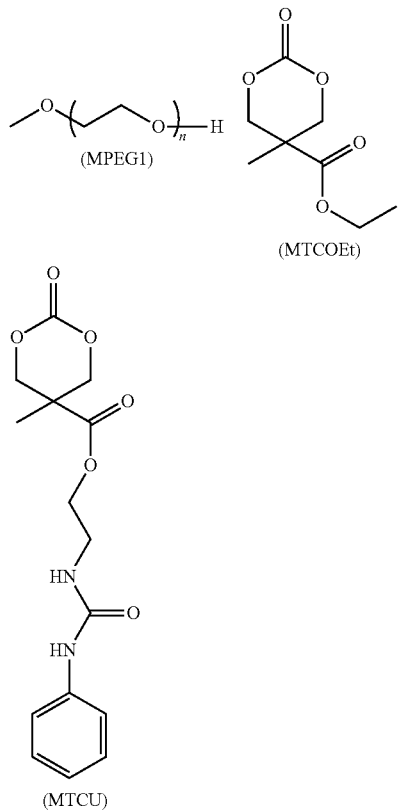

where n is an integer from 2 to 10000. MPEG1-b-[P(MT-COEt-r-MTCU)] has the structure:

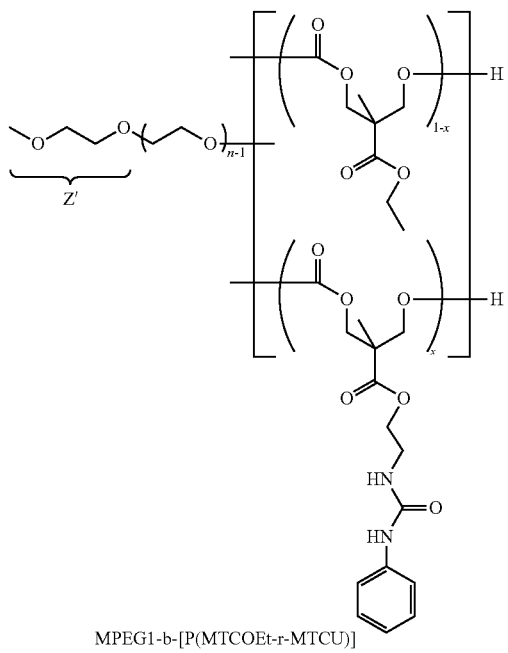

MPEG1-b-[P(MTCOEt-r-MTCU)]

MPEG1-b-[P(MTCOEt-r-MTCU)]
where the vertical stacking of the carbonate repeat units in the hydrophobic block indicates random arrangement of the repeat units; that is, either carbonate repeat unit can be attached to the MPEG1 chain. The hydrophilic block can optionally comprise a derivatized end repeat unit, Z', and the hydrophobic block can also optionally comprise a derivatized end repeat unit, Z". In the example above, the hydrophilic block of MPEG1-b-[P(MTCOEt-r-MTCU)] comprises a derivatized end repeat unit having the structure $MeOCH_2CH_2O$—. Z' and Z" can be monovalent radicals comprising from 1 to 100 carbons. Z' and Z" can represent an endcapped terminal repeat unit, for example an acetyl or methyl endcapped repeat unit as shown above. Alternatively, Z' and Z" can represent more synthetically complex derivatives of the end repeat unit of the hydrophilic and/or hydrophobic blocks. No limitation is placed on the functional groups Z' and Z" can contain, with the proviso that the cargo loading properties, micelle forming properties, drug release properties, and/or cell targeting properties of the block copolymer are not adversely affected. Z' and Z" can independently comprise one or more of the following groups: ketone groups, carboxylic acid groups, ester groups, thioester groups, ether groups, amide groups, amine groups, aldehyde groups, alkene groups, alkyne groups, cycloaliphatic rings comprising 3 to 10 carbons, heterocylic rings comprising 2 to 10 carbons, or combinations of the foregoing additional functional groups. The heterocyclic ring can comprise oxygen, sulfur and/or nitrogen.

The polyether alcohol initiator for the ring opening polymerization can comprise one or more hydroxy groups. More particularly, the polyether alcohol can be a poly(alkylene glycol) of the general formula (2):

$$HO\text{—}[CH_2(CHR^5)_xCHR^5O]_n\text{—}H \tag{2},$$

where x is 0 to 8, each $R^5$ is a monovalent radical independently selected from hydrogen, alkyl group comprising 1 to 30 carbons, or aryl group comprising 6 to 30 carbons. Subscript n is an integer from 2 to 10000. Thus, the ether repeat unit comprises 2 to 10 backbone carbons between each backbone oxygen. Alternatively, the poly(alkylene glycol) can be a mono endcapped poly(alkylene glycol), represented by the formula (3):

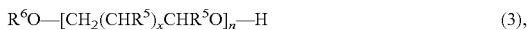
$$R^6O-[CH_2(CHR^5)_xCHR^5O]_n-H \qquad (3),$$

wherein $R^6$ is a monovalent hydrocarbon radical comprising 1 to 20 carbons.

As non-limiting examples, the polyether alcohol can be a poly(ethylene glycol) (PEG), having the structure HO-[—CH$_2$CHR$^5$O]$_n$—H, wherein the ether repeat unit CH$_2$CHR$^5$O (shown in the brackets) comprises two backbone carbons linked to a backbone oxygen. The polyether alcohol can also be a polypropylene glycol) (PPG) having the structure HO—[CH$_2$CHR$^5$CHR$^5$O]$_n$—H, where the ether repeat unit CH$_2$CHR$^5$O comprises three backbone carbons linked to a backbone oxygen. An example of mono endcapped PEG is commercially available monomethyl PEG, wherein one end repeat unit has the structure CH$_3$OCH$_2$CH$_2$O—. The end repeat unit of the mono-derivatized poly(alkylene glycol) can comprise more elaborate chemical structures, represented generally by the general formula (4):

$$Z'-[CH_2(CHR^5)_xCHR^5O]_{n-1}-H \qquad (4),$$

wherein Z'— is a monovalent radical including the backbone carbons and oxygen of the end repeat unit, and can have 2 to 100 carbons. The following non-limiting examples illustrate mono end-derivatization of the polyether alcohol initiator based on PEG. As described above, one end unit of PEG can be capped with a monovalent hydrocarbon group having 1 to 20 carbons, such as the monomethyl PEG, wherein Z'— is MeOCH$_2$CH$_2$O— as shown above. In another example, one end unit of PEG is an aldyhyde, wherein Z'— can be OCHCH$_2$CH$_2$O—. Treating the aldehyde with a primary amine produces an imine, wherein Z'— is R$^7$N=CHCH$_2$CH$_2$O—. R$^7$ is a monovalent radical selected from hydrogen, an alkyl group of 1 to 30 carbons, or an aryl group comprising 6 to 100 carbons. Continuing, the imine can be reduced to an amine, wherein Z'— is R$^7$NHCH$_2$CH$_2$CH$_2$O—. In another example, one end repeat unit of PEG can be oxidized to a carboxylic acid, wherein Z'— is HOOCCH$_2$O—. Using known methods the carboxylic acid can be converted to an ester, wherein Z'— becomes R$^7$OOCCH$_2$O—. Alternatively, the carboxylic acid can be converted to an amide, wherein Z' becomes R$^7$NHOCCH$_2$O—. Many other derivatives are possible. In a particular embodiment, Z'— is a group comprising a biologically active moiety that interacts with a specific cell type. For example, the Z' group can comprise a galactose moiety which specifically recognizes liver cells. In this instance, Z'— can have the structure:

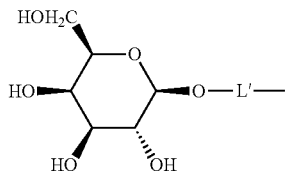

where -L'- is a divalent linking group comprising 2 to 50 carbons containing the end unit of the hydrophilic block. The hyphen on the right side of L' is the bond to the hydrophobic block. Z' can comprise other biologically active moieties such as mannose.

The polyether alcohol used as initiator for the ring opening polymerization can comprise a poly(alkylene glycol), a mono-derivatized poly(alkylene glycol), or mixtures thereof. The polyether alcohol initiator can comprise a mono-derivatized end repeat unit; alternatively, the mono-derivatized end repeat unit can be formed after the ring opening polymerization.

The number average molecular weight of the polyether alcohol can be from 100 to 100,000, more specifically 100 to 10000, and even more specifically, 100 to 5000.

The hydrophobic block of the block copolymers comprises repeating units derived from one or more cyclic carbonyl monomers by ring opening polymerization. A first cyclic carbonyl monomer comprises a pendant moiety comprising a urea group, a latent carboxylic acid group, or a mixture thereof. The pendant moiety becomes a side chain to the hydrophobic block. In an embodiment, a second cyclic carbonyl monomer, when present, does not comprise a pendant moiety comprising a urea group, latent carboxylic acid group, or a mixture thereof. Additional cyclic carbonyl monomers, when present, can optionally comprise a pendant moiety comprising a urea group, latent carboxylic acid group, or a mixture thereof. Several general formulas for the cyclic carbonyl monomers are presented below.

The cyclic carbonyl monomer can have the general formula (5):

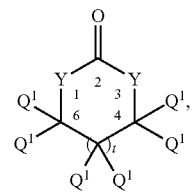

(5)

wherein t is an integer from 0 to 6, and when t is 0 carbons labeled 4 and 6 are linked together by a single bond. Each Y is a divalent radical independently selected from

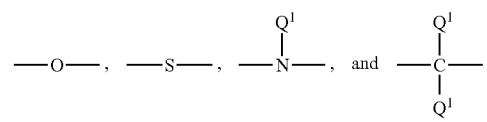

where the dashes "-" indicate the point of attachment in the ring. The latter two groups are also expressed herein as —N(Q$^1$)- and —C(Q$^1$)$_2$-. Each Q$^1$ is a monovalent radical independently selected from the group consisting of hydrogen, halides, alkyl groups comprising 1 to 30 carbons, aryl groups comprising 6 to 30 carbon atoms, and groups having the structure

where M$^1$ is a monovalent radical selected from —R$^1$, —OR$^1$, —NHR$^1$, —NR$^1$R$^1$, or —SR$^1$ (where, as before, the dash represents the point of attachment). R$^1$ is a monovalent radical independently selected from the group consisting of alkyl groups comprising 1 to 30 carbons, and aryl groups comprising 6 to 30 carbons. Each Q$^1$ group can independently comprise a functional group selected from the group consisting of urea groups, latent carboxylic acids, and mixtures thereof. When $Q^1$ is not hydrogen, $Q^1$ represents a pendant moiety to the cyclic carbonyl ring which becomes a side chain to the hydrophobic block after the ring opening polymerization. The urea group can comprise a monovalent urea radical of the formula

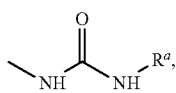

or a divalent urea radical of the formula

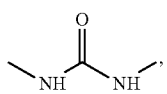

wherein $R^a$ independently comprises a monovalent radical selected from hydrogen, alkyl groups comprising 1 to 30 carbons, or aryl groups comprising 6 to 30 carbons. The urea group can be a terminal urea group on the pendant moiety. Each $Q^1$ group can independently be branched or non-branched. Each $Q^1$ group can further independently comprise one or more additional functional groups selected from the group consisting of ketone groups, aldehyde groups, alkene groups, alkyne groups, cycloaliphatic rings comprising 3 to 10 carbons, heterocyclic rings comprising 2 to 10 carbons, ether groups, amide groups, ester groups, and combinations of the foregoing additional functional groups. The heterocyclic ring can comprise oxygen, sulfur and/or nitrogen. Two or more $Q^1$ groups can together form a ring. In an embodiment, one $Q^1$ group comprises a monovalent urea radical. In another embodiment, one or more $Q^1$ groups comprise a latent carboxylic acid group capable of being converted to a carboxylic acid after ring-opening polymerization. In an embodiment, the first cyclic carbonyl monomer is a compound of formula (5), wherein one or more $Q^1$ groups comprise a functional group selected from the group consisting of i) urea groups and ii) mixtures of urea groups and carboxylic acid groups.

The cyclic carbonyl monomer can have the general formula (6):

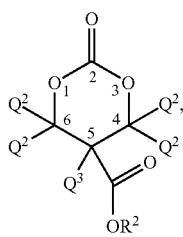

(6)

wherein $Q^2$ is a monovalent radical independently selected from the group consisting of hydrogen, halides, alkyl groups comprising 1 to 30 carbons, aryl groups comprising 6 to 30 carbon atoms, and groups having the structure

wherein $M^1$ is a monovalent radical selected from the group consisting of —$R^1$, —$OR^1$, —$NHR^1$, —$NR^1R^1$, and —$SR^1$, wherein each $R^1$ is a monovalent radical independently selected from the group consisting of alkyl groups comprising 1 to 30 carbons, and aryl groups comprising 6 to 30 carbons; $Q^3$ is a monovalent radical selected from the group consisting of hydrogen, alkyl groups having 1 to 30 carbons, and aryl groups having 6 to 30 carbons; and $R^2$ is a monovalent radical independently selected from the group consisting of alkyl groups comprising 1 to 30 carbons, and aryl groups comprising 6 to 30 carbons. When $Q^2$ and $Q^3$ are not hydrogen, $Q^2$ and $Q^3$ represent pendant moieties to the cyclic carbonyl ring that become side chains to the hydrophobic block after ring opening polymerization. The —$CO_2R^2$ group also becomes a side chain to the hydrophobic block after ring opening polymerization. Each $Q^2$, $Q^3$, and/or $R^2$ group can independently comprise one or more urea groups, one or more latent carboxylic acid groups, or combinations thereof. The urea group can comprise a monovalent urea radical or a divalent urea radical as described above. In an embodiment, the $R^2$ group comprises a functional group selected from the group consisting of urea groups, latent carboxylic acid groups, and mixtures thereof. In another embodiment, $Q^2$ is hydrogen, $Q^3$ is a methyl or ethyl group, and $R^2$ group comprises a functional group selected from the group consisting of urea groups, latent carboxylic acid groups, and mixtures thereof. In another embodiment, the first cyclic carbonyl monomer comprises a compound of formula (6), wherein one or more $Q^2$, $Q^3$, and/or $R^2$-groups comprises a functional group selected from the group consisting of i) urea groups and ii) mixtures of urea groups and carboxylic acid groups.

The cyclic carbonyl monomer can have the general formula (7):

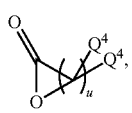

(7)

wherein each $Q^4$ is a monovalent radical independently selected from the group consisting of hydrogen, halides, carboxy groups, alkyl groups comprising 1 to 30 carbons, aryl groups comprising 6 to 30 carbon atoms, and groups having the structure

where $M^1$ is a monovalent radical selected from —$R^1$, —$OR^1$, —$NHR^1$, —$NR^1R^1$, or —$SR^1$ wherein each $R^1$ is a monovalent radical independently selected from the group consisting of alkyl groups comprising 1 to 30 carbons, and aryl groups comprising 6 to 30 carbons; and u is an integer from 1 to 8. When $Q^4$ is not hydrogen, $Q^4$ represents a pendant moiety to the cyclic carbonyl ring that becomes a side chain to the hydrophobic block after ring opening polymerization. Each $Q^4$ can independently comprise a functional group selected from the group consisting of urea groups, a latent carboxylic acid groups, and mixtures thereof. The lactone ring can optionally comprise a carbon-carbon double bond; that is, optionally, a

group of formula (3) can independently represent a

group. The lactone ring can also comprise a heteroatom not linked to the ring carbonyl or ring oxygen, such as oxygen, nitrogen, sulfur, or a combination thereof; that is, optionally a

group of formula (3) can independently represent a —O—, —S—, —NHR$^1$—, or an —NR$^1$R$^1$— group. In an embodiment, u is an integer from 1 to 6 and each Q$^4$ is hydrogen. In an embodiment, the first cyclic carbonyl monomer has the formula (7), wherein one or more Q$^4$ groups comprises a functional group selected from the group consisting of i) urea groups and ii) mixtures of urea groups and carboxylic acid groups.

The cyclic carbonyl monomer can have the general formula (8):

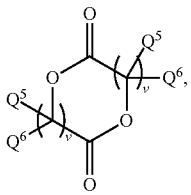

(8)

wherein each Q$^5$ is a monovalent radical independently selected from the group consisting of hydrogen, halides, alkyl groups comprising 1 to 30 carbons, aryl groups comprising 6 to 30 carbon atoms, and groups having the structure

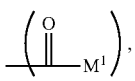

where M$^1$ is a monovalent radical selected from —R$^1$, —OR$^1$, —NHR$^1$, —NR$^1$R$^1$, or —SR$^1$, where the dash represents the point of attachment; each R$^1$ is a monovalent radical independently selected from the group consisting of alkyl groups comprising 1 to 30 carbons, and aryl groups comprising 6 to 30 carbons; each Q$^6$ is a monovalent group independently selected from the group consisting of hydrogen, alkyl groups having 1 to 30 carbons, and aryl groups having 6 to 30 carbons; and each v is independently an integer from 1 to 6. When Q$^5$ and Q$^6$ are not hydrogen, Q$^5$ and Q$^6$ represent pendant moieties to the cyclic carbonyl ring that become side chains to the hydrophobic block after ring opening polymerization. Each Q$^5$ and Q$^6$ group can independently comprise a functional group selected from the group consisting of urea groups, latent carboxylic acid groups, and mixtures thereof. In an embodiment, each v is 1, each Q$^5$ is hydrogen, and each Q$^6$ is a hydrocarbon group comprising 1 to 6 carbons. In an embodiment, the first cyclic carbonyl monomer has the formula (8), wherein one or more Q$^5$ and/or a Q$^6$ group comprises a functional group selected from the group consisting of i) urea groups and ii) mixtures of urea groups and carboxylic acid groups.

Non-limiting examples of latent carboxylic acids include esters that can be hydrolyzed under mild conditions (e.g., trifluoroethyl ester, pentafluorophenyl ester, or p-nitrophenyl ester, N-hydroxysuccinimimide ester, trimethylsilyl ester, tetrahydropyranyl ester). Other latent carboxylic acids include thermally labile tertiary esters (e.g., t-butyl esters). Still other latent carboxylic acids include esters capable of being reductively cleaved using hydrogen and a suitable catalyst (e.g., benzyl esters, cleavable by H/Pd—C). In an embodiment, the latent carboxylic acid group is any carboxylic ester that can be converted to a carboxylic acid by hydrogenation with a catalyst. A non-limiting example of a cyclic carbonyl monomer comprising a latent carboxylic acid that can be converted to a carboxylic acid by hydrogenation with a catalyst is MTCOBn.

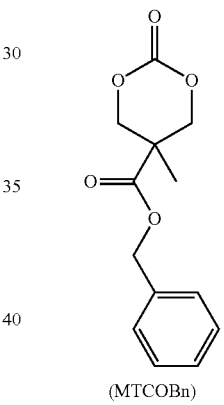

(MTCOBn)

The benzyl ester of MTCOBn cleaved to a carboxylic acid using H/Pd—C after the ring opening polymerization. In another embodiment, a latent carboxylic acid excludes methyl, ethyl or longer hydrocarbon chain esters when the backbone of the hydrophobic block comprises ester and/or carbonate repeat units.

Another example of a latent carboxylic acid group is an acetal-protected carboxylic acid group, herein also referred to as an acetal ester group. The acetal ester group has the general formula (9)

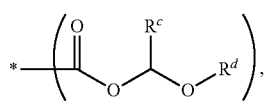

(9)

wherein *- represents the bond to a cyclic carbonyl moiety, and R$^c$ and R$^d$ are monovalent radicals independently comprising from 1 to 20 carbons. In an embodiment, R$^c$ is methyl and R$^d$ is ethyl. In another embodiment, the second cyclic carbonyl monomer is MTCOEE:

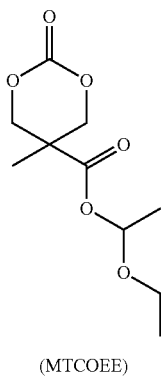 [SMILES: CCOC(C)OC(=O)C1(C)COC(=O)OC1]

(MTCOEE)

When copolymerized into the polymer, repeat units derived from MTCOEE comprise a side chain acetal ester that is readily deprotected in the acidic endosomal environment. Once released into the cytoplasm, the resulting carboxylic acid groups of the cationic polymer can be deprotonated, thus neutralizing the net charge on the carrier and potentially facilitating the release of the biologically active material.

A non-limiting example of a cyclic carbonyl monomer comprising a pendant moiety comprising a urea group is MTCU. In an embodiment, the first cyclic carbonyl monomer is MTCU.

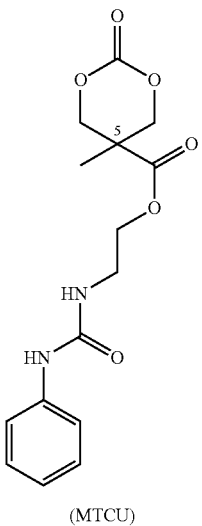 [SMILES: CC1(C(=O)OCCNC(=O)Nc2ccccc2)COC(=O)OC1]

(MTCU)

The methyl and ester group attached to carbon 5 are each a pendant moiety.

Additional cyclic carbonyl monomers of formulas (6), (7), and (8) are listed in Table 1.

TABLE 1

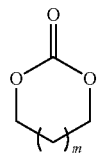

m = 1, Trimethylene carbonate (TMC)
m = 2, Tetramethylene carbonate (TEMC)
m = 3, Pentamethylene carbonate (PMC)

TABLE 1-continued

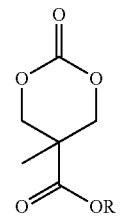

R = hydrogen (MTCOH)
R = methyl (MTCOMe)
R = t-butyl (MTCO$^t$Bu)
R = ethyl (MTCOEt)

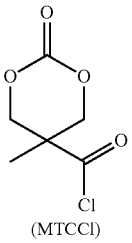

(MTCCl)

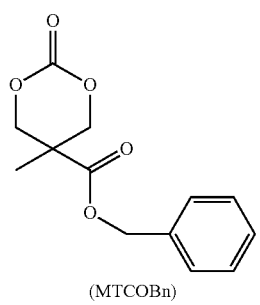

(MTCOBn)

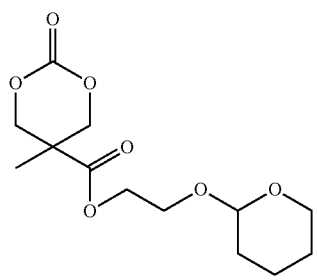 [SMILES: CC1(C(=O)OCCOC2CCCCO2)COC(=O)OC1]

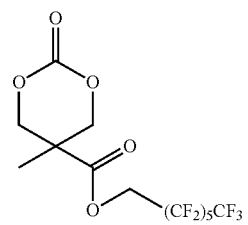

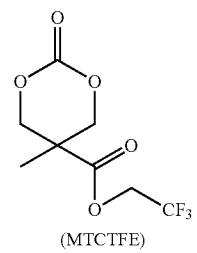

(MTCTFE)

TABLE 1-continued
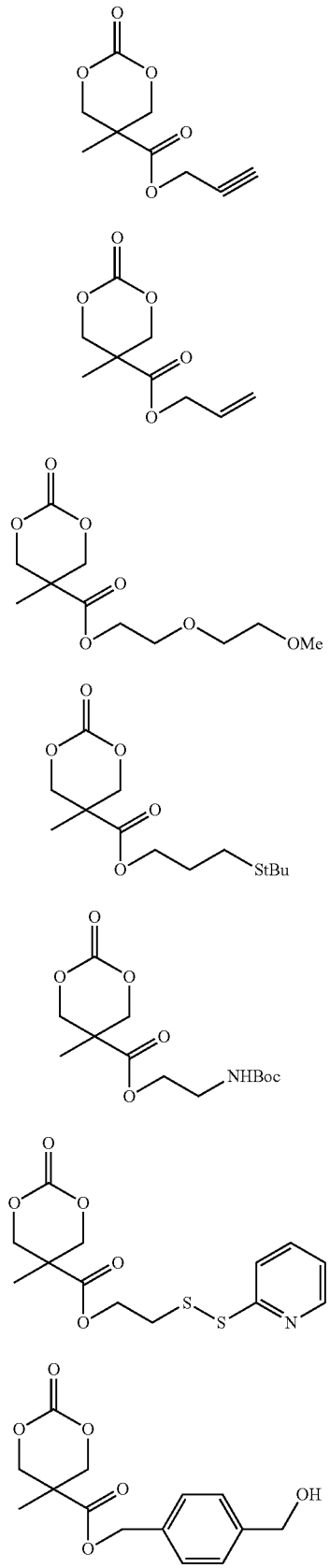
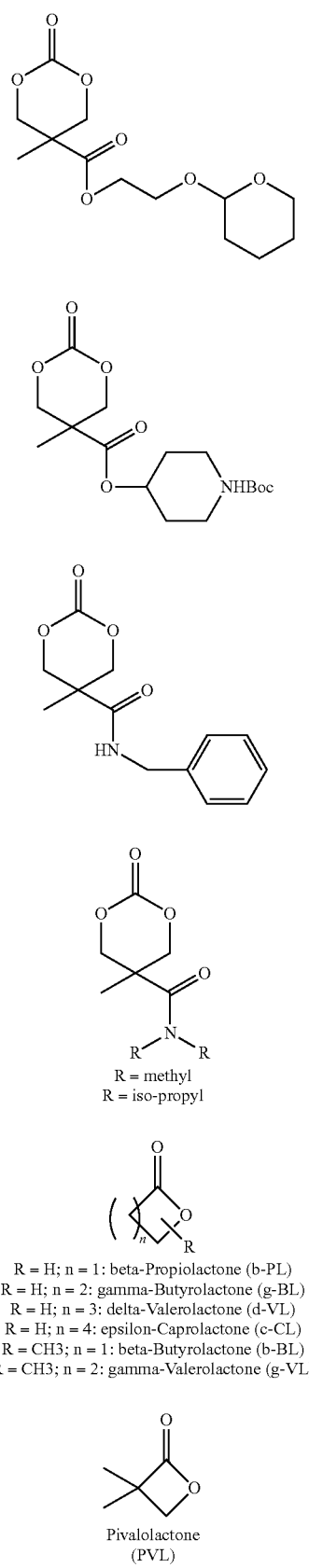

TABLE 1-continued

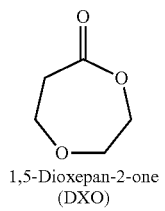

1,5-Dioxepan-2-one
(DXO)

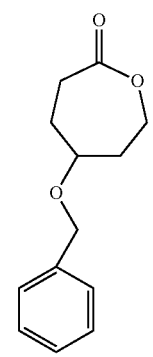 [SMILES: O=C1CCC(OCc2ccccc2)CCO1]

5-(Benzyloxymethyl)oxepan-2-one
(BOMXO)

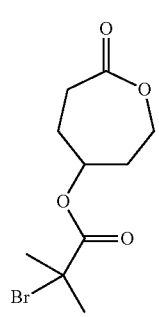

7-Oxooxepan-4-yl 2-bromo-2-
methylpropanoate
(BMP-XO)

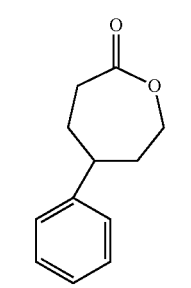 [SMILES: O=C1CCC(c2ccccc2)CCO1]

5-Phenyloxepan-2-one
(PXO)

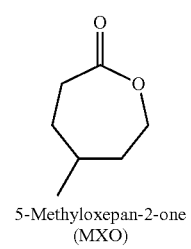

5-Methyloxepan-2-one
(MXO)

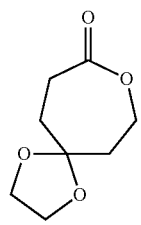 [SMILES: O=C1CCC2(CCO1)OCCO2]

1,4,8-Trioxa(4,6)spiro-9-undecane
(TOSUO)

5-(Benzyloxymethyl)oxepan-2-one
(BOMXO)

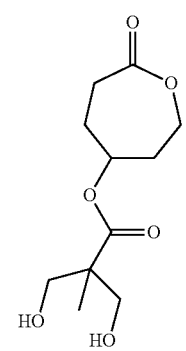

7-Oxooxepan-4-yl 3-hydroxy-2-
(hydroxymethyl)-2-methylpropanoate
(OX-BHMP)

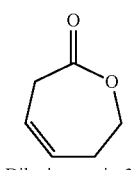

(Z)-6,7-Dihydrooxepin-2(3H)-one
(DHXO)

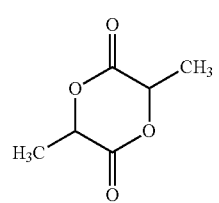

D-Lactide (DLA)
L-Lactide (LLA) or
racemic Lactide, 1:1 D:L forms (DLLA)

TABLE 1-continued

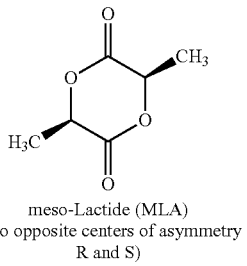

meso-Lactide (MLA)
(two opposite centers of asymmetry R and S)

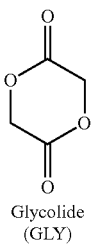

Glycolide
(GLY)

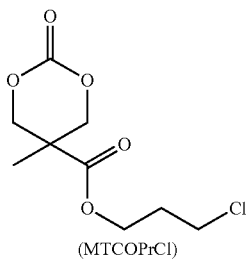

(MTCOPrCl)

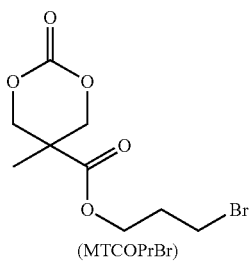

(MTCOPrBr)

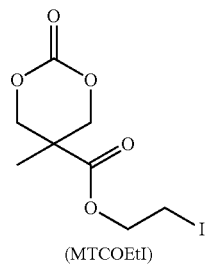

(MTCOEtI)

The cyclic carbonyl monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

The cyclic carbonyl monomers can also comprise isotopically enriched forms of the cyclic carbonyl monomers. These include functional groups comprising elements selected from the group consisting of $^{13}C$, $^{14}C$, $^{15}N$, deuterium, tritium, and combinations thereof. The cyclic carbonyl monomers can also comprise a radioactive moiety suitable for targeting a specific cell type, such as a cancer cell. The radioactive moiety can comprise a heavy metal radioactive isotope.

The above-described cyclic carbonyl monomers undergo ring-opening polymerization to form the hydrophobic block of the block copolymers linked to the hydrophilic block derived from the polyether alcohol. The hydrophobic block can comprise a homopolymer chain comprising repeat units derived by ring opening polymerization of a single cyclic carbonyl monomer, the repeat units comprising a side chain comprising a functional group selected from urea, carboxylic acid, or mixture thereof. The hydrophobic block can comprise a random copolymer chain comprising a first repeat unit and a second repeat unit derived by ring opening polymerization of a mixture of a first cyclic carbonyl monomer and a second cyclic carbonyl monomer. The first repeat derived from the first cyclic carbonyl monomer comprises a side chain moiety comprising a functional group selected from urea, carboxylic acid, or mixture thereof. In an embodiment, the second repeat unit derived from the second cyclic carbonyl monomer comprises no side chain moiety comprising a urea group, a carboxylic acid group, or a mixture thereof.

The hydrophobic block can also comprise a core block copolymer comprising a first core block and a second core block derived by sequential ring opening polymerization of a first cyclic carbonyl monomer and a second cyclic carbonyl monomer. The first cyclic carbonyl monomer comprises a moiety comprising a functional group selected from urea, latent carboxylic acid, or mixture thereof. The polymerization can be performed in any desirable sequential order. No limitation is placed on the number of core blocks of the hydrophobic block providing the micelle-forming properties and the drug loading and drug release properties of the micelles are not degraded. For example, the hydrophobic block can comprise a first core block and a second core block. The first core block is linked to the hydrophilic block and the first core block comprises, for example, the first repeat units derived from the first cyclic carbonyl monomer. The second core block is linked to the first core block, and the second sub-block comprises, for example, second repeat units derived from the second cyclic carbonyl monomer. Alternatively, the first core block can be derived from the second cyclic carbonyl monomer, and the second core block can be derived from the first cyclic carbonyl monomer. In an embodiment, the second repeat unit comprises no side chain moiety comprising a urea group, a carboxylic acid group, or a mixture thereof.

The hydrophobic block can be produced in atactic, syndiotactic or isotactic forms. The particular tacticity depends on the cyclic monomer(s), isomeric purity, and the reaction conditions.

The micelle forming block copolymers are prepared from a reaction mixture comprising one or more cyclic carbonyl monomers, at least one of which comprises a functional group selected from urea, latent carboxylic acid, or mixture thereof; a catalyst; an optional accelerator; an optional solvent, and a polyether alcohol initiator. The ring opening polymerization is generally conducted in a reactor under inert atmosphere such as nitrogen or argon. The polymerization can be performed by solution polymerization in an inactive solvent such as benzene, toluene, xylene, cyclohexane, n-hexane, dioxane, chloroform and dichloroethane, or by bulk polymerization. The ROP reaction temperature can be from about ambient temperature to 250° C. Generally, the reaction mixture is heated at atmospheric pressure for 0.5 to 72 hours to effect polymerization, forming a second mixture.

Exemplary catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Other ROP catalysts include metal-free organocatalysts that can provide a platform to polymers having controlled, predictable molecular weights and narrow polydispersities. Examples of organocatalysts for the ROP of cyclic esters, carbonates and siloxanes are 4-dimethylaminopyridine, phosphines, N-heterocyclic carbenes (NHC), bifunctional aminothioureas, phosphazenes, amidines, and guanidines. In an embodiment the catalyst is N-(3,5-trifluoromethyl)phenyl-N'-cyclohexyl-thiourea (TU):

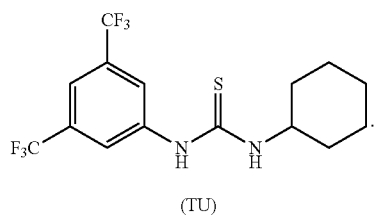 [SMILES: FC(F)(F)c1cc(NC(=S)NC2CCCCC2)cc(C(F)(F)F)c1 ; "(TU)"]

(TU)

In another embodiment, the catalyst and the accelerator are the same compound, such as 1,8-diazabicyclo[5.4.0]undec-7-ene (DBU). Another metal-free ROP catalyst comprises at least one 1,1,1,3,3,3-hexafluoropropan-2-ol-2-yl (HFP) group. Singly-donating hydrogen bond catalysts have the formula (10):

$$R^2—C(CF_3)_2OH \quad (10).$$

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 2.

TABLE 2

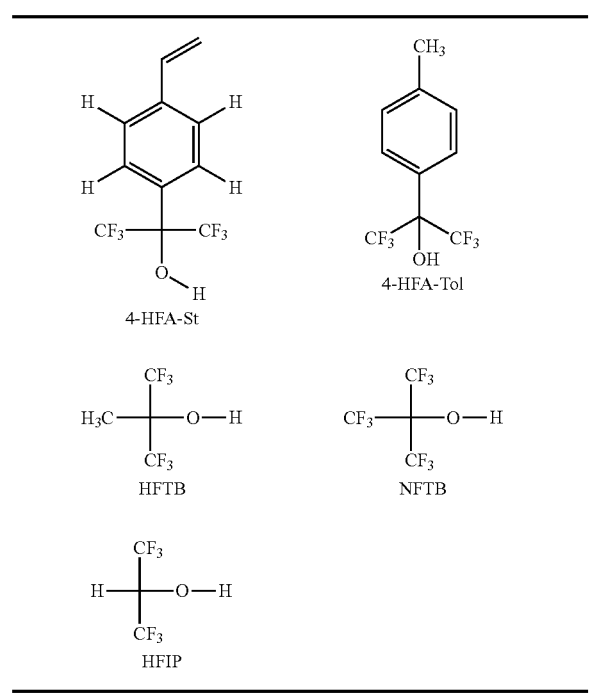

Doubly-donating hydrogen bonding catalysts have two HFP groups, represented by the general formula (11):

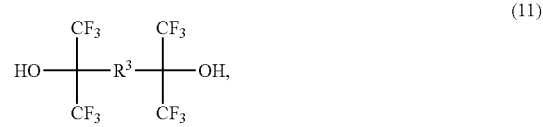

(11)

wherein $R^3$ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (11) include those listed in Table 3. In a specific embodiment, $R^2$ is an arylene or substituted arylene group, and the HFP groups occupy positions meta to each other on the aromatic ring.

TABLE 3

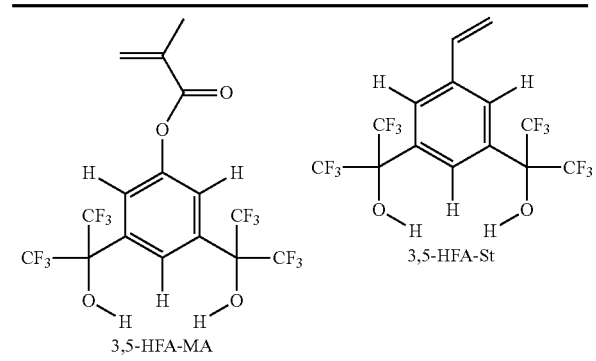

TABLE 3-continued

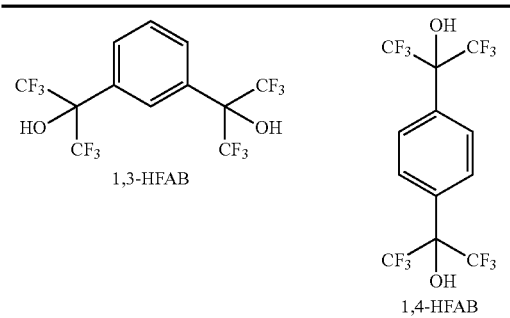

1,3-HFAB 1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Typical examples of such polymerizeable HFP-containing monomers may be found in: Ito et al., *Polym. Adv. Technol.* 2006, 17(2), 104-115, Ito et al., *Adv. Polym. Sci.* 2005, 172, 37-245, Ito et al., US20060292485, Maeda et al. WO2005098541, Allen et al. US20070254235, and Miyazawa et al. WO2005005370. Alternatively, pre-formed polymers and other solid support surfaces can be modified by chemically bonding an HFP-containing group to the polymer or support via a linking group. Examples of such polymers or supports are referenced in M. R. Buchmeiser, ed. "Polymeric Materials in Organic Synthesis and Catalysis," Wiley-VCH, 2003, M. Delgado and K. D. Janda "Polymeric Supports for Solid Phase Organic Synthesis," *Curr. Org. Chem.* 2002, 6(12), 1031-1043, A. R. Vaino and K. D. Janda "Solid Phase Organic Synthesis: A Critical Understanding of the Resin", *J. Comb. Chem.* 2000, 2(6), 579-596, D. C. Sherrington "Polymer-supported Reagents, Catalysts, and Sorbents: Evolution and Exploitation—A Personalized View," *J. Polym. Sci. A. Polym. Chem.* 2001, 39(14), 2364-2377, and T. J. Dickerson et al. "Soluble Polymers as Scaffold for Recoverable Catalysts and Reagents," *Chem. Rev.* 2002, 102(10), 3325-3343. Examples of linking groups include $C_1$-$C_{12}$ alkyl, $C_1$-$C_{12}$ heteroalkyl, an ether group, a thioether group, an amino group, an ester group, an amide group, or a combination thereof. Also contemplated are catalysts comprising charged HFP-containing groups bound by ionic association to oppositely charged sites on a polymer or a support surface.

The ROP reaction mixture comprises at least one catalyst and, when appropriate, several catalysts together. The ROP catalyst is added in a proportion of 1/20 to 1/40,000 moles relative to the cyclic carbonyl monomers, and preferably of 1/1,000 to 1/20,000 moles.

The ring-opening polymerization is conducted in the presence of an accelerator, in particular a nitrogen base. Exemplary nitrogen base accelerators are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl) imidazol-2-ylidene (Im-2), 1,3-bis(2,6-di-1-propylphenyl (imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis (2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 4.

TABLE 4

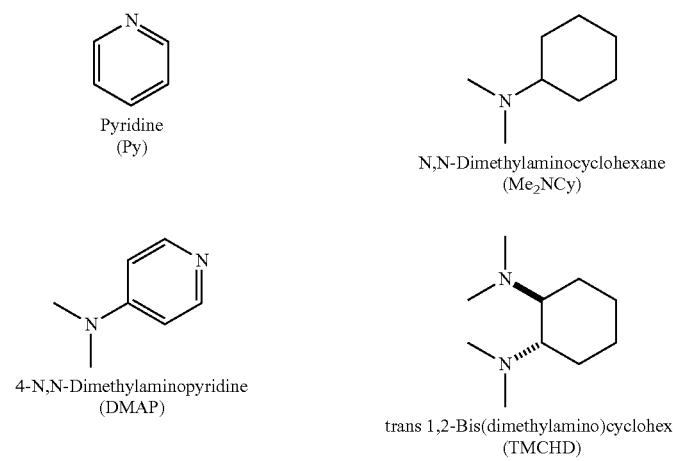

Pyridine (Py)

N,N-Dimethylaminocyclohexane ($Me_2NCy$)

4-N,N-Dimethylaminopyridine (DMAP)

trans 1,2-Bis(dimethylamino)cyclohexane (TMCHD)

TABLE 4-continued

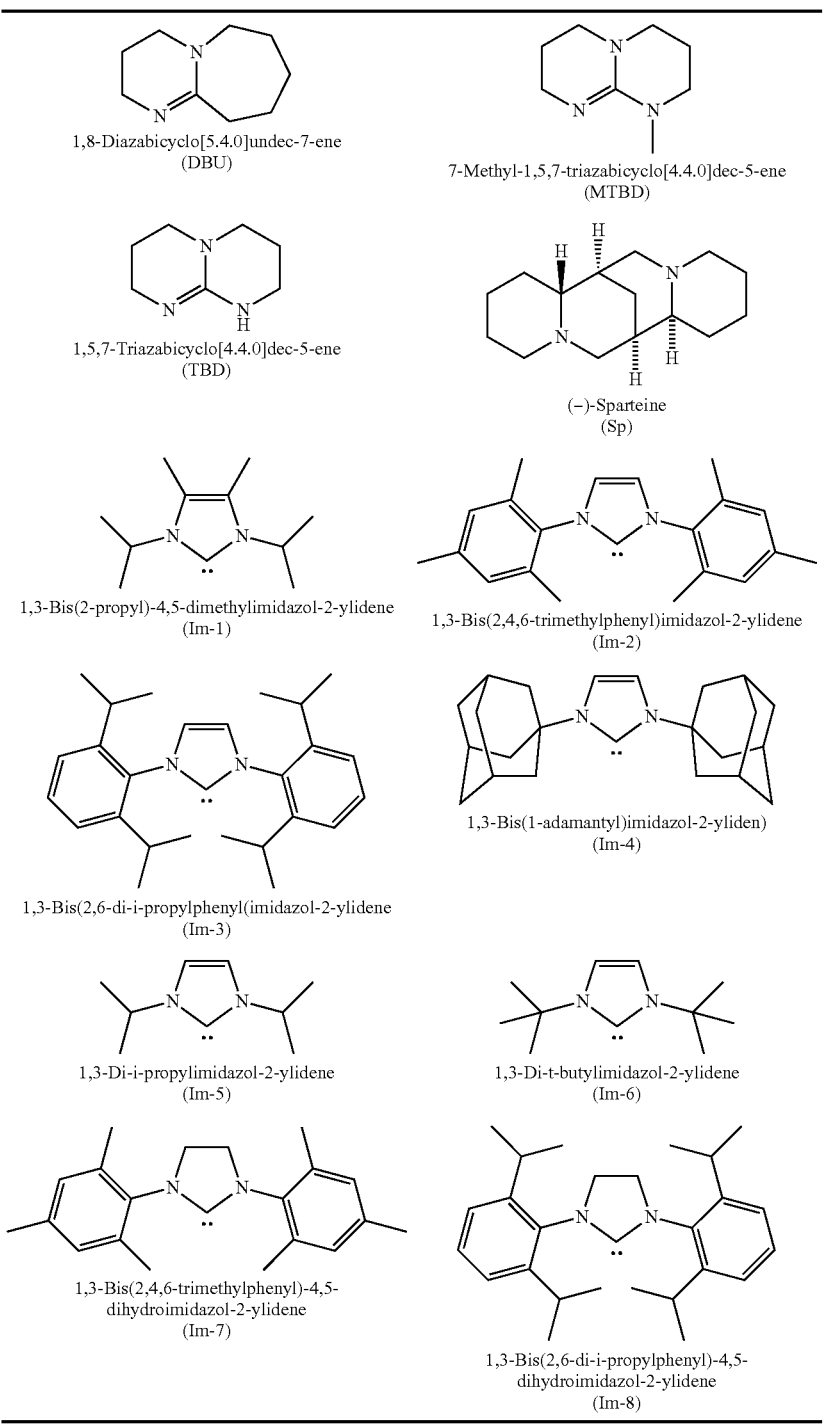

In an embodiment, the accelerator has two or three nitrogens, each capable of participating as a Lewis base, as for example in the structure (−)-sparteine. Stronger bases generally improve the polymerization rate.

The ring-opening polymerization can be performed with or without the use of a solvent, more particularly with a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable cyclic carbonyl monomer concentration is about 0.1 to 5 moles per liter, and more particularly about 0.2 to 4 moles per liter. In a specific embodiment, the reaction mixture for the ring-opening polymerization is free of a solvent.

The ring-opening polymerization can be performed at a temperature that is about ambient temperature or higher, more specifically a temperature from 15° C. to 200° C., and more particularly 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

Whether performed in solution or in bulk, the polymerizations are conducted in an inert (i.e., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

The nitrogen base accelerator is present in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of polyether alcohol initiator is calculated based on the equivalent molecular weight per hydroxyl group in the alcohol initiator. The hydroxyl groups are present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05× 50=2.5 g per mole of monomer.

In a specific embodiment, the catalyst is present in an amount of about 0.2 to 20 mol %, the nitrogen base accelerator is present in an amount of 0.1 to 5.0 mol %, and the hydroxyl groups of the initiator are present in an amount of 0.1 to 5.0 mol % based on the equivalent molecular weight per hydroxyl group in the initiator.

As stated above, the ring opening polymerization forms an initial hydrophobic block comprising a living polymer segment. In an embodiment, one backbone repeating unit of the hydrophobic block is a carbonate repeating unit. As stated above, the hydrophobic block can itself comprise one or more block segments, wherein each block segment can independently comprise, for example, a backbone comprising a polyester homopolymer, a random polyester copolymer, a polycarbonate homopolymer, a random polycarbonate copolymer, or a random polyestercarbonate copolymer. The hydrophobic block can comprise a terminal hydroxyl group, terminal thiol group, or terminal amine group, each of which can initiate ROP chain growth. In some circumstances it can be desirable to endcap the initial hydrophobic block to prevent further chain growth and/or otherwise stabilize the backbone, forming an endcapped hydrophobic block. Endcapping materials and techniques are well established in polymer chemistry. These include, for example converting terminal hydroxyl groups to esters by treating the hydroxyl-terminated first polymer with an acid anhydride, acid chloride, or reactive ester to form the precursor polymer. In an embodiment, the hydrophobic block is treated with acetic anhydride, and the chains are endcapped with acetyl groups.

The block copolymer comprising the hydrophilic and hydrophobic blocks can have a number average molecular weight $M_n$ as determined by size exclusion chromatography of at least 2500 g/mol, more specifically 4000 g/mol to 150000 g/mol, and even more specifically 10000 g/mol to 50000 g/mol. In an embodiment, the block copolymer has a number average molecular weight $M_n$ of 10000 to 20000 g/mole. The block copolymer also has a narrow polydispersity index (PDI), generally from 1.01 to 1.35, more particularly 1.1 to 1.30, and even more particularly 1.1 to 1.25.

The catalysts can be removed by selective precipitation or in the case of the solid supported catalysts, simply by filtration. The block copolymer can comprise residual catalyst in an amount greater than 0 wt. %, based on total weight of the first polymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the first polymer and the residual catalyst.

The initial or endcapped hydrophobic block can comprise a latent carboxylic acid group, such as a protected carboxylic acid in the form of a benzyl ester. In this instance, the initial or endcapped hydrophobic block can be deprotected using H/Pd—C to form a deprotected hydrophobic block comprising pendant carboxylic acid groups. If the protected carboxylic acid is in the form of a thermally labile carboxylic ester, such as a t-butyl ester, the initial or endcapped hydrophobic block can be heated to form a deprotected hydrophobic block. If the protected carboxylic acid is hydrolytically unstable, such as a trifluoroethyl ester, the initial or endcapped hydrophobic block can be deprotected with mild aqueous acid or base to form a deprotected hydrophobic block. In a particular embodiment, the protected carboxylic acid is a benzyl ester.

Also disclosed is a method of forming a biodegradable, amphiphilic block polymer. The method comprises forming a block copolymer by ring opening polymerization of a first cyclic carbonyl monomer initiated by a polyether alcohol, wherein the block copolymer comprises a hydrophilic and a hydrophobic block, the hydrophobic block derived from the polyether alcohol, and the hydrophobic block comprising a first repeat unit comprising a side chain comprising a functional group selected from the group consisting of urea groups, carboxylic acid groups, and mixtures thereof. The hydrophobic block comprises no side chain comprising a covalently bound biologically active material, and the block copolymer forms micelles in water suitable for sequestering a biologically active material by a non-covalent interaction. In an embodiment, the first repeat unit is derived from MTCU. The method can further comprise derivatizing the end unit of the hydrophilic block, wherein the derivatized end unit comprises a moiety capable of interacting with a specific cell type. The derivatized end unit can, for example, comprise a galactose moiety for interacting with liver cells. The method can further comprise converting any side chain latent carboxylic acid group of the hydrophobic block to a carboxylic acid, such as by hydrogenation of the latent carboxylic acid using a suitable catalyst.

A more specific method of preparing a biodegradable, amphiphilic block copolymer comprises forming a reaction mixture comprising a first cyclic carbonyl monomer, a catalyst, an accelerator, a polyether alcohol initiator, and an optional solvent, wherein a first cyclic carbonyl monomer comprises a pendant moiety comprising a urea group; forming an initial hydrophobic block of the amphiphilic block copolymer by ring-opening polymerization of the one or more cyclic carbonyl monomers; optionally endcapping the hydrophobic block; derivatizing an end unit of the hydrophilic block, thereby forming a derivatized end unit comprising a biologically active moiety, and optionally deprotecting any protected carboxylic acid group of the hydrophobic block to form the amphiphilic block copolymer. In an embodiment, the polyether alcohol initiator is a mono-alcohol derived from poly(ethylene glycol) and/or polypropylene glycol). The hydrophobic block comprises no side chain comprising a covalently bound biologically active material, and the block copolymer forms micelles in water suitable for sequestering a biologically active material by a non-covalent interaction. In another embodiment, forming an initial hydrophobic block of the amphiphilic block copolymer is conducted by sequential ring-opening polymerization of the first cyclic carbonyl monomer and a second cyclic carbonyl monomer, thereby forming a hydrophobic block comprising a core block copolymer, the core block copolymer comprising a first core block linked to the hydrophilic block, the first core block comprising the first repeat unit, and a second core block linked to the first core block, the second core block comprising a second repeat unit derived from the second carbonyl monomer.

The amphiphilic block copolymers can comprise from 1 to 250 mmoles carboxylic acid per gram of block copolymer, more particularly more than 3 to 50 mmoles carboxylic acid per gram of block copolymer, and even more particularly 3 to 40 mmoles carboxylic acid per gram of block copolymer. The amphiphilic block copolymers can comprise 1 to 250 mmoles of a urea functional group per gram of block copolymer, more particularly 3 to 50 mmoles of a urea functional group per gram of block copolymer, and even more particularly 3 to 40 mmoles of a urea functional group per gram of block copolymer.

In aqueous solution the amphiphilic block copolymers self-assemble, forming micelles having an average particle size of from 10 nm to 500 nm, 10 nm to 250 nm, and more particularly 50 nm to 200 nm, 50 nm to 150 nm, 50 nm to 120 nm, and even more particularly from 50 nm to 100 nm, as measured by dynamic light scattering (Brookhaven Instrument Corp., Holtsville, N.Y., U.S.A.) equipped with a He—Ne laser beam at 658 nm (scattering angle: 90°). The particle size measurements are repeated for 5 runs for each sample, and the particle size are reported as the average of 5 readings. For the foregoing particle sizes, the aqueous solution can have a pH of from 5.0 to 8.0.

The amphiphilic block copolymers have a critical micelle concentration (CMC) of 0.01 to 300 mg/liter, more particularly 0.1 to 200 mg/liter, and even more particularly 0.1 to 100 mg/liter. The micelles can comprise one or more amphiphilic block copolymers prepared by any of the above-described methods. In an embodiment the micelles exhibit a cytoxicity of from 0% to 15%, 0% to 10%, 0% to 5%, or more particularly 0% to 1%.

The micelles can be mixed micelles comprising a biodegradable, biocompatible second block copolymer, wherein the second block copolymer comprises a second hydrophilic block derived from a second polyether alcohol, and a second hydrophobic block derived by ring opening polymerization of a second cyclic carbonyl monomer initiated by the second polyether alcohol; and wherein no side chain of the second hydrophobic block comprises a covalently bound biologically active material. In an embodiment, the second block copolymer comprises a second hydrophobic block comprising a side chain carboxylic acid group. In another embodiment, the carboxylic acid group of the hydrophobic block is derived by ring opening polymerization of a cyclic carbonyl compound comprising a benzyl ester, followed by hydrogenation of the benzyl ester with a suitable catalyst.

The amphiphilic block copolymers form loaded micelles with biologically active cargo materials, such as a gene, a nucleotide, a protein, a peptide, a drug, or combinations thereof. In aqueous solution at a pH of from 5.0 to 8.0, the micelles have an average particle size of from 10 nm to 500 nm, 10 nm to 250 nm, and more particularly 50 nm to 200 nm, 50 nm to 150 nm, 50 nm to 120 nm, and even more particularly from 50 nm to 100 nm, as measured by dynamic light scattering (Brookhaven Instrument Corp., Holtsville, N.Y., U.S.A.) equipped with a He—Ne laser beam at 658 nm (scattering angle: 90°). The particle size measurements are repeated for 5 runs for each sample, and the particle size are reported as the average of 5 readings. The loaded micelles can comprise, for example 0.1 to 90 wt. %, more particularly 5 to 50 wt. %, and even more particularly 15 to 50 wt. % of a biologically active material based on total dry weight of the loaded micelles. The micelles can comprise one or more amphiphilic block copolymers prepared using the above-described methods. In an embodiment, the biologically active cargo material is a drug.

Also disclosed is a method of preparing a loaded micelle for treating a cell, comprising contacting a first aqueous mixture comprising a biodegradable biocompatible block copolymer with a second aqueous mixture comprising a biologically active cargo material, to form a third mixture comprising the loaded micelle; wherein the loaded micelle has a particle size of 10 nm to 500 nm at a pH of from 5.0 to 8.0. The biodegradable, biocompatible block copolymer comprises a hydrophilic block derived from a polyether alcohol; and a hydrophobic block comprising a first repeat unit derived by ring opening polymerization of a first cyclic carbonyl monomer initiated by the polyether alcohol, the first repeat unit comprising a side chain comprising a functional group selected from the group consisting of urea groups, carboxylic acid groups, and mixtures thereof; wherein no side chain of the hydrophobic block comprises a covalently bound biologically active material; and wherein the block copolymer is suitable for sequestering a biologically active material by a non-covalent interaction. In an embodiment the hydrophilic block comprises a derivatized end unit comprising a moiety capable of interacting with a specific cell type. In another embodiment, the derivatized end unit comprises a galactose moiety or a mannose moiety. In another embodiment, the biologically active cargo material is doxorubicin.

Further disclosed is a method of treating a cell, comprising contacting the cell with an aqueous mixture comprising nanoparticles of a loaded micelle, the loaded micelle comprising a biodegradable, biocompatible first block copolymer, the first block copolymer comprising a hydrophilic block derived from a polyether alcohol, and a hydrophobic block comprising a first repeat unit derived by ring opening polymerization of a first cyclic carbonyl monomer initiated by the polyether alcohol, wherein the first repeat unit comprises a side chain comprising a functional group selected from the group consisting of a urea group, a carboxylic acid group, and a mixture thereof; and a biologically active cargo material. The first block copolymer is suitable for sequestering the biologically active material by a non-covalent interaction, and no side chain of the hydrophobic block is covalently bound to the biologically active material. The hydrophilic block can optionally comprise a derivatized end unit comprising a moiety capable of interacting with a specific cell type. The biologically active cargo can comprise a single biologically active material or a mixture of biologically active materials. The biologically active cargo can be a drug, for example doxorubicin. The end unit of the polyether alcohol can comprise a moiety which selectively interacts with a specific cell type. In an embodiment, the end unit comprises a galactose moiety or a mannose moiety. Cells can be contacted in vitro, ex vivo, or in vivo. Contacting induces 0% to 20%, 0% to 15%, 0% to 10%, 0% to 5%, 0% to 2%, or more particularly 0% to 1% cytotoxicity. In an embodiment, contacting induces no cytotoxicity.

The types of drugs that can be delivered using the present amphiphilic block copolymers are numerous, and include both small molecular weight compounds in the size range from 100 daltons to about 1,000 daltons as well as larger macromolecular drugs, such as peptide and protein drugs in the size range from about 1,000 daltons to about 100,000 daltons, and beyond. Exemplary protein drugs include peptide hormones such as insulin, glucagon, parathyroid hormone, calcitonin, vasopression, renin, prolactin, growth hormone, the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, patelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other exemplary drugs include Aspirin, Diflunisal, Diclofenac, Aceclofenac, Acemetacin, Etodolac, Indometacin, Sulindac, Tolmetin, Ibuprofen, Carprofen, Fenbufen, Fenoprofen, Flurbiprofen, Ketoprofen, Ketorolac, Loxoprofen, Naproxen, Oxaprozin, Tiaprofenic acid, Suprofen, Mefenamic acid, Meclofenamic acid, Lumiracoxib, Oxyphenbutazone, Piroxicam, Lornoxicam, Meloxicam, and Tenoxicam. Steroidal Anti-Inflammatory Drugs include Hydrocortisone, Prednisone, Prednisolone, Methylprednisolone, Dexamethasone, Betamethasone, Triamcinolone, Beclometasone, Fludrocortisone acetate, and Aldosterone. Chemotherapeutic drugs include Doxorubicin and DNA alkylating Agents such as Melphalan, Chlorambucil, Dacarbazine, Temozolomide, and Streptozotocin. Antimetabolite drugs include Methotrexate, Pemetrexed, Raltitrexed, Tioguanine, Fludarabine, Pentostatin, Cladribine, Floxuridine, and Gemcitabine, Alkaloid drugs include Vincristine, Vinblastine, Vinorelbine, Vindesine, and Topoisomerase. Inhibitors include Etoposide, Teniposide, Irinotecan, and Topotecan. Taxanes include Paclitaxel and Docetaxel. Anticoagulants include Warfarin, Acenocoumarol, Phenprocoumon, Argatroban, and Ximelagatran.

Still other exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone ®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraprred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys ®, Thioguanine, Thioguanine Tabloid®, Thiophosphoamide, Thioplex®, Thiotepa, TICE ®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

No limitation is placed on the type of cell that can be treated with the above-described loaded micelles. In particular, the cells can be eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded micelles can be used as non-viral transfection vectors. The target gene is not limited to any particular type of target gene or nucleotide sequence. For example, the target gene can be a cellular gene, an endogenous gene, an oncogene, a transgene, or a viral gene including translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NF1, NF2, RB1, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

The biodegradable amphiphilic block copolymers produced by organocatalytic ring-opening polymerization provide an effective drug delivery system. The combination of biodegradable urea and/or carboxylic acid containing repeat units in the hydrophobic block provides versatility in tailoring the binding strength, and therefore release properties of the loaded micelles for biologically active materials of diverse size and functionality. The amphiphilic block copolymers can be used for delivery of small molecular drugs and proteins, and for simultaneous delivery of drugs and genes or drugs and proteins.

The preparation and use of micelles based on the above-described polymers is further illustrated by the following examples.

EXAMPLES

Materials

Purchased materials are listed in Table 5.

TABLE 5

| Material | Description | Company |
| --- | --- | --- |
| MPEG1 | Monomethyl Endcapped PEG ($M_n$ 5000) | Fluka |
| MPEG2 | Monomethyl Endcapped PEG ($M_n$ 2400) | Fluka |
| HS-PEG-OH | Mono-Thiol Terminated PEG, $M_n$ 3228 | Rapp, Germany |
| OCH-PEG-OH | Mono-Aldehyde Terminated PEG, $M_n$ 2000 | Polymersource, Canada |
| APG | p-Aminophenyl beta-D-Galactopyranoside | Sigma |
| NHS-PEG-OH | Mono-N-Hydroxysuccinimide Derivatized PEG, $M_n$ 2000 | Jenkem, USA |

Monomethyl PEG, having a number average molecular weight of 5000 g/mol (MPEG1) and 2400 g/mol (MPEG2), obtained from Fluka, was azeotropically distilled and recrystallized from toluene prior of use. Trimethylene carbonate (Bohringer-Ingelheim) was azeotropically distilled form toluene and recrystallized prior of use. Sparteine was distilled from calcium hydride prior of use. Benzoic acid, ethanolamine, and phenylisothiocyanate (all Aldrich) were used as received. Dry THF and $CH_2Cl_2$ were obtained by using a solvents drying system from Innovative.

N-(3,5-trifluoromethyl)phenyl-N'-cyclohexyl-thiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over CaH2, filtering, and removing solvent under vacuum.

Methods of Analysis.

1H-NMR spectra were obtained on a Bruker Avance 400 instrument at 400 MHz. Gel permeation chromatography (GPC) was performed in THF or chloroform using a Waters chromatograph equipped with four 5 micrometer Waters columns (300 mm×7.7 mm) connected in series with increasing pore size (10, 100, 1000, $10^5$, $10^6$ Å), a Waters 410 differential refractometer and a 996 photodiode array detector, and calibrated with polystyrene standards (750–$2 \times 10^6$ g mol$^{-1}$).

Preparation of Monomers

A particularly useful synthon for functional biodegradable monomers is the so-called MTC family of cyclic carbonate monomer derived from 2,2-bis(methylol)propionic acid (bisMPA). BisMPA provides a facile route to 5-methyl-5-carboxyl-1,3-dioxan-2-one (MTCOH) and derivative thereof, as shown in Scheme 1.

Scheme 1.

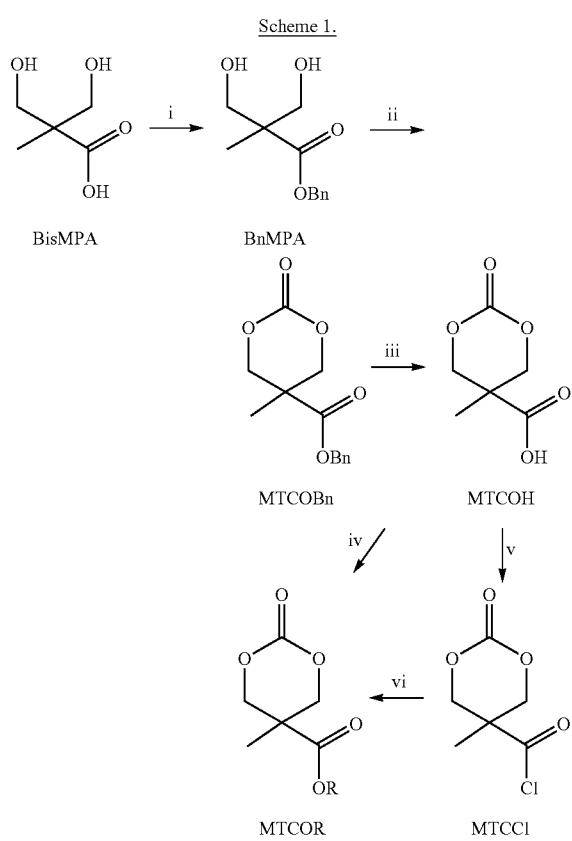

This approach parallels that of (meth)acrylate derivatization and has been demonstrated to create a wide selection of functional monomers capable of undergoing ring opening polymerization (ROP). In the example shown 2,2-Bis(methylol)propionic acid (BisMPA) is first converted (i) to a benzyl ester BnMPA, followed by reaction (ii) of BnMPA with triphosgene to form a cyclic carbonyl monomer, MTCOBn. MTCOBn is debenzylated (iii) to produce the cyclic carbonyl carboxylic acid, MTCOH. Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCCl followed by treatment (vi) of MTCCl with ROH in the presence of a base to form MTCOR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bis-MPA; (ii) triphosgene, pyridine, $CH_2Cl_2$, −78° C. to 0° C., 95% yield of MTCOBn; (iii) Pd/C (10%), $H_2$ (3 atm), EtOAc, room temperature, 24 hours, 99% yield of MTCOH; (iv) ROH, DCC, THF, room temperature, 1 to 24 hours; (v) $(COCl)_2$, THF, room temperature, 1 hour, 99% yield of MTCCl; (vi) ROH, $NEt_3$, RT, 3 hours yields MTCOR.

Using the above conditions MTCCl can be converted to a variety of cyclic carbonyl derivatives, including esters, by way of the BnMPA intermediate. Alternatively, as exemplified below, bisMPA can be esterified directly using another alcohol which can be ring closed using triphosgene to form the corresponding MTC ester (e.g., ethanol to form EtMPA).

Preparation of
5-methyl-5-benzyloxycarbonyl-1,3-dioxan-2-one
(MTCOBn)

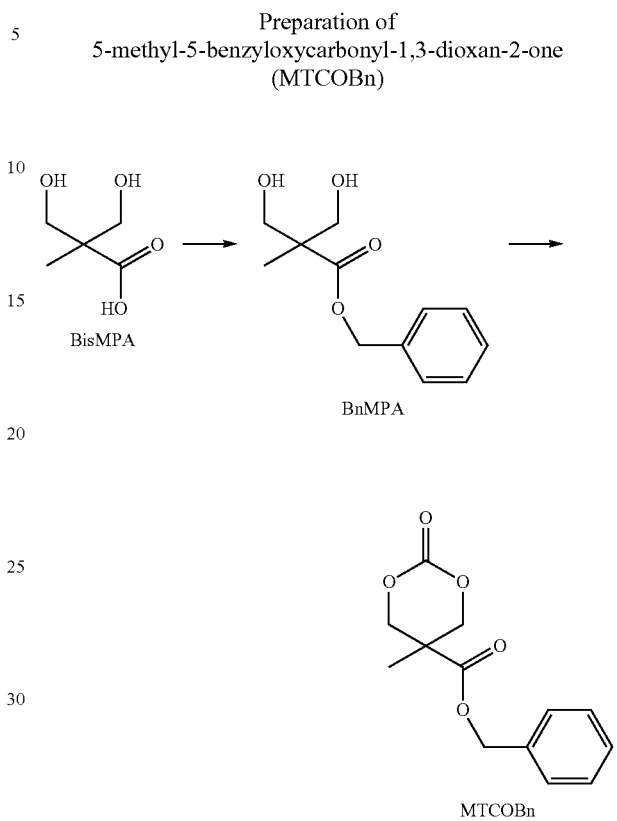

(i) A mixture of 2,2-bis(methylol)propionic acid (bisMPA) (18.0 g, 0.134 mol), KOH (85% assay; 8.9 g, 0.135 mol), and DMF (100 mL) was heated to 100° C. for 1 hour (the reaction mixture became a homogenous solution after 0.5 hour reaction). Benzyl bromide (27.6 g, 0.162 mol) was added to the warm solution under stirring, and the reaction was continued at 100° C. for 16 hours. The reaction mixture was cooled down and the solvent was removed under vacuum. Ethyl acetate (120 mL), hexanes (120 mL), and water (80 mL) were added to the residue. The organic layer was retained, washed with water (80 mL), dried over $MgSO_4$ and evaporated. The resulting solid was recrystallized from toluene (30 mL) to give pure benzyl 2,2-bis(methylol)propionate (BnMPA) (19.5 g, 65%). $^1$H NMR (400 MHz, $CDCl_3$, 22° C.): delta 7.38 (m, 5H, PhH), 5.19 (s, 2H, —$OCH_2$Ph), 3.94 (d, 2H, —$CH_2OH$), 3.73 (d, 2H, —$CH_2OH$), 1.12 (s, 3H, —$CH_3$).

(ii) Benzyl 2,2-bis(methylol)propionate (BnMPA) (11.2 g, 0.05 mol) was dissolved in $CH_2Cl_2$ (150 mL) and pyridine (25 mL, 0.3 mol) and the solution was chilled to −75° C. with dry ice/acetone under $N_2$ atmosphere. A solution of triphosgene (7.5 g, 25 mmol) in $CH_2Cl_2$ (150 mL) was added dropwise over 1 hours, and then the reaction mixture was allowed to warm to room temperature for 2 hours. The reaction was quenched by addition of saturated aqueous $NH_4Cl$ (75 mL), after which the organic layer was washed with 1 M aqueous HCl (3×100 mL), saturated aqueous $NaHCO_3$ (1×100 mL), dried over $MgSO_4$, filtered and evaporated. The resulting solid was recrystallized from ethyl acetate (15 mL) to give MTCOBn as a white solid (10.7 g, 86%). $^1$H NMR (400 MHz, $CDCl_3$, 22° C.): delta 7.37 (m, 5H, PhH), 5.20 (s, 2H, —OCH$_2$Ph), 4.69 (d, 2H, —CH$_2$OCOO), 4.23 (d, 2H, —CH$_2$OCOO), 1.31 (s, 3H, —CH$_3$).

Preparation of Phenylureaethanol (PUE)

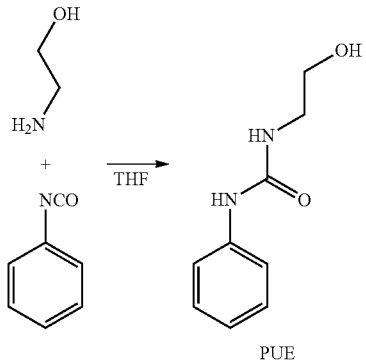

In a dry 100 mL round bottom flask equipped with a stir bar was charged ethanolamine (2.96 g, 48.5 mmol, 1 eq). Dry THF (30 mL) was added and the resulting solution cooled to 0° C. using an ice bath. A dropping funnel was attached in which phenylisocyanate (5.19 g, 4.74 mL, 43.6 mmol, 0.9 eq) and 30 mL of dry THF was charged. The resulting solution was added drop wise during a period of 30 minutes. The resulting solution was allowed to warm to ambient temperature and then left under stirring for an additional 16 hours. THF was removed through rotational evaporation the following morning. The crude product was recrystallized from ethyl acetate and then stirred rigorously for an additional 4 hours. The solids thus formed were removed by filtration, washed with further ethyl acetate and dried until a constant weight was reached, yield 7.0 g (~86%). $^1$H-NMR (DMSO-d6) delta: 8.59 (s, 1H, NH), 7.39 (d, 2H, ArH), 7.21 (t, 2H, ArH), 6.95 (t, 1H, ArH), 6.10 (t, 1H, NH), 4.78 (t, 1H, OH), 3.43 (q, 2H, CH$_2$), 3.17 (q, 2H, CH$_2$).

Preparation of MTCU

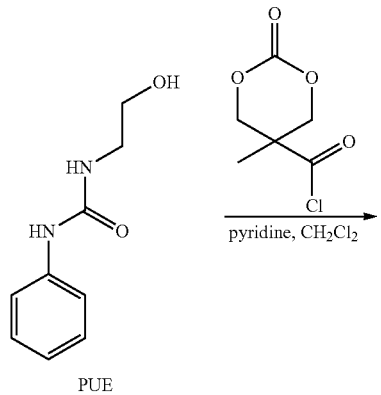

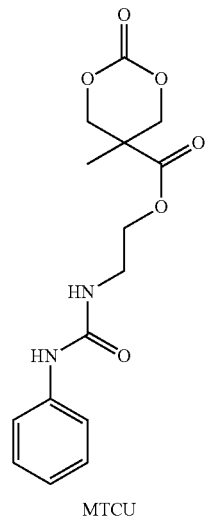

MTCOH (3.04 g, 19 mmol) was initially converted to MTCCl using the above described conditions with oxalyl chloride. The formed intermediate was dissolved in 50 mL of dry methylene chloride and charged in an addition funnel. In a dry 500 mL round bottom flask equipped with a stir bar was charged phenylureaethanol (PUE) (4.10 g, 22.8 mmol), pyridine (1.81 g, 1.85 mL, 22.8 mmol) and dry methylene chloride (150 mL). The addition funnel was attached under nitrogen and the flask cooled to 0° C. using an ice bath. The MTCCl solution was added drop wise during a period of 30 minutes and the solution allowed an additional 30 minutes under stirring. The ice bath was removed and the solution allowed to gently heat to ambient temperature and left under stirring for an additional 16 hours. The crude product was purified by column chromatography the following morning using silica gel. Ethyl acetate/hexane (1/1) was initially used as eluent before gently increasing the polarity and finishing with ethyl acetate. The product fractions were collected and the solvent removed through rotational evaporation. The isolated product was dried under vacuum until a constant weight was used yielding 6.0 g (~80%) of an off-white/slight yellow oil which crystallized upon standing. $^1$H-NMR (CDCl$_3$) delta: 7.39 (d, 2H, ArH), 7.25 (m, 3H, ArH), 7.02 (t, 1H, NH), 5.40 (t, 1H, NH), 4.68 (d, 2H, CH$_2$), 4.30 (t, 2H, CH$_2$), 4.20 (d, 2H, CH$_2$), 3.55 (t, 2H, CH$_2$), 1.30 (s, 3H, CH$_3$). HR-MS-ESI: m/z calculated for C$_{15}$H$_{18}$N$_2$O$_6$+Na 345.31 found 345.10.

Synthesis of Ethyl 2,2-bis(methylol)propionate (EtMPA)

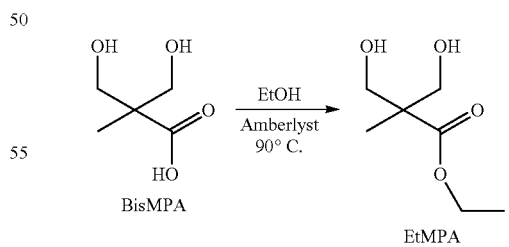

2,2-Bis(methylol)propionic acid (bisMPA; 22.1 g, 0.165 mol) was added in ethanol (150 mL) with Amberlyst-15 (6.8 g) and refluxed overnight. The resins were then filtered out and the filtrate was evaporated. Methylene chloride (200 mL) was added to the resulting viscous liquid to filtrate the unreacted reagent and byproduct. After the solution was dried over MgSO4 and evaporated, ethyl 2,2-bis(methylol)propionate (EtMPA) was obtained as a clear and colorless liquid (21.1 g, 86%).

Preparation of
5-methyl-5-ethyloxycarbonyl-1,3-dioxan-2-one
(MTCOEt)

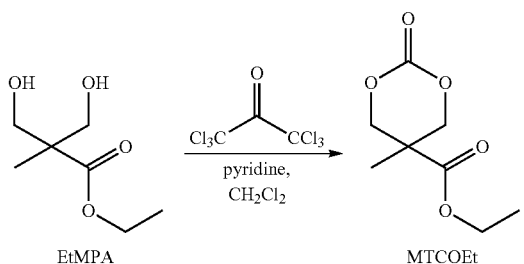

EtMPA          MTCOEt

A solution of triphosgene (19.5 g, 0.065 mol) in CH$_2$Cl$_2$ (200 mL) was added stepwise to a CH$_2$Cl$_2$ solution (150 mL) of ethyl 2,2-bis(methylol)propionate (MPAEt) (21.1 g, 0.131 mol) and pyridine (64 mL, 0.786 mol) over 30 min at −75° C. with dry ice/acetone. The reaction mixture was kept stirring for another 2 hours under chilled condition and then allowed to heat to room temperature. Saturated NH$_4$Cl aqueous solution (200 mL) was added to the reaction mixture to decompose excess triphosgene. The organic phase was then treated with 1 N HCl aq (200 mL), followed by saturated NaHCO$_3$ (200 mL), brine (200 mL), and water (200 mL). After the CH$_2$Cl$_2$ solution was dried over MgSO$_4$ and evaporated, the residue was recrystallized from ethylacetate to give white crystals (13.8 g, 56%). $^1$H NMR: delta 4.68 (d, 2H, CH$_2$OCOO), 4.25 (q, 1H, OCH$_2$CH$_3$), 4.19 (d, 2H, CH$_2$OCOO), 1.32 (s, 3H, CH$_3$), 1.29 (t, 3H, CH$_3$CH$_2$O). $^{13}$C NMR: delta 171.0, 147.5, 72.9, 62.1, 39.9, 17.3, 13.8. HR-ESI-MS: m/z calcd for C$_8$H$_{12}$O$_5$.Na, 211.0582; found, 221.0578.

I. Carboxylic Acid Containing Block Copolymers

Examples 1 to 4 and Comparative Example 1 (CEx. 1)

Protected Carboxylic Acid Containing Block Copolymers

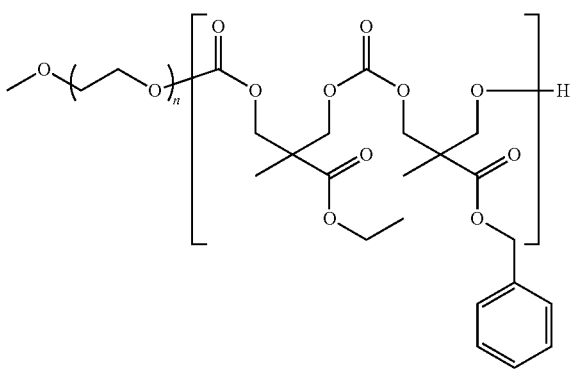

Two cyclic carbonyl monomers, MTCOBn and MTCOEt, were selected as building blocks because they are biocompatible, easily prepared in high yield and able to introduce a pendant carboxylic acid and ethyl ester group to the block copolymers, respectively. The living ROP of MTCOBn, MTCOEt, or their mixture was carried out in CH$_2$Cl$_2$ with an organocatalyst initiated from a macroinitiator monomethyl endcapped poly(ethylene glycol) (M$_n$ 2,400 g/mol, PDI 1.04) (MPEG2). After surveying several organocatalysts for the ROP, 1,8-diazabicyclo[5.4.0]undec-7-ene (DBU) exhibited desirable catalytic performance. In the presence of DBU, both MTCOBn and MTCOEt showed almost the same polymerization rates, and they were completely polymerized in 2 hours. Thus, triblock copolymers (Examples 2 and 3), of which the two kinds of pendant functional groups are arranged in reverse block sequence in the polycarbonate segment, were constructed by stepwise ring opening polymerization. After exhausting one monomer in a 2 hour reaction, the other monomer was added to the reaction solution. The solution was stirred for another 2 hours until the reaction was complete. GPC monitoring experiments showed that the molecular weight (MW) increments of block copolymers at 2 hours and 4 hours were in good agreement with the monomer added in the feed, suggesting the successful formation of triblock copolymers Examples 2 and 3. Moreover, the same reaction rates also ensure the formation of block copolymer Example 4 bearing randomly distributed pendant functional groups in the polycarbonate segment. Finally, benzyl groups of block copolymers Examples 1 to 4 could be removed in the presence of Pd—C (10% w/w) under hydrogen gas atmosphere, giving the corresponding block copolymers 5 to 8, while hydrogenolysis of MTCOEt in Comparative Example 1 (CEx. 1) was not observed in this reaction. The compositions of block copolymers were quantitatively studied using $^1$H NMR spectroscopy. A comparison between the integral intensities of the peaks for methylene groups of MPEG2 and those for the methyl groups of MTCOBn, MTCOEt, or both of them, gives the composition of block copolymers as listed in Table 6.

The procedure for ROP of the mixture of MTCOBn and MTCOEt (molar ratio 1:1) with MPEG2 to produce Example 4 is typical. A solution of MTCOBn (0.3 g, 1.2 mmol) in CH$_2$Cl$_2$ (0.75 mL) was mixed with the solution of MTCOEt (0.226 g, 1.2 mmol) in CH$_2$Cl$_2$ (0.75 mL), then the mixture was transferred to the solution of MPEG2 (0.144 g, 0.06 mmol) and DBU (9.2 mg, 0.06 mmol) in CH$_2$Cl$_2$ (0.75 mL) under stirring. After reacting for 4 hours, benzoic acid (5-10 mg) was added to quench the polymerization. The reaction mixture was then precipitated into diethyl ether (40 mL) and the precipitate was centrifuged and dried in vacuo. Finally, the crude product was purified by column chromatography on a Sephadex LH-20 column with THF as eluent, to give Example 4 as colorless viscous liquid (0.56 g, 84%).

Sequential ring opening polymerization of cyclic carbonyl monomers to form a hydrophobic block is illustrated by the preparation of Example 2, MPEG2$_{54}$-b-[P(MTCOBN)$_{20}$-b-P(MTCOEt)$_{19}$)]. The subscripts represent the numbers of the repeat units. Firstly, a solution of MTCOBn (0.3 g, 1.2 mmol) in CH$_2$Cl$_2$ (0.75 mL) was added to the solution of MPEG (0.144 g, 0.06 mmol) and DBU (9.2 mg, 0.06 mmol) in CH$_2$Cl$_2$ (0.75 mL) under stirring. After reacting for 2 hours, a solution of MTCOEt (0.226 g, 1.2 mmol) in CH$_2$Cl$_2$ (0.75 mL) was added. The reaction was continued for another 2 hours before benzoic acid was added to quench the reaction. Block copolymer Example 3, was synthesized using a similar procedure. The yields and analytical data for all five block copolymers are given below.

Example 1

MPEG2$_{54}$-b-[P(MTCOBn)$_{36}$], where the Subscripts Represent the Numbers of the Repeat Units

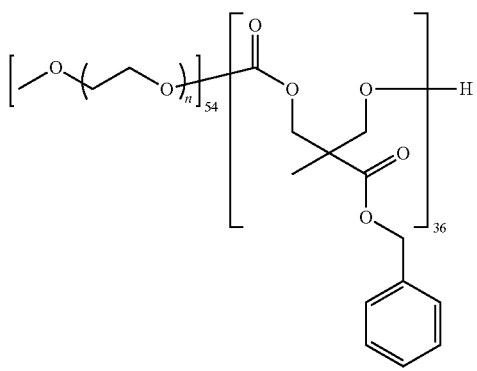

MPEG2$_{54}$-b-[P(MTCOBn)$_{36}$]

MPEG2$_{54}$-b-[P(MTCOBn)$_{36}$]

Yield, 82%. $^1$H NMR (400 MHz, CDCl$_3$, 22° C.): delta 7.29 (m, 180H, PhH), 5.12 (s, 72H, —OCH$_2$Ph), 4.27 (m, 139H, —CH$_2$OCOO), 3.63 (m, 217H, H of MPEG), 1.22 (s, 108H, —CH$_3$).

Example 2

MPEG2$_{54}$-b-[P(MTCOBn)$_{20}$-b-(MTCOEt)$_{19}$], where the Subscripts Represent the Numbers of the Repeat Units

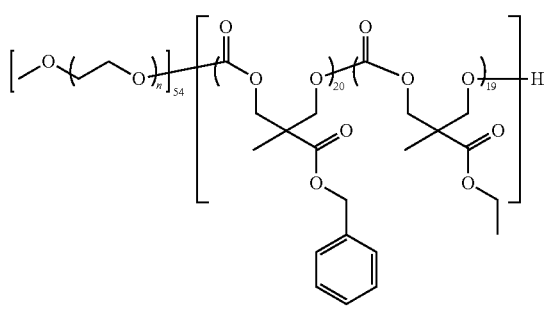

MPEG2$_{54}$-b-[P(MTCOBn)$_{20}$-b-(MTCOEt)$_{19}$]

MPEG2$_{54}$-b-[P(MTCOBn)$_{20}$-b-(MTCOEt)$_{19}$]

Yield, 86%. $^1$H NMR (400 MHz, CDCl$_3$, 22° C.): delta 7.29 (m, 100H, PhH), 5.12 (s, 40H, —OCH$_2$Ph), 4.27 (m, 190H, —CH$_2$OCOO and —OCH$_2$CH$_3$), 3.63 (m, 219H, H of MPEG), 1.23 (m, 174H, —CH$_3$ and —OCH$_2$CH$_3$).

Example 3

MPEG2$_{54}$-b-[P(MTCOEt)$_{18}$-b-P(MTCOBn)$_{19}$], where the Subscripts Represent the Numbers of the Repeat Units

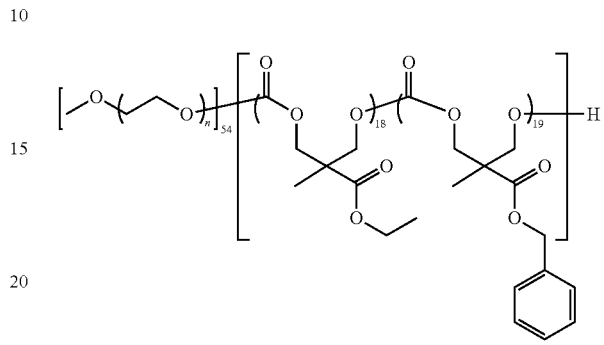

MPEG2$_{54}$-b-[P(MTCOEt)$_{18}$-b-P(MTCOBn)$_{19}$]

MPEG2$_{54}$-b-[P(MTCOEt)$_{18}$-b-P(MTCOBm)$_{19}$]

Yield, 84%. $^1$H NMR (400 MHz, CDCl$_3$, 22° C.): delta 7.28 (m, 95H, PhH), 5.11 (s, 35H, —OCH$_2$Ph), 4.21 (m, 182H, —CH$_2$OCOO and —OCH$_2$CH$_3$), 3.64 (m, 214H, H of MPEG), 1.21 (m, 165H, —CH$_3$ and —OCH$_2$CH$_3$).

Example 4

MPEG2$_{54}$-b-[P(MTCOEt$_{17}$-r-MTCOBn$_{17}$)], where the Subscripts Represent the Numbers of the Repeat Units

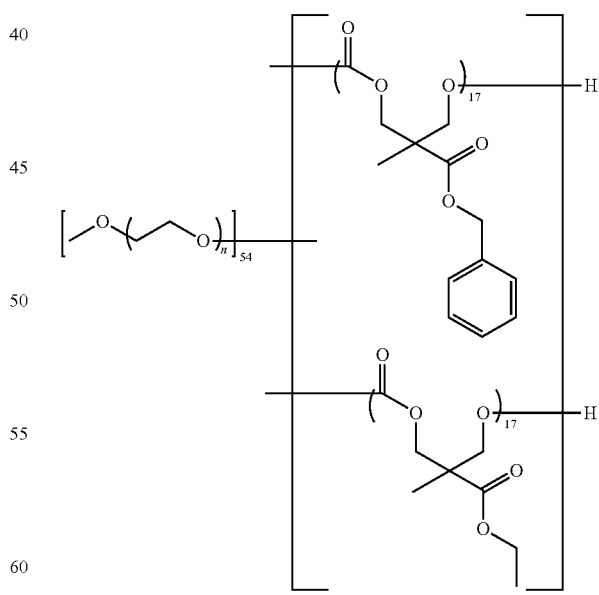

MPEG2$_{54}$-b-[P(MTCOEt$_{17}$-r-MTCOBn$_{17}$)]

MPEG2$_{54}$-b-[P(MTCOEt$_{17}$-r-MTCOBn$_{17}$)]

Yield, 84%. $^1$H NMR (400 MHz, CDCl$_3$, 22° C.): delta 7.31 (m, 85H, PhH), 5.14 (s, 34H, —OCH$_2$Ph), 4.27 (m, 167H, —CH$_2$OCOO and —OCH$_2$CH$_3$), 3.65 (m, 218H, H of MPEG), 1.22 (s, 153H, —CH$_3$ and —OCH$_2$CH$_3$).

CEx-1

MPEG2$_{54}$-b-[P(MTCOEt)$_{35}$], where the Subscripts Represent the Numbers of the Repeat Units

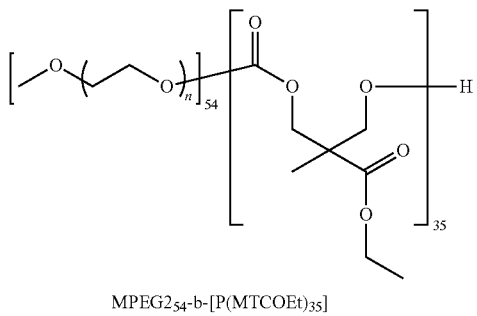

MPEG2$_{54}$-b-[P(MTCOEt)$_{35}$]

MPEG2$_{54}$-b-[P(MTCOEt)$_{35}$]
Yield, 85%. $^1$H NMR (400 MHz, CDCl$_3$, 22° C.): delta 4.20 (m, 206H, —CH$_2$OCOO and —OCH$_2$CH$_3$), 3.65 (m, 214H, H of MPEG), 1.25 (s, 210H, —CH$_3$ and —OCH$_2$CH$_3$).

Example 9

MPEG1$_{113}$-b-[P(MTCOBn)$_5$-b-P(MTCOEt)$_9$]

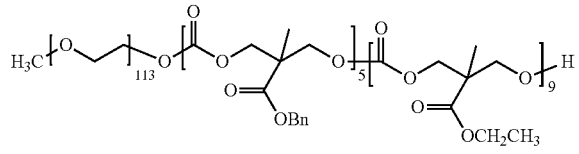

MPEG1$_{113}$-b-[P(MTCOBn)$_5$-b-P(MTCOEt)$_9$]

MPEG1$_{113}$-b-[P(MTCOBn)$_5$-b-P(MTCOEt)$_9$]
This polymer was prepared as described above for Example 2. A solution of MTCOBn (0.075 g, 0.3 mmol) in CH$_2$Cl$_2$ (0.75 mL) was added to a solution of MPEG1 (0.3 g, 0.06 mmol) and DBU (9.2 mg, 0.06 mmol) in CH$_2$Cl$_2$ (0.75 mL) under stirring. After 2 hours, a solution of MTCOEt (0.113 g, 0.6 mmol) in CH$_2$Cl$_2$ (0.75 mL) was added. The reaction was continued for another 2 hours before benzoic acid was added to quench the reaction. The reaction mixture was then precipitated into diethyl ether (40 mL) and the precipitate was centrifuged and dried in vacuo. Finally, the crude product was purified by column chromatography on a Sephadex LH-20 column with THF as eluent, to give the product as colorless viscous liquid (0.46 g, 84%).

Example 10

MPEG1$_{113}$-b-[P(MTCOH)$_5$-b-P(MTCOEt)$_9$]

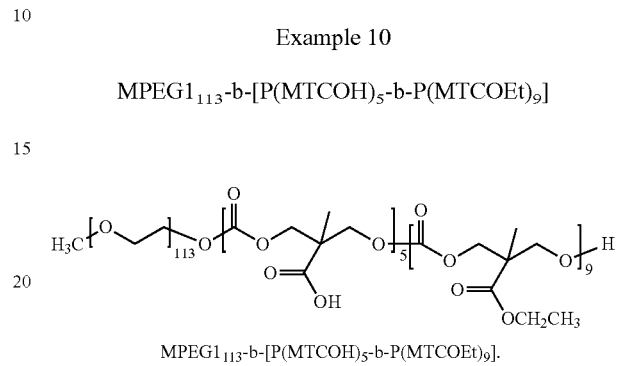

MPEG1$_{113}$-b-[P(MTCOH)$_5$-b-P(MTCOEt)$_9$].

MPEG1$_{113}$-b-[P(MTCOH)$_5$-b-P(MTCOEt)$_9$].
This block polymer was prepared as described above for Example 5 to 8. A mixture of the product from Example 9, THF (7.5 mL), methanol (7.5 mL), and Pd—C (10% w/w, 0.2 g) was swirled under H$_2$ (7 atm) overnight. After evacuation of the H$_2$ atmosphere, the mixture was filtered through THF-wetted Celite. Additional THF (15 mL) and methanol (15 mL) were used to ensure complete transfer. The collected washings were evaporated, and the residue was purified by column chromatography on a Sephadex LH-20 column with THF as eluent, to give the final product as colorless viscous liquid. The yield was more than 90%, and $^1$H NMR spectra showed that the protected groups were removed after hydrogenation. $^1$H NMR (400 MHz, CDCl$_3$, 22° C.): delta 4.16 (m, 74H, —CH$_2$OCOO and —OCH$_2$CH$_3$), 3.47 (m, 452H, H of MPEG), 1.14 (s, 69H, —CH$_3$ and —OCH$_2$CH$_3$).

The utility of the DBU catalytic system was demonstrated through the synthesis of narrowly dispersed initial block copolymers having predictable molecular weights. Table 6 summarizes the molecular characteristics of the initial block copolymers Examples 1 to 4, 9, and CEx. 1 estimated from $^1$H NMR spectra and GPC analysis, before deprotecting the benzyl ester. Subscripts correspond to the number of repeat units.

TABLE 6

| Block Copolymers | Type of Hydrophobic Block | Block Copolymer Composition[a,c] | $M_n$[b] | $M_w/M_n$[b] |
| --- | --- | --- | --- | --- |
| Example 1 | Homopolymer | MPEG2$_{54}$-b-[P(MTCOBn)$_{36}$] | 11,490 | 1.20 |
| Example 2 | Block Copolymer | MPEG2$_{54}$-b-[P(MTCOBn)$_{20}$-b-P(MTCOEt)$_{19}$] | 11,060 | 1.16 |
| Example 3 | Block Copolymer | MPEG2$_{54}$-b-[P(MTCOEt)$_{18}$-b-P(MTCOBn)$_{19}$] | 10,950 | 1.17 |
| Example 4 | Random Copolymer | MPEG2$_{54}$-b-[P(MTCOEt$_{17}$-r-MTCOBn$_{17}$)] | 9,970 | 1.15 |
| CEx. 1 | Homopolymer | MPEG2$_{54}$-b-[P(MTCOEt)$_{35}$] | 8,810 | 1.14 |
| Example 9 (for preparation of mixed micelles) | Block Copolymer | MPEG1$_{113}$-b-[P(MTCOBn)$_5$-b-P(MTCOEt)$_9$] | 9,962 | 1.10 |

[a]Determined from $^1$H NMR spectra;
[b]Obtained from gel permeation chromatography (GPC) measurement.
[c]MPEG2 = monomethyl PEG ($M_n$ = 2400 g/mol)

The GPC data for the polymers in Table 6 show that the initial block copolymers presented a single unimodal peak in their GPC chromotograms. The polymers were found to be nearly monodispersed, with MW varying from 8,810 to 11,490 and a narrow polydispersity ranging from 1.14 to 1.20. The compositions of the initial block copolymers estimated from $^1$H NMR spectra are well matched with the molecular weight values from GPC results, and they were also consistent with the feed ratio.

Examples 5 to 8, and 10

Hydrogenation Of Examples 1 to 4, and 9. Carboxylic Acid Containing Block Copolymers The general procedure for hydrogenation of the protected carboxylic acid containing block copolymers, Examples 1-4, is as follows. The protected block copolymer containing pendant benzyl ester (0.5 g), THF (7.5 mL), methanol (7.5 mL), and Pd—C (10% w/w, 0.2 g) were combined and swirled under $H_2$ (7 atm) overnight. After evacuation of the $H_2$ atmosphere, the mixture was filtered through THF-wetted Celite. Additional THF (15 mL) and methanol (15 mL) were used to ensure complete transfer. The collected washings were evaporated, and the residue was purified by column chromatography on a Sephadex LH-20 column with THF as eluent, to give Examples 5 to 8 as colorless viscous liquid. The structures are the same as shown above for Examples 1 to 4, except the benzyl ester is a carboxylic acid. The yield was more than 90%.

Figure 1B:
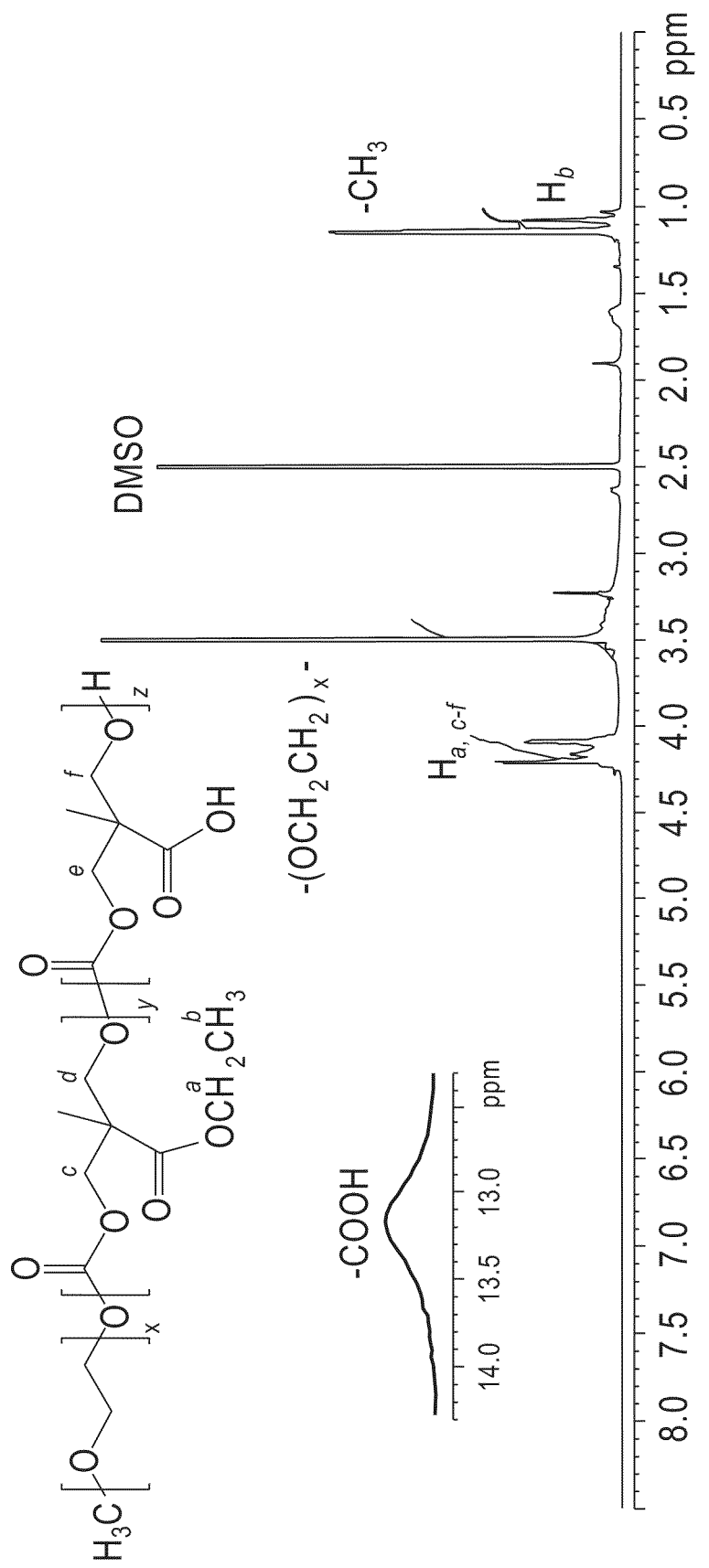
FIG. 1B is a $^1$H NMR spectrum of Example 3 after hydrogenolysis of the benzyl ester group to a carboxylic acid.

$^1$H NMR spectra show that the protected groups were removed after hydrogenation. For example, FIG. 1A is a $^1$H NMR spectrum of protected block copolymer Example 3 in $CDCl_3$, and FIG. 1B is a $^1$H NMR spectrum of the corresponding deprotected block copolymer Example 7 in DMSO-$d_6$. Compared with FIG. 1A, the disappearance of the peaks at 7.28 and 5.11 ppm in FIG. 1B indicates that the protecting benzyl group was cleanly removed by hydrogenolysis. The peak at 13.18 ppm is attributed to the proton of free carboxylic acid, providing direct evidence for deprotection of the repeating unit derived from MTCOBn.

Preparation of Blank and Loaded Micelles Using Examples 5 to 8, 10 and CEx. 1

Micelles Preparation and Drug Loading Determination. Pure block copolymer micelles of Examples 5 to 8, 10 and CEx. 1 were prepared by directly dispersing polymer in water followed by sonication to facilitate micellization and aqueous dispersion of micelles. For doxorubicin (DOX) loaded micelles, DOX (5 mg) was dissolved in 1.5 mL of DMAc and neutralized with two moles excess triethylamine. The polymer solution, in which 10 mg of block copolymer was dissolved in 0.5 mL of DMAc, was added into the DOX solution and mixed by vortex for 5 min. The drug and polymer solution was added dropwise to DI water (10 mL) when being sonicated at 130 W using a probe-based sonicator (Vibra Cell VCX 130), and the sonication lasted for 2 min. The solution was then dialyzed against 1000 mL of DI water for 48 hours using a dialysis bag with molecular weight cut-off of 1000 Da (Spectra/Por 7, Spectrum Laboratories Inc.). The water was changed every 2 hours for the first 6 hours and once again the next day. After dialysis, the solution in the dialysis bag was filtered with 0.45 micrometer syringe filter. To determine DOX loading level, the above micelle solution was freeze-dried for two days, and then a known amount of DOX-loaded micelles was dissolved in 1 mL of DMSO. The DOX concentration was estimated by using the UV-VIS spectrophotometer at 480 nm. The drug loading was calculated based on the standard curve obtained from DOX in DMSO.

Fluorescence Measurement. Critical Micelle Concentration (CMC) of the polymers in deionized (DI) water was determined using pyrene as the probe. The fluorescence spectra were recorded by a LS 50B luminescence spectrometer (Perkin Elmer, U.S.A.) at room temperatures. Samples were equilibrated for 10 min before any measurements were made. Aliquots of pyrene in acetone solution ($6.16 \times 10^{-5}$ M, 10 microliters) were added to containers and the acetone was left to evaporate. Polymer solutions (1 mL) at varying concentrations were added into the containers and left to equilibrate for 24 hours. The final pyrene concentration in each sample was $6.16 \times 10^{-7}$ M. The emission spectra were scanned from 360 to 410 nm at an excitation wavelength of 339 nm while the excitation spectra were scanned from 300 to 360 nm at an emission wavelength of 395 nm. Both the excitation and emission bandwidths were set at 2.5 nm. The intensity (peak height) ratios of $I_{336}/I_{334}$ from the excitation spectra were analyzed as a function of polymer concentration. The CMC was taken from the intersection between the tangent to the curve at the inflection and tangent of the points at low concentrations.

Dynamic light scattering. The particle size of the freshly prepared blank and DOX-loaded micelles from Examples 5 to 8, 10 and CEx. 1 was measured using dynamic light scattering (ZetaPALS, Brookhaven Instrument Corporation, USA) at a scatting angle of 90° after filtration with a 0.45 micrometer syringe filter. Each measurement was repeated 5 times. An average value was obtained from the five measurements. Multimodel analysis was chosen to conduct the size measurements to maximize the resolution as the samples might contain individual micelles and aggregates.

The critical micellization concentration (CMC) values and particle size measurements of blank and DOX-loaded micelles obtained for Examples 5 to 8, 10 and CEx. 1 are listed in Table 7.

TABLE 7

|  | Composition | CMC value (mg/L) | Hydrodynamic diameter (nm) | PDI | DOX loading level (%)[a] |
| --- | --- | --- | --- | --- | --- |
| Example 5 | $MPEG2_{54}$-b-[P(MTCOH)$_{36}$] | 152.8 | 165 | 0.28 | 23.7 |
| Example 6 | $MPEG2_{54}$-b-[P(MTCOH)$_{20}$-b-P(MTCOEt)$_{19}$] | 14.3 | 53 | 0.26 | 42.1 |
| Example 7 | $MPEG2_{54}$-b-[P(MTCOEt)$_{18}$-b-P(MTCOH)$_{19}$] | 5.2 | 47 | 0.24 | 43.1 |
| Example 8 | $MPEG2_{54}$-b-[P(MTCOEt$_{17}$-r-MTCOH$_{17}$)] | 58.5 | 123 | 0.20 | 38.3 |
| CEx. 1 | $MPEG2_{54}$-b-[P(MTCOEt)$_{35}$] | 0.52 | 146 | 0.29 | 2.2 |

TABLE 7-continued

| Composition | CMC value (mg/L) | Hydrodynamic diameter (nm) | PDI | DOX loading level (%)[a] |
|---|---|---|---|---|
| Example 10[a] MPEG1-b-[P(MTCOH)$_5$-b-P(MTCOEt)$_9$] | 28.2 | 83.1 (after drug loading: 69.6) | 0.21 (after drug loading) | 30.1 |

[a]Example 10 was used below for preparation of mixed micelles

As shown in Table 7, Examples 5 to 8, and 10 have low CMC values, but the values varied from 5.2 to 152.8 mg/L, strongly depending on the pendant functional group distribution in the hydrophobic polycarbonate block. The micellar structure of block copolymers is mainly divided into hydrophilic MPEG2 shell and hydrophobic polycarbonate core. Example 5 presented the highest CMC because its polycarbonate core is a homopolymer of MTCOH. The pendant carboxylic acid groups could form hydrogen bonds with surrounding water molecules, increasing the solubility of hydrophobic block in water and reducing its hydrophobicity at the same time. Examples 6 and 7 are triblock copolymers comprising two kinds of pendant functional groups arranged in block sequence within the hydrophobic block. In their micellar structure, the hydrophobic core is also divided into an outer core made of a less hydrophobic polycarbonate block with pendant carboxylic acid groups, and an inner core made of a more hydrophobic polycarbonate block with pendant ethyl ester groups. Their well-defined core-shell structure led to the lowest CMC among the block copolymers. Similarly, the randomly distributed pendant functional groups in the polycarbonate segment of Example 8 reduced the hydrophobicity of micellar core, resulting in a higher CMC than Examples 6 to 7. Low CMC is an important parameter of micelles since the dissociation of micelles in the blood post administration may cause rapid release of the enclosed drug, leading to a severe in vivo side effect.

A trend similar to the CMC results was also observed with the hydrodynamic diameters of DOX-loaded micelles measured by dynamic light scattering (DLS) (Table 7). The particle size and uniformity are important factors for the drug-loaded micelles since physical properties strongly depend on both of them. Table 7 shows the particle size of doxorubicin (DOX) loaded micelles made from block copolymer Examples 5 to 8 ranged from 47 to 165 nm, with a relatively narrow size distribution varying from 0.2 to 0.28. The small particle size of the micelles enables them to be less susceptible to clearance by the reticuloendothelial systems (RES). The smallest hydrodynamic diameters of Examples 6 to 7 can be attributed to their well-defined micellar structure. Examples 5 to 8 also exhibited larger particle size than Examples 6 and 7. Without being bound by theory, the larger particle size is attributed to the hydrophilic pendant carboxylic acid groups in the core being accessible to the external environment, interacting with surrounding water molecules and reducing the hydrophobicity of the polycarbonate segment, resulting in the loose-packing of the micellar cores. The dilution effect of the hydrophobic ethyl ester groups on the carboxylic acid groups in the Example 8 micelle core makes its particle size smaller than that of Example 5. The direct observation of the structure of DOX-loaded micelles was carried out using transmission electron microscopy (TEM).

Figure 2:
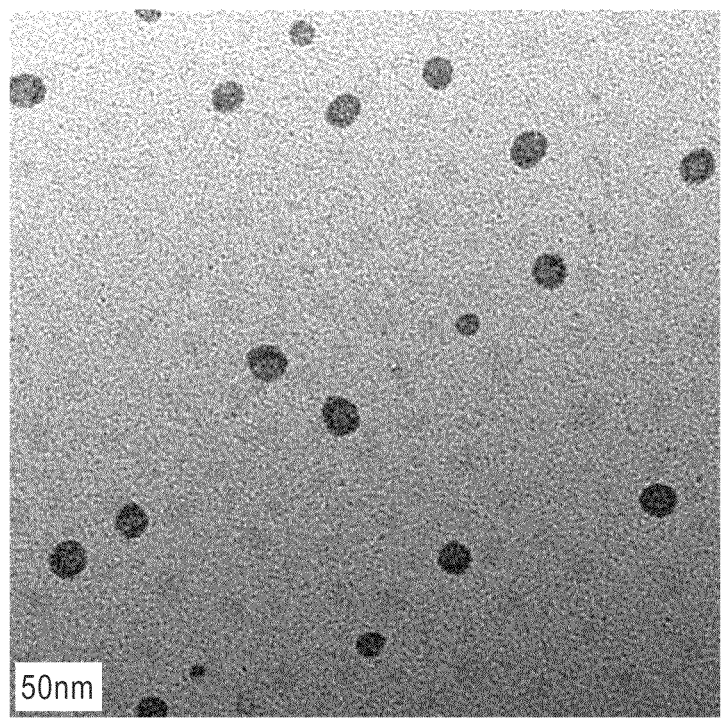
FIG. 2 is a transmission electron micrograph (TEM) image of DOX-loaded micelles made from triblock copolymer Example 7.

FIG. 2 is a transmission electron micrograph (TEM) image of DOX-loaded micelles made from triblock copolymer Example 7. The micelles take an almost spherical shape, and most of the loaded micelles have diameters in the range of 32 to 45 nm in the dry state, which is slightly lower than the corresponding hydrodynamic diameters. This result may be attributed to the collapse of the free hydrophilic segments of the copolymer as well as dehydration of the polymer chain.

In addition, the DOX-loaded micelles fabricated from block copolymers Examples 5 to 8 showed significantly high drug loading level and encapsulation efficiency. As listed in Table 7, the drug loading level of Examples 5 to 8 ranged from 23.7 wt. % to 43.1 wt. % based on weight of the dry block copolymer compared to 2.2 wt. % for CEx 1.

The encapsulation of DOX into the block copolymer micelles was performed through a sonication/membrane dialysis method. Due to the removal of large particles by filtration, DOX-loaded micelles prepared with block copolymer Examples 5 and 8 showed lower drug loading levels. Examples 6 and 7 showed more than 40 wt. % drug loading levels. Since the high drug loading level could be attributed to the electrostatic interaction between DOX and the pendant carboxylic acid groups of block copolymers, it appears that introduction of the pendant ethyl ester groups using MTCOEt for the ring opening polymerization does not significantly affect the binding capacity of the carboxylic acid groups to DOX.

In Vitro Drug Release Studies of DOX Loaded Micelles Formed with Examples 5 to 8 and CEx 1.

The freshly prepared DOX-loaded micelles solutions (3 mL) were transferred to dialysis membrane tubes with MWCO of 1,000 Da (Spectra/Por 7, Spectrum Laboratories Inc.). The tubes were then immersed in a beaker containing 50 mL of PBS buffer (pH 7.4), which were shaken at a speed of 100 rev/min, and incubated at 37° C. At specific time intervals, 1 mL of solutions were withdrawn from the release medium and replaced with fresh PBS buffer. The DOX content in the samples was analyzed using the UV-VIS spectrophotometer at 480 nm, and calculated based on the standard curve obtained from DOX in H2O.

Figure 3:
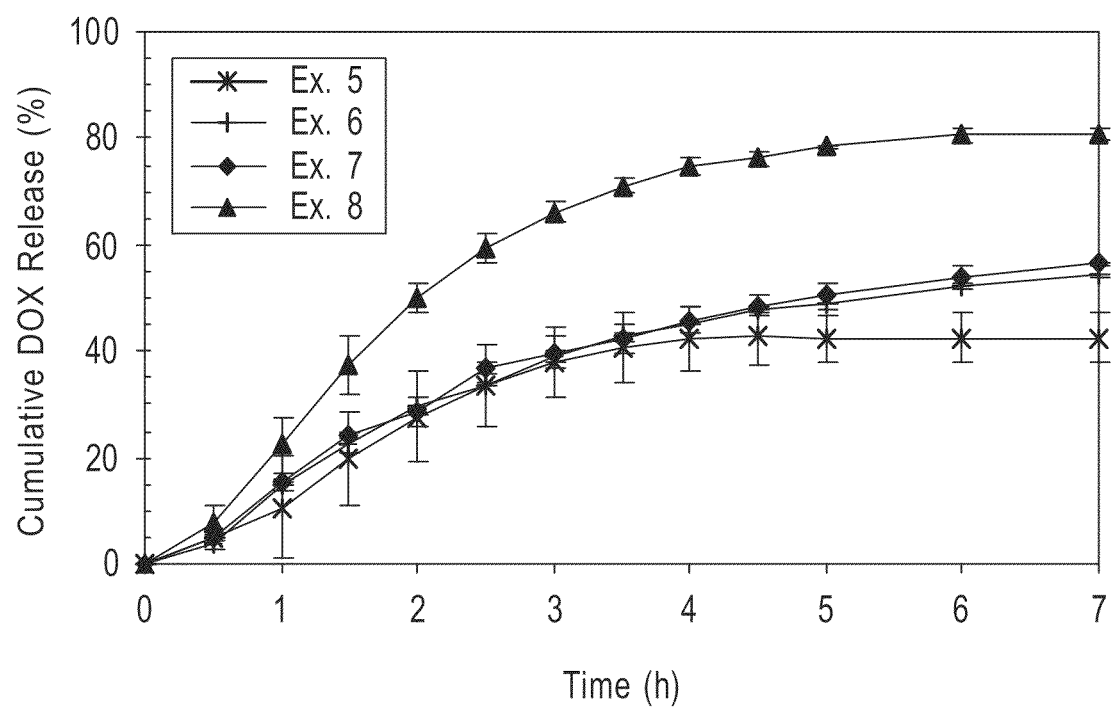
FIG. 3 is a graph showing the DOX release profiles of Examples 5 to 8.

The release profiles of DOX are shown in FIG. 3. For all the micelles, no obvious initial burst release was observed. In contrast to approximately 55% of DOX released from micelles formed with Examples 6 and 7, more than 80% of the drug released from micelles formed with Example 8 within 7 hours. This is probably due to loosely-packed micellar core. Moreover, the randomly distributed carboxylic acid groups in the core are well separated and diluted by the ethyl ester groups, reducing the intramolecular hydrogen bonding between neighboring carboxylic acid groups and making the micelle core accessible to the external aqueous environment. Micelles formed with Example 5 showed the slowest drug release profile, with only 42% of DOX released after 7 hours due to the strong electrostatic attraction between DOX and the pendant carboxylic acid groups.

Cytotoxicity of DOX Loaded Micelles Formed with Examples 5 to 8.

Figure 4A:
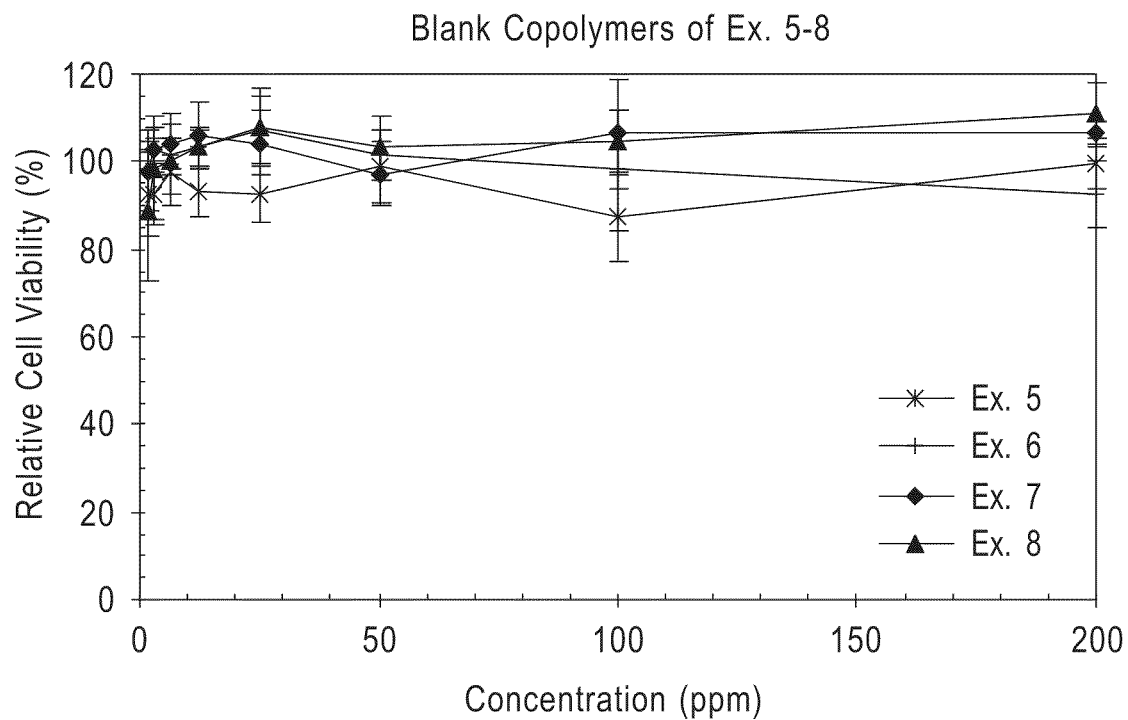
FIG. 4A is a graph showing the viability of the HepG2 cells as a function of concentration of blank micelles formed with polymer Examples 5 to 8.
Figure 4B:
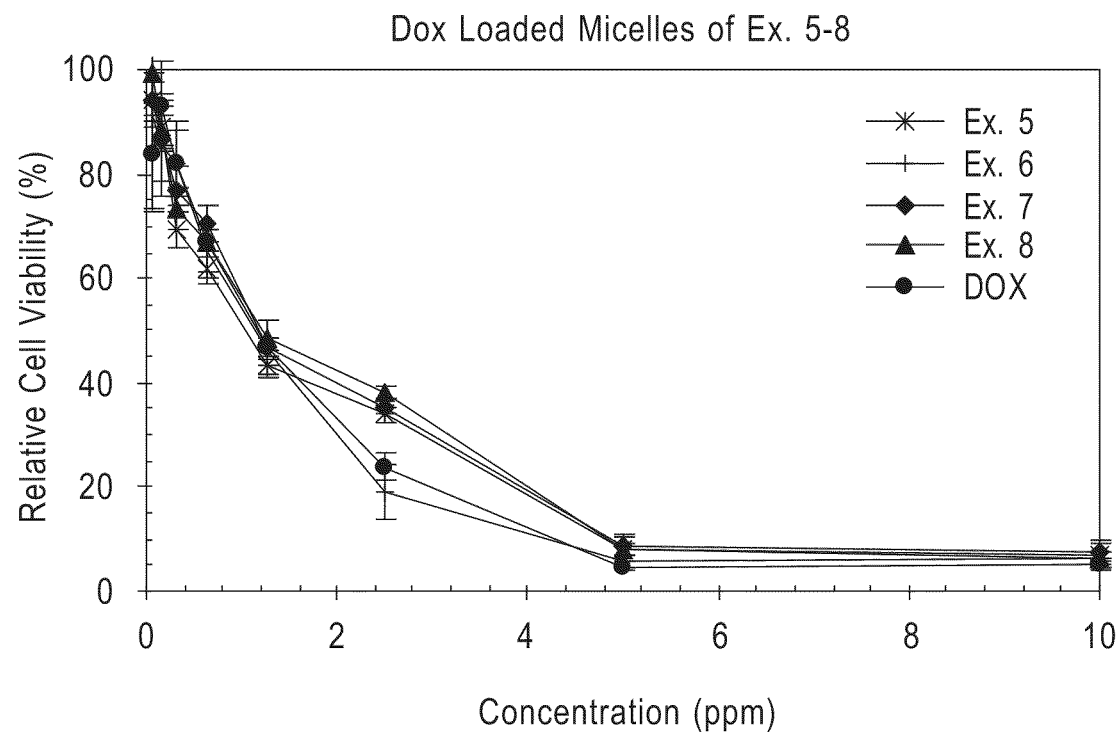
FIG. 4B is a graph showing the viability of the HepG2 cells as a function of concentration of the DOX loaded micelles formed with polymer Examples 5 to 8.

The cytotoxicity study of DOX-loaded micelles formed from Examples 5-8 and blank copolymers (Examples 5 to 8) was performed using HepG2 cells in comparison with free DOX. The cultured cells were exposed to the blank copolymers and no significant cytotoxicity was observed up to 200 mg/L after 48 hours at 37° C. FIG. 4A is a graph showing the viability of the HepG2 cells as a function of concentration of the blank polymer Examples 5 to 8. FIG. 4B is a graph showing the viability of the HepG2 cells as a function of concentration of the loaded micelles of Examples 5 to 8 and DOX. The DOX-loaded micelles presented a strongly dose-dependent effect on cytotoxicity, and the cell viability profiles of the micelles is quite similar to that of free DOX. The $IC_{50}$ value of free DOX in HepG2 was 1.14 mg/L, the same with those of the micelles made from block copolymers Examples 5 to 8.

II. Preparation of Urea Containing Block Copolymers

Scheme 2 illustrates the synthesis Poly(ethylene glycol)-block-poly(MTCOEt-random-MTCU) copolymers represented by the formula MPEG1-b-[P(MTCOEt-r-MTCU)].

Scheme 2.

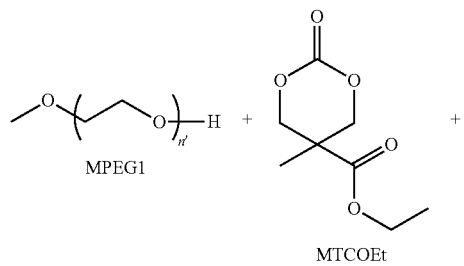

MPEG1

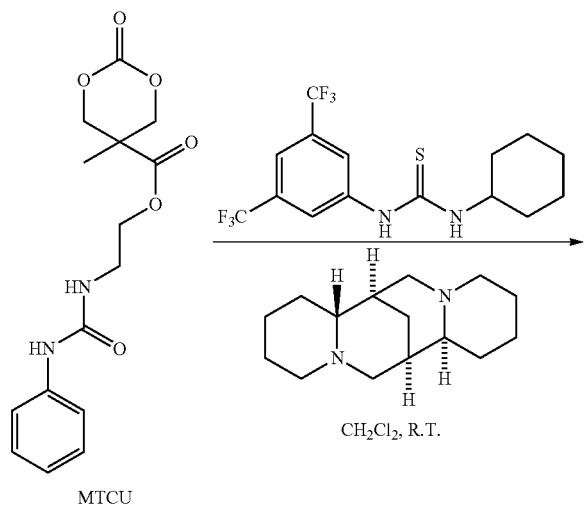

MTCU

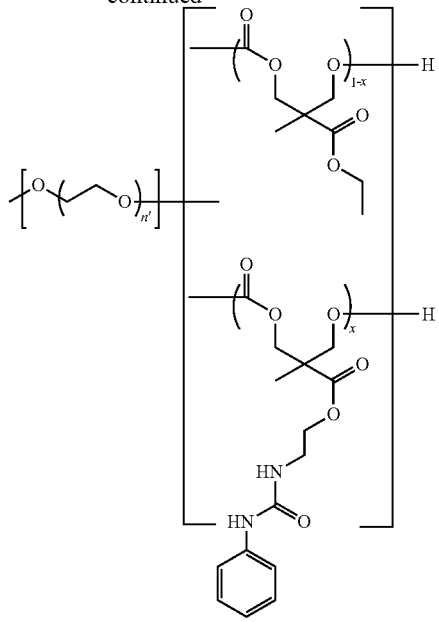

MPEG1-b-[P(MTCOEt$_{1-x}$-r-MTCU$_x$)]

Block copolymers were prepared by ring-opening polymerization of different amounts of cyclic monomers MTCOEt and MTCU to form a random polycarbonate chain, using monomethylether-PEG (5,000 g/mol) (MPEG1) as a macroinitiator, and TU/sparteine as the catalyst. The subscript n' is the number of repeat units in the commercial MPEG1. The content of urea in the block copolymers was controlled by changing the feed ratios of the MTCOEt and MTCU monomers. The subscript x is the mole fraction of each cyclic carbonyl monomer, where the sum of the mole fractions equals 1. The ring-opening of cyclic monomers was performed in a glove box using thiourea and tertiary amine catalysts designed for bifunctional activation of both monomer and alcohol through hydrogen bonding.

Examples 11 to 14 and CEx. 2-5

Figure 5:
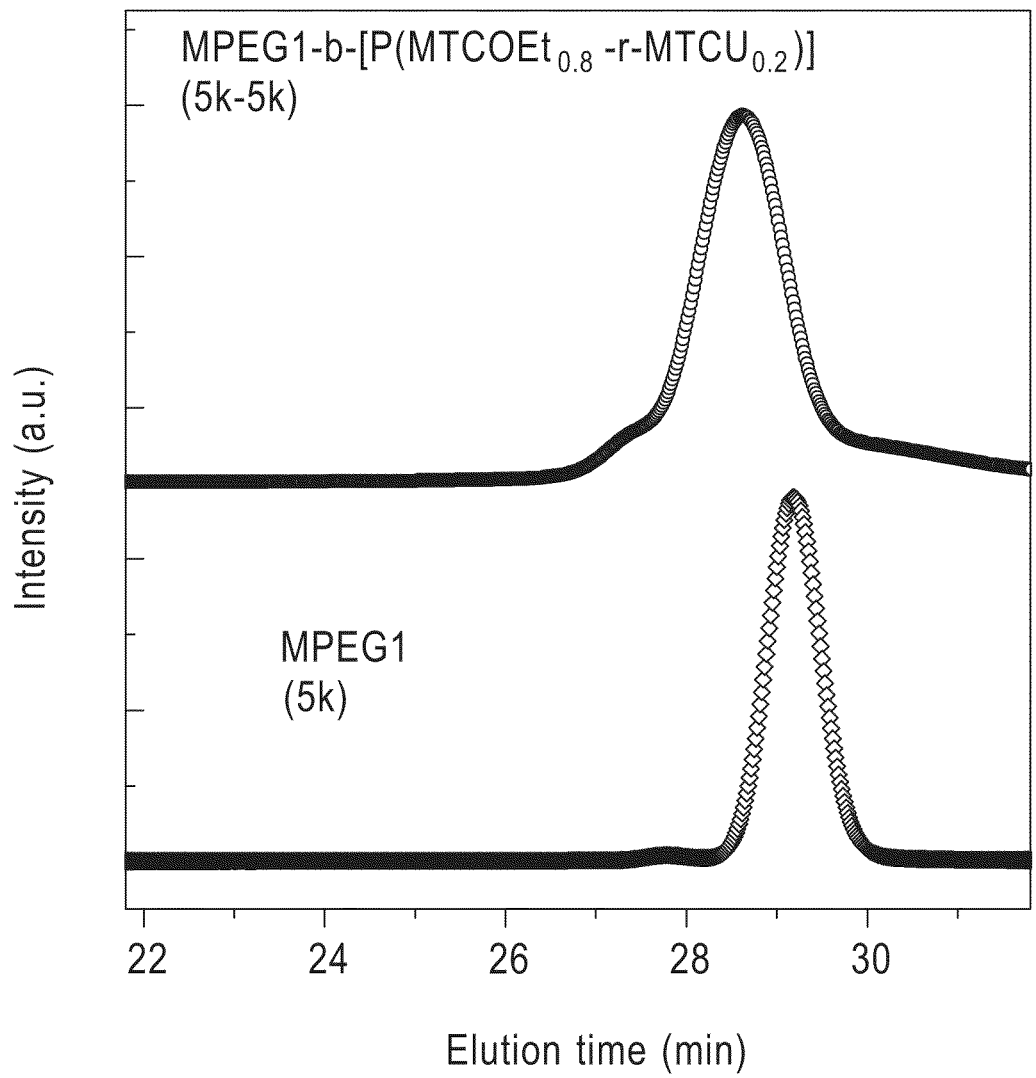
FIG. 5 is a GPC chromatogram comparing Example 11, MPEG1-b-[P(MTCOEt$_{0.8}$-r-MTCU$_{0.2}$)] (5 k-5 k), with monomethyl PEG, MPEG1 (5 k).

The following preparation of Example 11, MPEG1-b-[P(MTCOEt$_{0.8}$-r-MTCU$_{0.2}$)] (5 k-5 k) is representative. In a glove box, thiourea catalyst (TU) (37 mg, 0.1 mmol), sparteine (24 mg, 0.1 mmol), and MPEG1 (0.5 g, 0.1 mmol) was charged in a dry 20 mL glass vial equipped with a stir bar. A small volume of methylene chloride was added and the formed solution kept under stirring for 10 minutes. MTCOEt (0.35 g, 1.86 mmol) and MTCU (0.15 g, 0.47 mmol) were added with additional methylene chloride (for a total concentration of 1M to monomer) and the resulting solution kept under stirring for 16 hours. At the end of ring opening polymerization reaction determined from $^1$H NMR, benzoic acid (15 mg, 0.12 mmol) was added to quench the catalyst and the crude polymer was precipitated in 500 mL of cold diethyl-ether. The non-solvent was gently allowed to warm to ambient temperature after which the supernatant was decanted. The off-white solids were collected and dried under vacuum until a constant weight was reached. Yield 0.75 g (75%). $^1$H-NMR (CDCl$_3$) delta: 7.38 (m, 2H, polyMTC(MTCU)-ArH), 7.22 (m, 3H, polyMTC(MTCU)-ArH), 6.95 (t, 1H, polyMTC(MTCU)-NH), 4.30 (br, m, 4H, polyMTC(MTCU and MTCOEt)-CH$_2$, 2H, polyMTC(MTCU)-CH$_2$), 4.10 (m, 2H, polyMTC(MTCOEt)-CH$_2$CH$_3$), 3.68 (s, 4H, PEG), 3.38 (s, 3H, a-end), 1.38 (br, m, 3H, polyMTC(MTCU and MTCOEt)-CH$_3$; 3H, polyMTC(MTCOEt)-CH$_2$CH$_3$) (see Figure S1). GPC (THF, PS standard): PDI=1.11. FIG. 5 is a GPC chromatogram comparing Example 11, MPEG1-b-[P(MTCOEt$_{0.8}$-r-MTCU$_{0.2}$)] (5 k-5 k), with monomethyl end-capped PEG, MPEG1 (5 k).

Comparative example 2 (CEx. 2) was also prepared from MPEG1 and MTCOEt using the above procedure, having a structure similar to CEx. 1 except that the MPEG1 had twice the molecular weight of MPEG2. Several additional comparative examples CEx. 3-5, each a poly(ethylene glycol)-block-poly(trimethylene carbonate) block copolymer, were prepared from MPEG1 and TMC using the above-described procedures, and are referenced by the formula MPEG1-b-[P(TMC)].

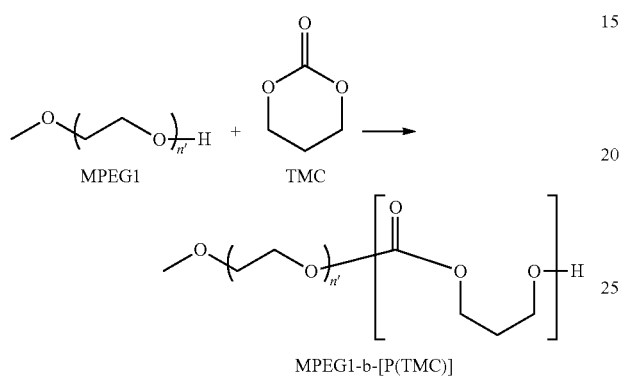

MPEG1-b-[P(TMC)]

Each of CEx. 2 to 5 lack a hydrogen bonding urea group. CEx. 3 to 5 differ in the molecular weight of the hydrophobic block derived from TMC.

Examples 15

MPEG1$_{113}$-b-[P(MTCOBn)$_4$-r-P(MTCU)$_5$]

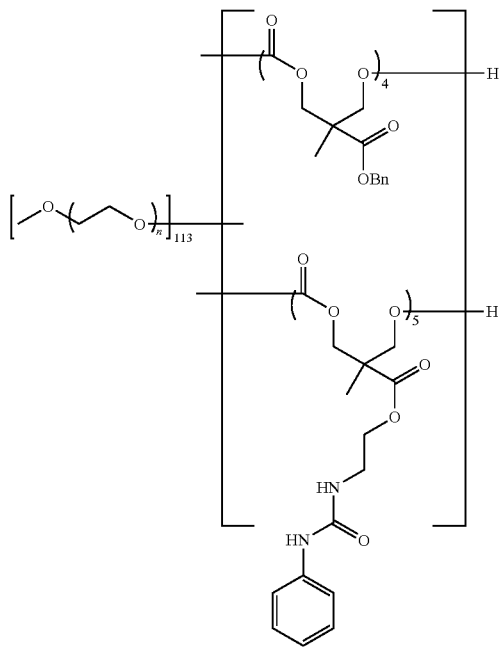

A solution of MTCOBn (0.085 g, 0.3375 mmol) in CH$_2$Cl$_2$ (0.75 mL) was mixed with the solution of MTCU (0.1087 g, 0.3375 mmol) in CH$_2$Cl$_2$ (1 mL), then the mixture was transferred to the solution of MPEG1 (0.225 g, 0.045 mmol), TU (16.65 mg, 0.045 mmol) and sparteine (10.35 microliters, 0.045 mmol) in CH$_2$Cl$_2$ (1 mL) under stirring. After reacting overnight, benzoic acid (20 mg) was added to quench the polymerization. The reaction mixture was then precipitated into diethyl ether (40 mL) and the precipitate was centrifuged and dried in vacuo. Finally, the crude product was purified by column chromatography on a Sephadex LH-20 column with THF as eluent, to give product as white viscous solid (0.33 g, 80%). Yield, 80%. $^1$H NMR (400 MHz, CDCl$_3$, 22° C.): delta 7.45 (s, 10H, PhH), 7.18 (s, 10H, PhH), 6.83 (s, 5H, PhH), 4.06-4.23 (br, m, 46H, —CH$_2$OCOO, —OCH$_2$CH$_3$, and —COOCH$_2$CH$_2$NH— of polyMTCU), 3.48 (m, 462H, H of MPEG and —COOCH$_2$CH$_2$NH— of polyMTCU), 1.12 (m, 27H, —CH$_3$).

Example 16

MPEG1$_{113}$-b-[P(MTCOH)$_4$-r-P(MTCU)$_5$]

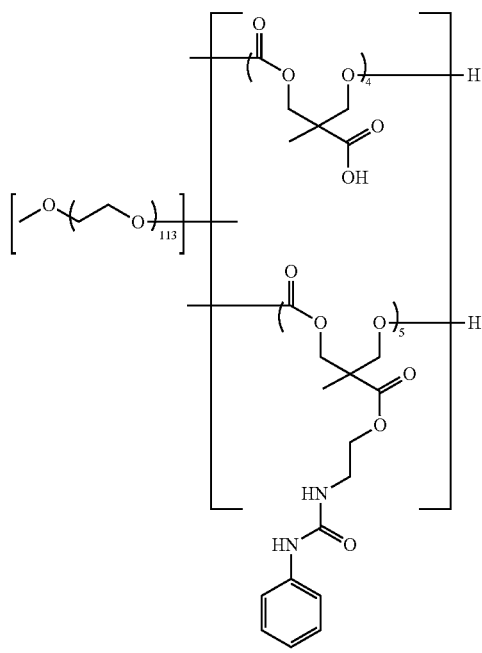

A mixture of the above product from Example 15, THF (7.5 mL), methanol (7.5 mL), and Pd—C (10% w/w, 0.2 g) was swirled under H$_2$ (7 atm) overnight. After evacuation of the H$_2$ atmosphere, the mixture was filtered through THF-wetted Celite. Additional THF (15 mL) and methanol (15 mL) were used to ensure complete transfer. The collected washings were evaporated, and the residue was purified by column chromatography on a Sephadex LH-20 column with THF as eluent, to give the final product as colorless viscous liquid. The yield was more than 90%, and $^1$H NMR spectra showed that the protected groups were removed after hydrogenation.

Fluorescence Measurement. Critical Micelle Concentration (CMC) of Examples 11 to 14 and CEx. 2 to 5 in deionized (DI) water was determined using pyrene as the probe. The fluorescence spectra were recorded by a LS 50B luminescence spectrometer (Perkin Elmer, U.S.A.) at room temperatures. Samples were equilibrated for 10 min before any measurements were made. Aliquots of pyrene in acetone solution ($6.16\times10^{-5}$ M, 10 μL) were added to containers and the acetone was left to evaporate. Polymer solutions (1 mL) at varying concentrations were added into the containers and left to equilibrate for 24 hours. The final pyrene concentration in each sample was $6.16\times10^{-7}$ M. The emission spectra were scanned from 360 to 410 nm at an excitation wavelength of 339 nm while the excitation spectra were scanned from 300 to 360 nm at an emission wavelength of 395 nm. Both the excitation and emission bandwidths were set at 2.5 nm. The intensity (peak height) ratios of $I_{336}/I_{334}$ from the excitation spectra were analyzed as a function of polymer concentration. The CMC was taken from the intersection between the tangent to the curve at the inflection and tangent of the points at low concentrations.

Dynamic light scattering (DLS). Dynamic light scattering (DLS) experiment was performed on a Brookhaven BI-200SM goniometer system (Brookhaven, U.S.A.) to determine the particle size ($D_h$) of micelles formed with Examples 9 to 12 and CEx. 2 to 5. The light source is a power adjustable vertically polarized 75 mW HeNe ion laser with a wavelength of 633 nm.

Table 8 summarizes the structures and characterization of the urea containing block copolymer Examples 11 to 14, 16 and CEx. 2 to 5. The number average molecular weight of the hydrophilic and hydrophobic blocks is shown in parentheses next to the sample formula. For example, in Example 12 the expression (5 k-3 k) means the hydrophilic block had a $M_n$ of 5000 and the hydrophobic block had a $M_n$ of 3000. The subscript after each monomer in the formula is the mole fraction of the cyclic carbonyl monomer in the hydrophobic block, where the sum of the mole fraction is 1.0. The hydrophobic block of Examples 11 to 14 comprise random copolymers of MTCOEt and MTCU.

TABLE 8

| Sample | | Block Copolymer Only | | | | | Loaded Micelle (Block Copolymer + Doxorubicin) | | Drug loading (wt %) |
|---|---|---|---|---|---|---|---|---|---|
| | | $M_n$ (g/mol)[a] | PDI[b] | $D_h$ (nm)[c] | PDI[c] | CMC (mg/L)[d] | $D_h$ (nm)[c] | PDI[c] | |
| Example 11 | MPEG1-b-[P(MTCOEt$_{0.8}$-r-MTCU$_{0.2}$)] (5k-5k) | 9610 | 1.11 | 44.0 | 0.105 | 3.5 | 158.2 | 0.125 | 10.5 ± 0.7 |
| Example 12 | MPEG1-b-[P(MTCOEt$_{0.6}$-r-MTCU$_{0.4}$)] (5k-3k) | 7900 | 1.06 | 36.3 | 0.118 | 2.8 | 110.8 | 0.114 | 10.3 ± 0.7 |
| Example 13 | MPEG1-b-[P(MTCOEt$_{0.8}$-r-MTCU$_{0.2}$)] (5k-3k) | 7500 | 1.10 | 31.8 | 0.132 | 6.3 | 196.6 | 0.153 | 8.5 ± 0.5 |
| CEx. 2 | MPEG1-b-[P(MTCOEt)] (5k-3k) | 7600 | 1.09 | 29.5 | 0.107 | 11.2 | 360.2 | 0.131 | 6.9 ± 0.5 |
| Example 14 | MPEG1-b-[P(MTCOEt$_{0.8}$-r-MTCU$_{0.2}$)] (5k-1.5k) | 6720 | 1.05 | 23.0 | 0.117 | 11.2 | 300.7 | 0.157 | 6.3 ± 0.6 |
| CEx. 3 | MPEG1-b-[P(TMC)] (5k-5k) | 10200 | 1.06 | 29.0 | 0.133 | 10.0 | 218.3 | 0.129 | 7.7 ± 0.5 |
| CEx. 4 | MPEG1-b-[P(TMC)] (5k-3k) | 8150 | 1.05 | 24.0 | 0.092 | 13.3 | 429.4 | 0.162 | 6.3 ± 0.4 |
| CEx. 5 | MPEG1-b-[P(TMC)] (5k-1.5k) | 6300 | 1.03 | 22.0 | 0.084 | 17.8 | 435.3 | 0.114 | 4.9 ± 0.4 |
| Example 16 | MPEG1-b-[P(MTCOH)$_4$-r-P(MTCU)$_5$] | | | | | | 133.0 | 0.120 | 30.2%[e] |

[a]Molecular weight was obtained from NMR.
[b]Polydispersity index by GPC in THF using PS standards.
[c]Hydrodynamic diameter and polydispersity index of aqueous solution by dynamic light scattering.
[d]Critical micelle concentration obtained by fluorescence spectroscopy.
[e]Encapsulation efficiency: 90.5% for Example 14.

Micelle Forming Ability of Examples 12, 13 and CEx. 2.

Figure 6:
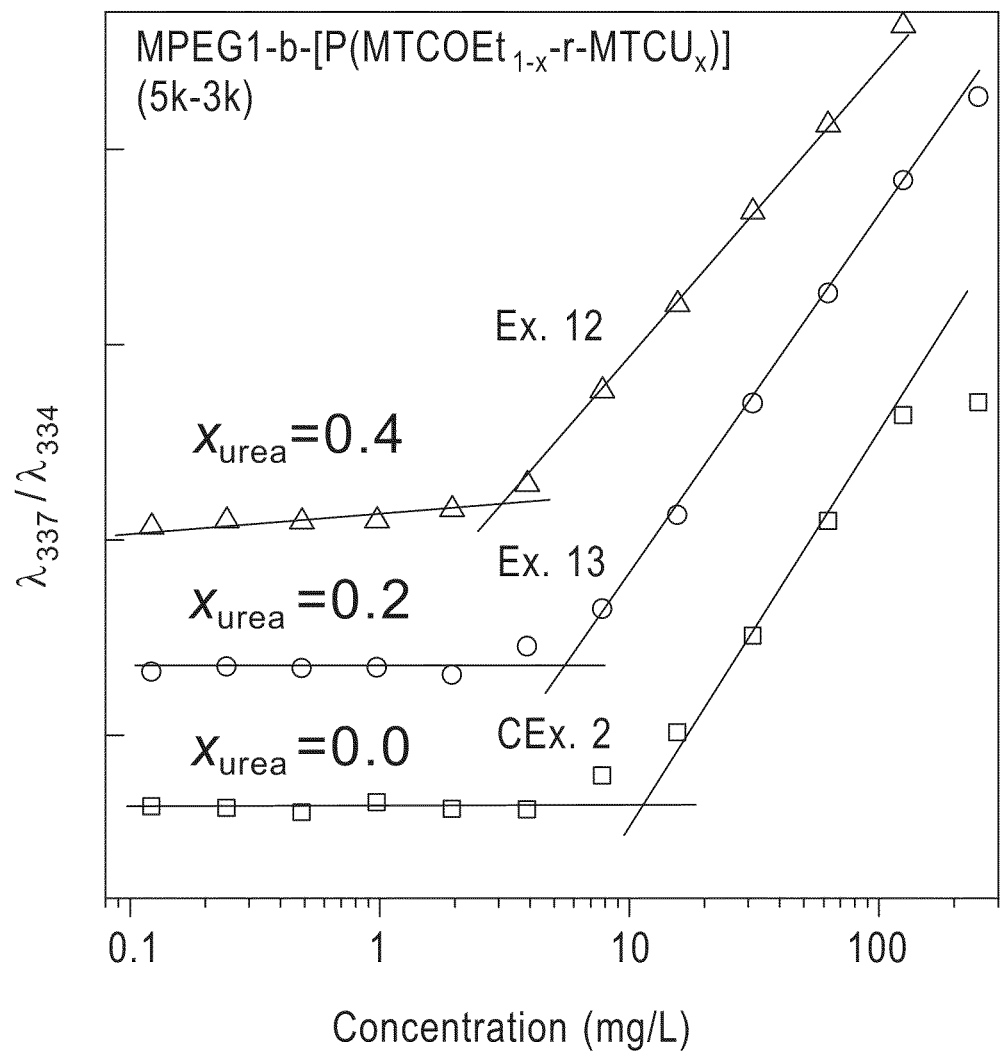
FIG. 6 is a graph comparing the dynamic light scattering results for micelles formed with Examples 12, 13 and CEx. 2.

Each of the block copolymers in Table 8, having a relatively low molecular weight hydrophobic block ($M_n$ of polycarbonate block: 1.5 k, 3 k, and 5 k), could self-disperse in water. Typically, the block copolymers were directly dispersed in deionized water and sonicated for 10 min to facilitate micelle formation and aqueous dispersion of block copolymer micelles. The effect of H-bonding urea groups on the micelle forming ability was investigated using the MPEG1-b-[P(MTCOEt$_{1-x}$-MTCU$_x$)] (5 k-3 k) block copolymers, Examples 12, 13, and CEx. 2. These polymers have mole fractions, x, of urea of 0.4, 0.2, and 0.0 respectively. FIG. 6 is a graph comparing the dynamic light scattering results for micelles formed with Examples 12, 13 and CEx. 2. MPEG1-b-[P(MTCOEt$_{1-x}$-MTCU$_x$)] (5 k-3 k) block copolymers formed nanosized micelles having an average diameter of 20 to 40 nm, and also having a narrow size distribution, from 0.084 to 0.133, as summarized in Table 8. The distinctive change accompanied by the incorporation of urea groups was observed in the critical micelle concentrations (CMC) in FIG. 6. The CMC is an important parameter, which can be used to predict the in vivo stability of a micellar drug-delivery system. The measurement of CMC values was done with steady-state fluorescence spectroscopy using pyrene as a probe. Interestingly, the CMC values for MPEG1-b-[P(MTCOEt$_{1-x}$-MTCU$_x$)] (5 k-3 k) significantly decreased with increasing the amount of pendant urea in the block copolymers, although their molecular weights were quite similar. This shows that the stabilized self-association driven by the strong H-bonding urea lowers the CMC of micelles in an aqueous environment.

Loaded Micelles of Urea Containing Block Copolymers, Examples 11 to 14.

Figure 7:
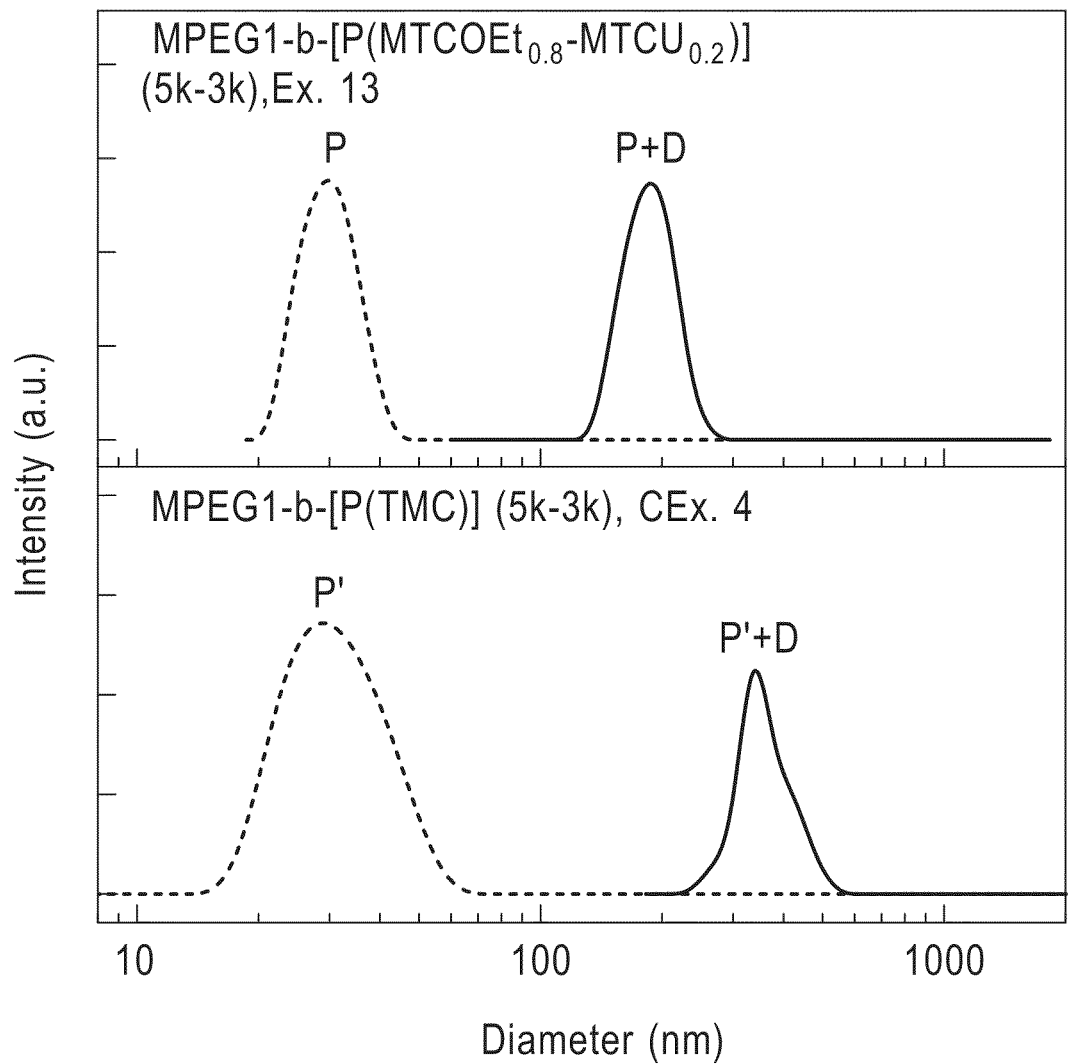
FIG. 7 is a graph showing particle sizes and size distributions for drug loaded micelles for Example 13, MPEG1-b-[P(MTCOEt$_{0.8}$-MTCU$_{0.2}$)] (5 k-3 k), (plot labeled P+D in FIG. 7) in conjunction with non-loaded polymer micelles formed with Example 13 (plot labeled P in FIG. 7). The size of non-loaded micelles prepared without urea groups, CEx. 4, MPEG1-b-[P(TMC)] (5 k-3 k), was about 24 nm in diameter (plot labeled P' in FIG. 7), while the size of drug-loaded micelles prepared from CEx. 4, MPEG1-b-[P(TMC)] (5 k-3 k), was much greater, about 430 nm (plot labeled P'+D in FIG. 7).

Urea-functional block copolymers were further used as nanocarriers for anticancer drug, doxorubicin (DOX). Block copolymer/drug hybrid micelles were prepared by a sonication-membrane dialysis technique. Typically, neutralized DOX (5 mg) with excess (3×) triethylamine in DMAC (1.5 mL) was mixed with block copolymer (10 mg) (Examples 11 to 14) dissolved in DMAC (2 mL), sonicated for 10 min in 10 mL of deionized (DI) water and then dialyzed against DI water for 2 days. The solution was filtered with 0.45 micrometer syringe filter prior to size measurement and 2-day lyophilization. FIG. 7 is a graph showing particle sizes and size distributions for drug loaded micelles for Example 13, MPEG1-b-[P(MTCOEt$_{0.8}$-MTCU$_{0.2}$)] (5 k-3 k), (plot labeled P+D in FIG. 7) in conjunction with non-loaded polymer micelles formed with Example 13 (plot labeled P in FIG. 7). The size of non-loaded micelles prepared without urea groups, CEx. 4, MPEG1-b-[P(TMC)] (5 k-3 k), was about 24 nm in diameter (plot labeled P' in FIG. 7), while the size of drug-loaded micelles prepared from CEx. 4, MPEG1-b-[P(TMC)] (5 k-3 k), was much greater, about 430 nm (plot labeled P'+D in FIG. 7). The increased size indicates that the presence of the hydrophobic drug during the micellization of CEx. 4 affects the thermodynamics and kinetics of the process, leading to larger aggregate structures. This phenomenon can be a significant drawback in drug delivery applications because the size of nanodelivery systems should ideally remain below about 200 nm in order to avoid the body defense mechanisms. As shown in FIG. 7, the drug-loaded micelles obtained from Example 13, MPEG1-b-[P(MTCOEt$_{0.8}$-MTCU$_{0.2}$)] (5 k-3 k) having a 20% urea content are below 200 nm in size and are significantly stabilized, compared to those of CEx. 4, MPEG1-b-[P(TMC)] (5 k-3 k) or CEx. 2, MPEG1-b-[P(MTCEt$_{1.0}$)] that do not contain urea.

Figure 8:
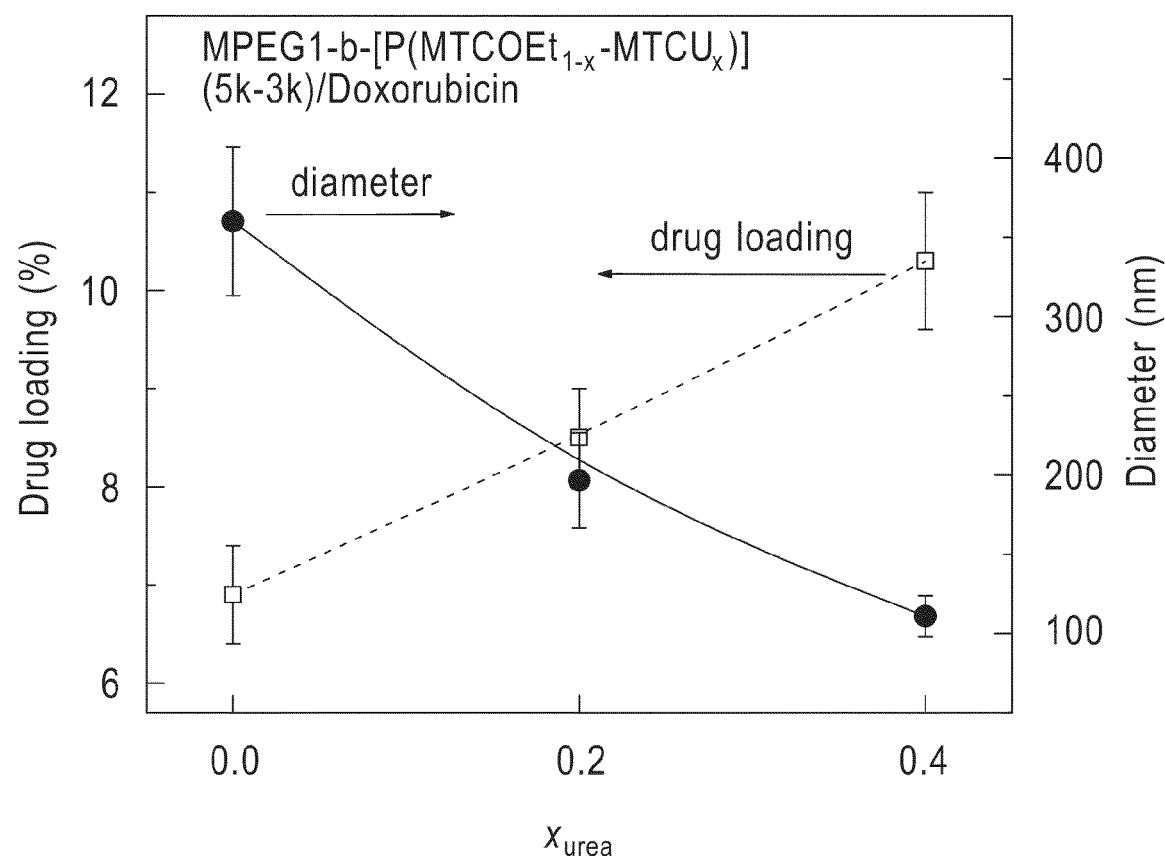
FIG. 8 is a graph showing the relationship between drug loading and size for drug-loaded micelles with MPEG1-b-[P(MTCOEt$_{1-x}$-MTCU$_x$)] block copolymers having different urea contents (Examples 12, 13, and CEx. 2, having x=0.4, 0.2, and 0.0, respectively, each having a hydrophobic block M$_n$ of 3000).

FIG. 8 is a graph showing the relationship between drug loading and size for drug-loaded micelles with MPEG1-b-[P(MTCOEt$_{1-x}$-MTCU$_x$)] block copolymers having different urea contents (Examples 12, 13, and CEx. 2, having x=0.4, 0.2, and 0.0, respectively, each having a hydrophobic block M$_n$ of 3000). The drug content in the nanoparticles was determined by freeze-drying the micelle solution and re-dissolving the mass in DMAC followed by UV-visible spectroscopy at 485 nm. As the urea content increased, the drug loading increased, from 6.3 wt % at x=0.0 to 8.5 wt % a x=0.4, while simultaneously decreasing the average particle size of drug-loaded micelles from 360 nm at x=0.0 to 110 nm at x=0.4.

Effect of Molecular Weight of Hydrophobic Block in Examples 11, 13, and 14.

Finally, the effect of molecular weights of hydrophobic blocks on drug loading and micellization behavior were further explored using copolymers with 1.5 k, 3 k, and 5 k polycarbonate blocks. Within these drug-loaded samples, micellar sizes (stability) and drug loading highly depend on the chain-lengths and characteristics of hydrophobic blocks, as summarized in Table 8. For CEx. 3, MPEG1-b-[P(TMC)] (5 k-5 k), with the largest hydrophobic block, the size of drug-loaded micelles was slightly above 200 nm. The H-bonding urea block copolymers further improve CMC of block copolymer micelles, drug loading capability, and size and size distribution of drug-loaded micelles. The differences are more pronounced in block copolymers with a relatively short hydrophobic block.

Figure 9:
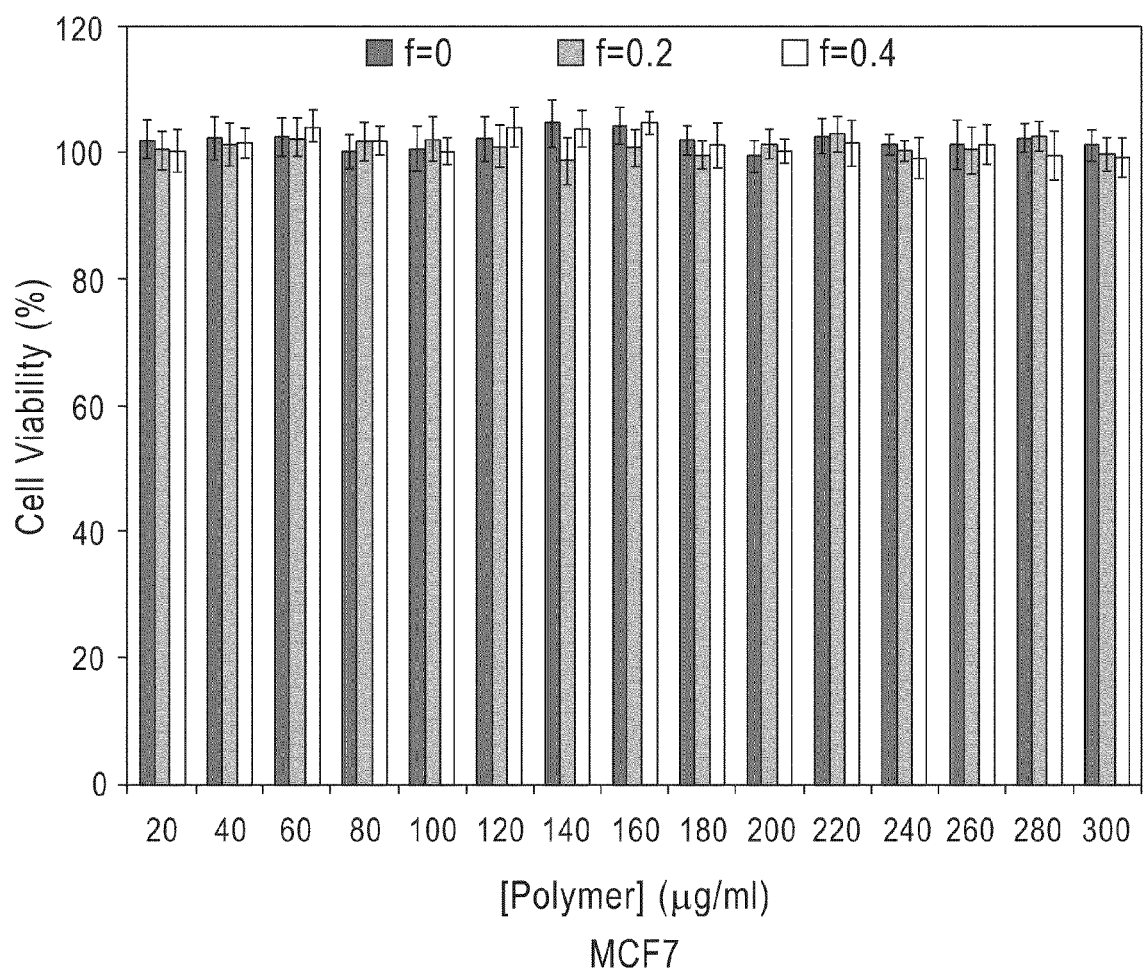
FIG. 9 is a bar chart showing the viability of MCF7 human breast cancer cells after incubation with CEx. 4 (f=0), Example 13 (f=0.2) and Example 12 (f=0.4).
Figure 10:
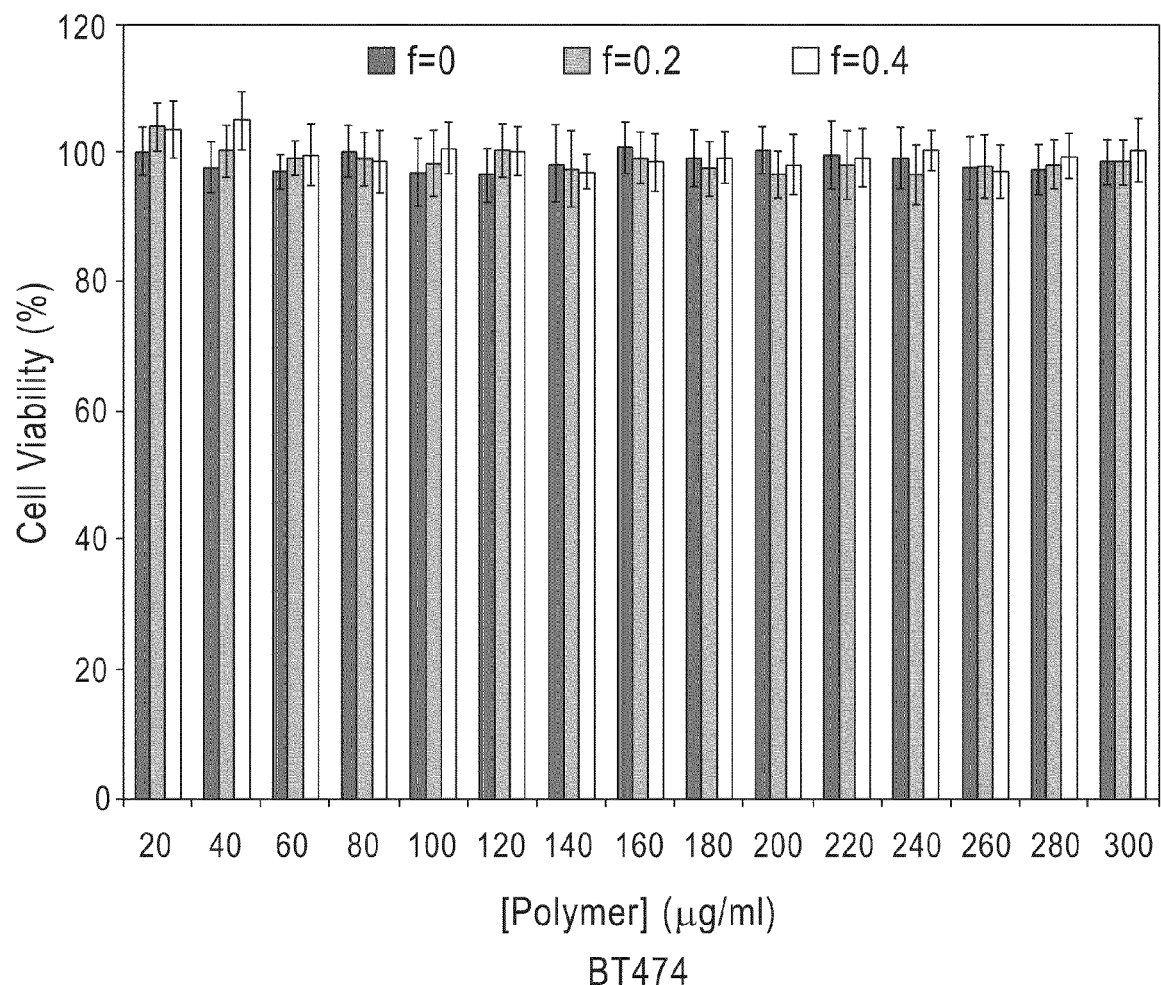
FIG. 10 is a bar chart showing the viability of BT474 human breast cancer cell lines with CEx. 4 (f=0), Example 13 (f=0.2) and Example 12 (f=0.4).

Cytotoxicity of polymers (CEx. 4, Example 13 and Example 12) was tested against MCF7 and BT474 human breast cancer cell lines. As shown in FIG. 9 and FIG. 10, none of these polymers showed significant cytotoxicity at concentrations of up to 300 mg/L.

III. Acid-Base Mixed Micelles

A mixed micelle composition was prepared comprising a two block copolymer compositions. The first block copolymer was MPEG1-b-[P(MTCOH)$_5$-b-P(MTCOEt)$_9$], Example 10. The second block copolymer was MPEG1-b-[P(MTCOEt$_{0.6}$-r-MTCU$_{0.4}$)], Example 12. The block copolymers were mixed in various urea/COOH mole ratios, as shown in Table 9.

TABLE 9

|  |  | Diameter (nm) (after DOX loading) | PDI | CMC (mg/L) | DOX loading (% in weight) |
|---|---|---|---|---|---|
| Example 10 | MPEG1-b-[P(MTCOH)$_5$-b-P(MTCOEt)$_9$] (5k-3k) | 83.1 (69.6) | (0.213) | 28.2 | 30.1 ± 1.4 |
| Example 12 | MPEG1-b-[P(MTCOEt$_{0.6}$-r-MTCU$_{0.4}$)] (5k-3k) | 58.0 (167.8) | 0.126 (0.112) | 5.6 | 10.7 ± 1.9 |
| Example 17 | Urea/COOH (molar ratio: 5/1) |  |  | 3.5 |  |
| Example 18 | Urea/COOH (molar ratio: 4/1) |  |  | 5.6 |  |
| Example 19 | Urea/COOH (molar ratio: 3/1) |  |  | 4.5 |  |
| Example 20 | Urea/COOH (molar ratio: 2/1) |  |  | 7.9 |  |
| Example 21 | Urea/COOH (molar ratio: 1/1) | 60.3 (87.6) | (0.167) | 7.9 | 25.1 ± 3.5 |
| Example 22 | Urea/COOH (molar ratio: 1/2) |  |  | 8.3 |  |
| Example 23 | Urea/COOH (molar ratio: 1/3) |  |  | 9.1 |  |
| Example 24 | Urea/COOH (molar ratio: 1/4) |  |  | 14.1 |  |
| Example 25 | Urea/COOH (molar ratio: 1/5) |  |  | 11.2 |  |

DOX was loaded into micelles through a membrane dialysis method. Briefly, neutralized Dox (5 mg) with excess (3×) triethylamine in DMAC (1.5 mL) was mixed with block copolymer (10 mg) dissolved in DMAc (0.5 mL), sonicated for 2 min in 10 mL of DI water and then dialyzed against 1000 mL of DI water for 2 days. The external water was changed at 3, 6 and 24 hours. After dialysis, the particles were collected by 2-day lyophilization. To determine DOX loading level, a known amount of freeze-dried DOX-loaded nanoparticles was dissolved in 1 mL of DMSO. The DOX concentration was estimated by using the UV-visible spectrophotometer at 480 nm. The drug loading was calculated based on the standard calibration curve obtained from DOX in DMSO.

Particle size measurement. The DOX loaded mixed micelles of Table 9 were directly dissolved in PBS buffer (pH 7.4) prior to size measurement.

The particle size of the micelles was measured through dynamic light scattering (DLS), which was performed on a Brookhaven BI-200SM goniometer system (Brookhaven, U.S.A.). The light source is a power adjustable vertically polarized 75 mW HeNe ion laser with a wavelength of 633 nm.

The particle size of the freshly prepared blank and DOX-loaded micelles was measured using dynamic light scattering (ZetaPALS, Brookhaven Instrument Corporation, USA) at a scatting angle of 90° after filtration with a 0.45 micrometer syringe filter. Each measurement was repeated 5 times. An average value was obtained from the five measurements. Multimodel analysis was chosen to conduct the size measurements to maximize the resolution as the samples might contain individual micelles and aggregates.

Critical Micelle Concentration. CMC of the blank mixed micelles of Examples 12, and Examples 17 to 25 in PBS buffer (pH 7.4) was determined using pyrene as the probe. The fluorescence spectra were recorded by a LS 50B luminescence spectrometer (Perkin Elmer, U.S.A.) at room temperatures. Samples were equilibrated for 10 min before any measurements were made. Aliquots of pyrene in acetone solution ($6.16 \times 10^{-5}$ M, 10 μL) were added to containers and the acetone was left to evaporate. Polymer solutions (1 mL) at varying concentrations were added into the containers and left to equilibrate for 24 hours. The final pyrene concentration in each sample was $6.16 \times 10^{-7}$ M. The emission spectra were scanned from 360 to 410 nm at an excitation wavelength of 339 nm while the excitation spectra were scanned from 300 to 360 nm at an emission wavelength of 395 nm. Both the excitation and emission bandwidths were set at 2.5 nm. The intensity (peak height) ratios of $I_{336}/I_{334}$ from the excitation spectra were analyzed as a function of polymer concentration. The CMC was taken from the intersection between the tangent to the curve at the inflection and tangent of the points at low concentrations.

By using this approach, mixed micelles can be formulated to reduce CMC, increase drug loading level, adjust surface density of the biological ligand, or attach two biological ligands for double targeting.

IV. Incorporation of Functional Group for Targeting

A biological functional group such as galactose can be incorporated to the other distal end of PEG through a thiol group (Scheme 3), an aldehyde group (Scheme 4), or an N-hydroxysuccinimide functionalized COOH terminal group of PEG (Scheme 5). Galactose can be used to target liver cells. Through a similar approach, other biological ligands such as peptides, proteins or antibodies can also be conjugated to polycarbonates-based block copolymers for targeting.

Scheme 3.

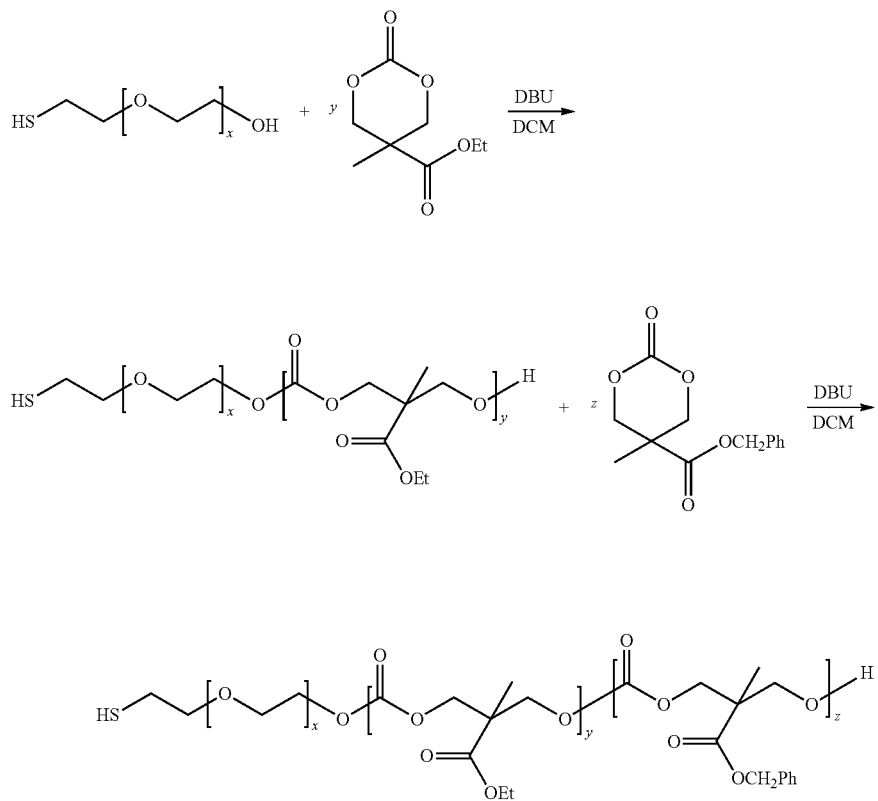

Scheme 4.
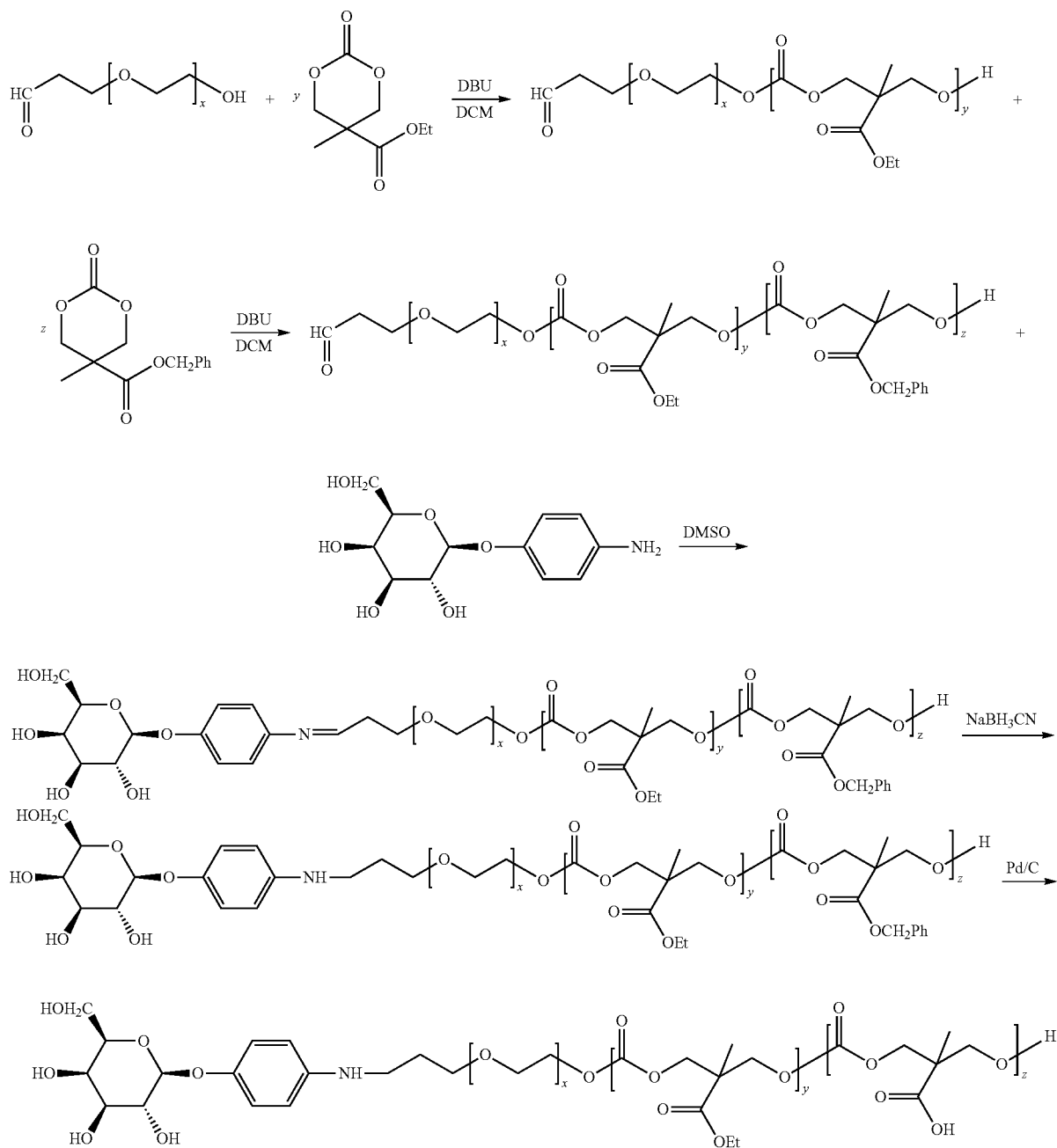
Scheme 5.
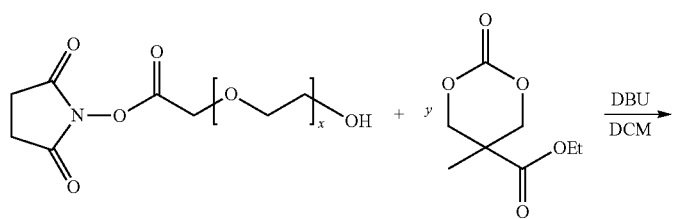

-continued

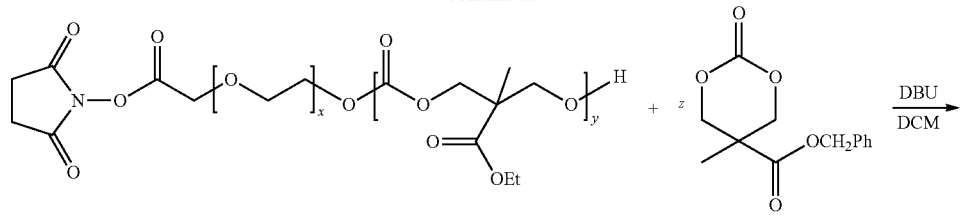

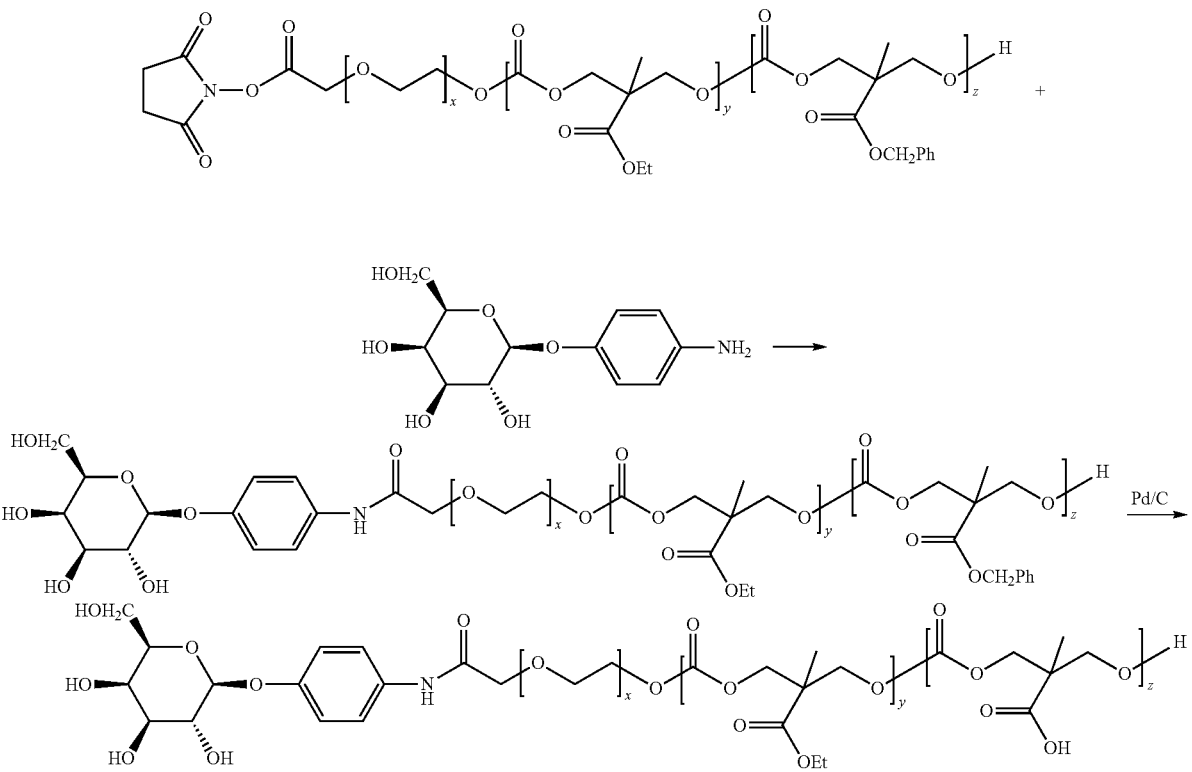

Example 26

Preparation of Thiol-Functionalized Peg-Block-Polycarbonate, HS-PEG-b-[P(MTCOEt)$_{23}$-b-P(MTC-OBn)$_{19}$]

A solution of MTCOEt (0.113 g, 0.6 mmol) in CH$_2$Cl$_2$ (0.75 mL) was added to the solution of HS-PEG-OH (0.097 g, M$_n$=3228, 0.03 mmol) and DBU (4.6 mg, 0.03 mmol) in CH$_2$Cl$_2$ (0.75 mL) under stirring. After 2 hours, a solution of MTCOBn (0.15 g, 0.6 mmol) in CH$_2$Cl$_2$ (0.75 mL) was added. The reaction was continued for another 2 hours before benzoic acid was added to quench the polymerization. The reaction mixture was then precipitated into diethyl ether (20 mL) and the precipitate was centrifuged and dried in vacuo. Finally, the crude product was purified by column chromatography on a Sephadex LH-20 column with THF as eluent, to give HS-PEG-b-[P(MTCOEt)$_{23}$-b-P(MTC-OBn)$_{19}$] as colorless viscous liquid (0.59 g, 82%). $^1$H NMR (400 MHz, CDCl$_3$, 22° C.): delta 7.3 (m, 95H, PhH), 5.15 (s, 38H, —OCH$_2$Ph), 4.25 (m, 214H, —CH$_2$OCOO and —OCH$_2$CH$_3$), 3.64 (m, 290H, H of PEG), 2.78 (d, 2H, —OCH$_2$CH$_2$SH), 2.49 (t, 2H, —OCH$_2$CH$_2$SH), 1.23 (s, 195H, —CH$_3$ and —OCH$_2$CH$_3$).

Example 27

Preparation of Aldehyde-Functionalized Peg-Block-Polycarbonate, CHO-PEG-b-[P(MTCOEt)$_{21}$-b-P(MTC-OBn)$_{20}$] (Scheme 4)

A solution of MTCOEt (0.226 g, 1.2 mmol) in CH$_2$Cl$_2$ (0.75 mL) was added to the solution of OCH-PEG-OH (0.12 g, M$_n$ 2000, 0.06 mmol) and DBU (9.2 mg, 0.06 mmol) in CH$_2$Cl$_2$ (0.75 mL) under stirring. After 2 hours, a solution of MTCOBn (0.3 g, 1.2 mmol) in CH$_2$Cl$_2$ (0.75 mL) was added. The reaction was continued for another 2 hours before benzoic acid was added to quench the polymerization. The reaction mixture was then precipitated into diethyl ether (40 mL) and the precipitate was centrifuged and dried in vacuo. Finally, the crude product was purified by column chromatography on a Sephadex LH-20 column with THF as eluent, to give OCH-PEG-b-[P(MTCOEt)$_{21}$-P(MTCOBn)$_{20}$] as colorless viscous liquid (0.52 g, 80%). $^1$H NMR (400 MHz, CDCl$_3$, 22° C.): delta 9.78 (s, 0.4H, —CHO), 7.29 (m, 100H, PhiI), 5.11 (s, 40H, —OCH$_2$Ph), 4.25 (m, 206H, —CH$_2$OCOO and —OCH$_2$CH$_3$), 3.64 (m, 179H, H of PEG), 1.23 (s, 186H, —CH$_3$ and —OCH$_2$CH$_3$).

Example 28

Synthesis of p-Aminophenyl Beta-D-Galactopyranoside Terminated PEG (APG-PEG) Polycarbonate Block Copolymer, APG-PEG-b-[P(MTCOEt)$_{21}$-P(MTCOBn)$_{20}$] (Scheme 4)

The above product OCH-PEG-b-[P(MTCOEt)$_{21}$-P(MTCOBn)$_{20}$] from Example 27 (0.52 g, 0.047 mmol) was dissolved in 10 mL of DMSO, and p-aminophenyl beta-D-galactopyranoside (APG) (0.127 g, 0.47 mmol) was added to this solution. The mixture was stirred and heated to 40° C. for 5 hours. Then, it was cooled down to ambient temperature and NaBH$_3$CN (8.9 mg, 0.141 mmol) was added to reduce the imine bond to amine. The mixture was stirred overnight, dialyzed against water (molecular weight cutoff 1,000 Daltons), and freeze-dried. Finally, APG-PEG-b-[P(MTCOEt)$_{21}$-b-P(MTC-OBn)$_{20}$] was obtained as colorless tacky liquid (0.45 g, 70%). $^1$H NMR (400 MHz, CDCl$_3$, 22° C.): delta 7.29 (m, 100H, PhiI), 5.11 (s, 40H, —OCH$_2$Ph), 4.25 (m, 206H, —CH$_2$OCOO and —OCH$_2$CH$_3$), 3.64 (m, 179H, H of PEG), 1.23 (s, 186H, —CH$_3$ and —OCH$_2$CH$_3$).

Example 29

Preparation of Galactose-Terminated Block Copolymer APG-PEG-b[P(MTCOEt)$_{21}$-b-P(MTCOH)$_{20}$] (Scheme 4)

A mixture of the above product APG-PEG-b-[P(MTCOEt)$_{21}$-b-P(MTC-OBn)$_{20}$] from Example 28 (0.45 g), THF (7.5 mL), methanol (7.5 mL), and Pd—C (10% w/w, 0.2 g) was swirled under H$_2$ (7 atm) overnight. After evacuation of the H$_2$ atmosphere, the mixture was filtered through THF-wetted Celite. Additional THF (15 mL) and methanol (15 mL) were used to ensure complete transfer. The collected washings were evaporated, and the residue was purified by column chromatography on a Sephadex LH-20 column with THF as eluent, to give galactose-terminated block copolymer, APG-PEG-b-[P(MTCOEO$_{21}$-b-P(MTC-OBn)$_{20}$] (0.35 g, 92%). %). $^1$H NMR (400 MHz, DMSO-d$_6$, 22° C.): delta 10.58 (s, 10H, —COOH), 7.33 (m, 3.9H, 2,6-PhH-NH), 6.67 (m, 3.9H, 3,5-PhH-NH), 4.13 (m, 206H, —CH$_2$OCOO and —OCH$_2$CH$_3$), 3.51 (m, 179H, H of PEG), 1.13 (s, 186H, —CH$_3$ and —OCH$_2$CH$_3$).

Example 30

Preparation of N-Hydroxysuccinimide Derivatized PEG (NHS-PEG) Block Polycarbonate Copolymer, NHS-PEG-b-[P(MTCOEt)$_{20}$-P(MTCOBn)$_{20}$] (Scheme 5)

A solution of MTCOEt (0.226 g, 1.2 mmol) in CH$_2$Cl$_2$ (0.75 mL) was added to the solution of mono N-hydroxysuccinimide derivatized PEG, NHS-PEG-OH, (0.21 g, M$_n$ 2000, 0.06 mmol) and DBU (9.2 mg, 0.06 mmol) in CH$_2$Cl$_2$ (0.75 mL) under stirring. After 2 hours, a solution of MTCOBn (0.3 g, 1.2 mmol) in CH$_2$Cl$_2$ (0.75 mL) was added. The reaction was continued for another 2 hours before benzoic acid was added to quench the polymerization. The reaction mixture was then precipitated into diethyl ether (40 mL) and the precipitate was centrifuged and dried in vacuo. Finally, the crude product was purified by column chromatography on a Sephadex LH-20 column with THF as eluent, to give NHS-PEG-b-[P(MTCOEt)$_{20}$-P(MTCOBn)$_{20}$].

Example 31

Reaction of NHS-PEG-b-[P(MTCOEt)$_{20}$-P(MTCOBn)$_{20}$] with p-aminophenyl Beta-D-Galactopyranoside (APG) APG2-PEG-b-[P(MTCOEt)$_{20}$-P(MTCOBn)$_{20}$] (Scheme 5)

First, 10 excess mol of p-aminophenyl beta-D-galactopyranoside (APG) (0.50 mmol) to NHS-PEG-b-[P(MTCOEt)$_{20}$-P(MTCOBn)$_{20}$] (0.05 mmol) was dissolved in 1 ml of anhydrous N,N-dimethylformamide (DMF). Then, this solution was added to 0.05 mmol of NHS-PEG-b-[P(MTCOEt)$_{20}$-P(MTCOBn)$_{20}$] from Example 30 dissolved in 1.5 ml of anhydrous DMF. The reaction mixture was gently stirred for 6 hours at room temperature under nitrogen. The product galactose-terminated APG2-PEG-b-[P(MTCOEt)$_{20}$-P(MTCOBn)$_{20}$] was purified by dialysis against DMSO and distilled water (dialysis tubing with MWCO 1000 Da) and freeze-dried.

Example 32

Preparation of Galactose-Terminated APG2-PEG-b-[P(MTCOEt)$_{20}$-P(MTCOH)$_{20}$] (Scheme 5)

A mixture of the above product, APG2-PEG-b-[P(MTCOEt)$_{20}$-P(MTCOBn)$_{20}$] from Example 31, THF (7.5 mL), methanol (7.5 mL), and Pd—C (10% w/w, 0.2 g) was swirled under H$_2$ (7 atm) overnight. After evacuation of the H$_2$ atmosphere, the mixture was filtered through THF-wetted Celite. Additional THF (15 mL) and methanol (15 mL) were used to ensure complete transfer. The collected washings were evaporated, and the residue was purified by column chromatography on a Sephadex LH-20 column with THF as eluent, to give galactose-terminated APG2-PEG-b-[P(MTCOEt)$_{20}$-P(MTCOH)$_{20}$].

Summarizing, a series of block copolymers comprising monomethyl endcapped PEG and functional polycarbonate have been demonstrated to be highly efficient carriers for DOX delivery. The block copolymers have low CMC values and their micelles in water exhibited small particle size. The variance in CMC and particle size could be attributed to the different pendant functional group distribution in the polycarbonate segment of block copolymers. The polymers comprising urea and/or carboxylic acid containing pendant groups in the hydrophobic block achieve high DOX loading levels. Fast DOX release was achieved at 37° C. within 7 hours without significant initial burst, and the DOX released varied from 42% to 80% depending on the pendant functional groups distribution in the polycarbonate segment. Additionally, compared with non-toxic blank block copolymers, the DOX-loaded micelles showed almost the same cytotoxicity as free DOX against HepG2 cells. The block copolymers can be further tailored in terms of backbone structure, pendant functional groups, and distribution (random versus block copolymerization) to efficiently incorporate other types of drugs having different molecular structures and physicochemical properties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A biodegradable block copolymer, comprising:
a hydrophilic block comprising a polyether backbone linked to a hydrophobic block, the hydrophobic block comprising a first repeat unit, the first repeat unit comprising i) a first backbone functional group selected from the group consisting of ester, carbonate, carbamate, urea, thiocarbamate, thiocarbonate, and dithiocarbonate, and ii) a first side chain, the first side chain comprising a functional group selected from the group consisting of a) urea groups and b) mixtures of urea groups and carboxylic acid groups; wherein no side chain of the hydrophobic block comprises a covalently bound biologically active material selected from the group consisting of genes, nucleotides, proteins, peptides, drugs, and combinations thereof, and the block copolymer self-assembles in water forming micelles suitable for sequestering a biologically active material selected from the group consisting of genes, nucleotides, proteins, peptides, drugs, and combinations thereof by a non-covalent interaction.

2. The block copolymer of claim 1, wherein the block copolymer is 60% biodegraded within 180 days in accordance with ASTM D6400.

3. The block copolymer of claim 1, wherein the hydrophilic block comprises an end unit comprising a galactose moiety and/or a mannose moiety.

4. The block copolymer of claim 3, wherein the end unit comprises a galactose moiety having the structure:

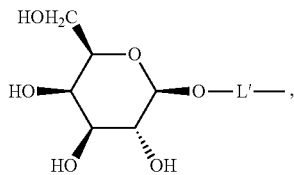

wherein -L'- is a divalent linking group comprising 2 to 50 carbons.

5. An aqueous micelle comprising the biodegradable first block copolymer of claim 1.

6. The micelle of claim 5, wherein the micelle is a loaded micelle comprising 5 wt. % to 50 wt. % of a non-covalently bound biologically active material selected from the group consisting of genes, nucleotides, proteins, peptides, drugs, and combinations thereof based on total dry weight of the loaded micelle.

7. The micelle of claim 5, further comprising a biodegradable second block copolymer, wherein the second block copolymer comprises a hydrophilic block comprising a polyether backbone linked to a hydrophobic block, the hydrophobic block comprising a repeat unit, the repeat unit comprising i) a backbone functional group selected from the group consisting of ester, carbonate, carbamate, urea, thiocarbamate, thiocarbonate, and dithiocarbonate, and ii) a side chain comprising a carboxylic acid group; wherein no side chain of the hydrophobic block of the second block copolymer comprises a covalently bound biologically active material selected from the group consisting of genes, nucleotides, proteins, peptides, drugs, and combinations thereof.

8. The micelle of claim 7, wherein the second block copolymer is 60% biodegraded within 180 days in accordance with ASTM D6400.

9. A method of treating a cell, comprising contacting a cell with an aqueous mixture comprising nanoparticles of the loaded micelle of claim 6.

10. A biodegradable block copolymer, comprising:
a hydrophilic block derived from a polyether alcohol; and
a hydrophobic block comprising a first repeat unit derived by ring opening polymerization of a first cyclic carbonyl monomer initiated by the polyether alcohol, the first repeat unit comprising a side chain moiety comprising a functional group selected from the group consisting of i) urea groups and ii) mixtures of urea groups and carboxylic acid groups;
wherein no side chain of the hydrophobic block comprises a covalently bound biologically active material selected from the group consisting of genes, nucleotides, proteins, peptides, drugs, and combinations thereof, and the block copolymer self-assembles in water, forming micelles suitable for sequestering a biologically active material selected from the group consisting of genes, nucleotides, proteins, peptides, drugs, and combinations thereof by a non-covalent interaction, and wherein the block copolymer is 60% biodegraded within 180 days in accordance with ASTM D6400.

11. The block copolymer of claim 10, wherein the hydrophobic block comprises a backbone selected from the group consisting of polyesters, polycarbonates, and combinations thereof.

12. The block copolymer of claim 10, wherein the hydrophobic block comprises a homopolymer of the first repeat unit.

13. The block copolymer of claim 10, wherein the hydrophobic block comprises a second repeat unit derived from a second cyclic carbonyl monomer by ring opening polymerization, wherein the first repeat unit comprises a urea group and the second repeat unit comprises a carboxylic acid group.

14. The block copolymer of claim 13, wherein the hydrophobic block comprises a random copolymer chain derived by ring opening polymerization of a mixture comprising the first cyclic carbonyl monomer and the second cyclic carbonyl monomer.

15. The block copolymer of claim 13, wherein the hydrophobic block is derived by sequential ring opening polymerization of the first cyclic carbonyl monomer followed by the second cyclic carbonyl monomer.

16. The block copolymer of claim 15, wherein the hydrophobic block is derived by sequential ring opening polymerization of the second cyclic carbonyl monomer followed by the first cyclic carbonyl monomer.

17. The block copolymer of claim 10, wherein the polyether alcohol is a mono end-derivatized poly(alkylene glycol) of the formula (3):

$$Z'—[CH_2(CHR^5)_xCHR^5O]_n—H \quad (3)$$

wherein x is 0 to 8, each $R^5$ is a monovalent radical independently selected from the group consisting of hydrogen, alkyl groups comprising 1 to 30 carbons, and aryl groups comprising 6 to 30 carbons; subscript n is an integer from 2 to 10000; and Z' is a monovalent radical comprising 2 to 100 carbons, and includes an end repeat unit of the poly(alkylene glycol).

18. The block copolymer of claim 10, wherein the hydrophilic block comprises a derivatized end unit comprising a galactose moiety and/or a mannose moiety.

19. The block copolymer of claim 18, wherein the derivatized end unit comprises a galactose moiety having the structure

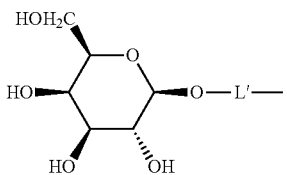

wherein -L'- is a divalent linking group comprising 2 to 50 carbons containing the end unit of the hydrophilic block.

20. The block copolymer of claim 10, wherein the hydrophobic block is endcapped as an ester comprising 2 to 100 carbons.

21. The block copolymer of claim 10, wherein the block copolymer is amphiphilic and self-assembles in water to form nanoparticles having an average particle size of from 10 nm to 500 nm at a pH of from 5.0 to 8.0.

22. The block polymer of claim 10, wherein the first cyclic carbonyl compound is a compound of formula (5):

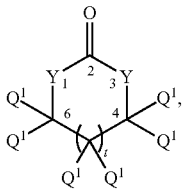

(5)

wherein:
t is an integer from 0 to 6;
each Y is a divalent radical independently selected from the group consisting of

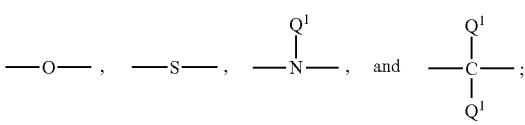

and
each $Q^1$ is a monovalent radical independently selected from the group consisting of hydrogen, halides, alkyl groups comprising 1 to 30 carbons, aryl groups comprising 6 to 30 carbon atoms, and groups having the structure

wherein $M^1$ is a monovalent radical selected from the group consisting of $—R^1$, $—OR^1$, $—NHR^1$, $—NR^1R^1$, and $—SR^1$, wherein each $R^1$ is a monovalent radical independently selected from the group consisting of alkyl groups comprising 1 to 30 carbons, and aryl groups comprising 6 to 30 carbons; and
one or more $Q^1$ groups comprises a functional group selected from the group consisting of i) urea groups and ii) mixtures of urea groups and carboxylic acid groups.

23. The block copolymer of claim 10, wherein the first cyclic carbonyl compound is a compound of formula (6):

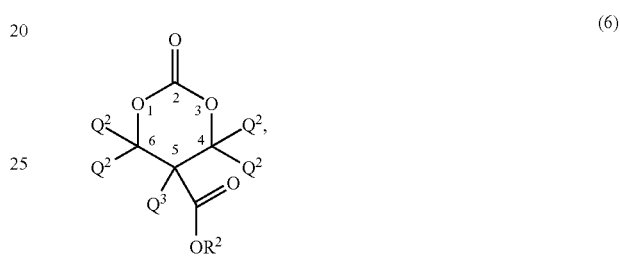

(6)

wherein
each $Q^2$ is a monovalent radical independently selected from the group consisting of hydrogen, halides, alkyl groups comprising 1 to 30 carbons, aryl groups comprising 6 to 30 carbon atoms, and groups having the structure

wherein $M^1$ is a monovalent radical selected from the group consisting of $—R^1$, $—OR^1$, $—NHR^1$, $—NR^1R^1$, or $—SR^1$, and each $R^1$ is a monovalent radical independently selected from the group consisting of an alkyl groups comprising 1 to 30 carbons, and aryl groups comprising 6 to 30 carbons;
$R^2$ is a monovalent radical independently selected from the group consisting of alkyl groups comprising 1 to 30 carbons, and aryl groups comprising 6 to 30 carbons;
$Q^3$ is a monovalent radical selected from the group consisting of hydrogen, alkyl groups having 1 to 30 carbons, and aryl groups having 6 to 30 carbons; and
one or more $Q^2$, $Q^3$ and/or $R^2$ groups comprises a functional group selected from the group consisting of i) urea groups and ii) mixtures of urea groups and carboxylic acid groups.

24. The block copolymer of claim 10, wherein the first cyclic carbonyl compound is a compound of formula (7):

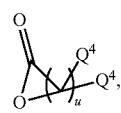

(7)

wherein
u is an integer from 1 to 8;
each $Q^4$ is a monovalent radical independently selected from the group consisting of hydrogen, halides, carboxy groups, alkyl groups comprising 1 to 30 carbons, aryl groups comprising 6 to 30 carbon atoms, and groups having the structure

, wherein $M^1$ is a monovalent radical selected from the group consisting of $-R^1$, $-OR^1$, $-NHR^1$, $-NR^1R^1$, and $-SR^1$, wherein each $R^1$ is a monovalent radical independently selected from the group consisting of alkyl groups comprising 1 to 30 carbons, and aryl groups comprising 6 to 30 carbons;
optionally, a

group independently represents a divalent radical selected from the group consisting of $-O-$, $-S-$, $-NHR^1$, or $-NR^1R^1$;
optionally, when u is 2 or more, a

group independently represents a

group; and
wherein one or more $Q^4$ groups comprises a functional group selected from the group consisting of i) urea groups and ii) mixtures of urea groups and carboxylic acid groups.

25. The block copolymer of claim 10, wherein the first cyclic carbonyl compound is a compound of formula (8):

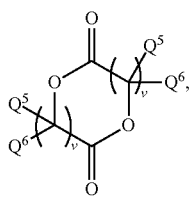

(8)

wherein
each $Q^5$ is a monovalent radical independently selected from the group consisting of hydrogen, halides, alkyl groups comprising 1 to 30 carbons, aryl groups comprising 6 to 30 carbon atoms, and groups having the structure

, where $M^1$ is a monovalent radical selected from the group consisting of $-R^1$, $-OR^1$, $-NHR^1$, $-NR^1R^1$, and $-SR^1$, wherein each $R^1$ is a monovalent radical independently selected from the group consisting of alkyl groups comprising 1 to 30 carbons, and aryl groups comprising 6 to 30 carbons;
each $Q^6$ is a monovalent group independently selected from the group consisting of hydrogen, alkyl groups having 1 to 30 carbons, and aryl groups having 6 to 30 carbons;
each v independently represents an integer from 1 to 6; and
wherein one or more $Q^5$ and/or a $Q^6$ group comprises a functional group selected from the group consisting of i) urea groups and ii) mixtures of urea groups and carboxylic acid groups.

26. The block copolymer of claim 10, wherein the first cyclic carbonyl monomer is

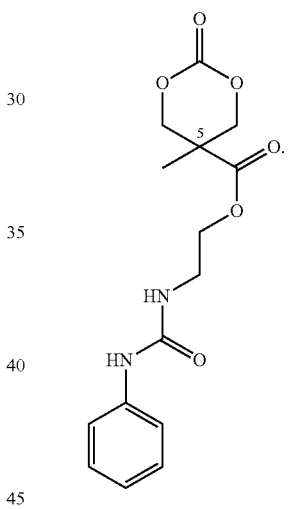

27. A method of forming a biodegradable block copolymer, the method comprising:
forming a block copolymer by ring opening polymerization of a first cyclic carbonyl monomer initiated by a polyether alcohol, wherein the block copolymer comprises a hydrophilic and a hydrophobic block, the hydrophilic block derived from the polyether alcohol, and the hydrophobic block comprising a first repeat unit comprising a side chain comprising a functional group selected from the group consisting of i) urea groups and ii) mixtures of urea groups and carboxylic acid groups;
wherein the hydrophobic block comprises no side chain comprising a covalently bound biologically active material selected from the group consisting of genes, nucleotides, proteins, peptides, drugs, and combinations thereof, the block copolymer forms micelles in water suitable for sequestering a biologically active material selected from the group consisting of genes, nucleotides, proteins, peptides, drugs, and combinations thereof by a non-covalent interaction, and the block copolymer is 60% biodegraded within 180 days in accordance with ASTM D6400.

28. The method of claim 27, further comprising derivatizing the end unit of the hydrophilic block, wherein the derivatized end unit comprises a galactose and/or a mannose moiety capable of interacting with a specific cell typo.

29. The method of claim 28, wherein the derivatized end unit comprises a galactose moiety for interacting with liver cells.

30. The method of claim 28, further comprising converting any side chain latent carboxylic acid of the hydrophobic block to a carboxylic acid.

31. The method of claim 27, wherein the ring opening polymerization is catalyzed by an organocatalyst.

32. A micelle, comprising:
a biodegradable first block copolymer, the first block copolymer comprising a hydrophilic block derived from a polyether alcohol; and a hydrophobic block comprising a first repeat unit derived by ring opening polymerization of a first cyclic carbonyl monomer initiated by the polyether alcohol, the first repeat unit comprising a side chain comprising a functional group selected from the group consisting of i) urea groups and ii) mixtures of urea groups and carboxylic acid groups; wherein no side chain of the hydrophobic block comprises a covalently bound biologically active material selected from the group consisting of genes, nucleotides, proteins, peptides, drugs, and combinations thereof, the block copolymer is suitable for sequestering a biologically active material selected from the group consisting of genes, nucleotides, proteins, peptides, drugs, and combinations thereof by a non-covalent interaction, and the block copolymer is 60% biodegraded within 180 days in accordance with ASTM D6400.

33. The micelle of claim 32, wherein the micelle has an average particle size of from 10 nm to 250 nm in aqueous solution at a pH of from 5.0 to 8.0.

34. The micelle of claim 32, wherein the first block copolymer has a critical micelle concentration of 0.01 to 300 mg/L.

35. The micelle of claim 32, wherein the hydrophilic block comprises a derivatized end unit comprising a galactose moiety and/or a mannose moiety.

36. The micelle of claim 32, wherein the micelle has a cytotoxicity of from 0% to 15%.

37. The micelle of claim 32, wherein the hydrophobic block comprises a side chain urea group.

38. The micelle of claim 32, wherein the hydrophobic block is derived by ring opening polymerization of

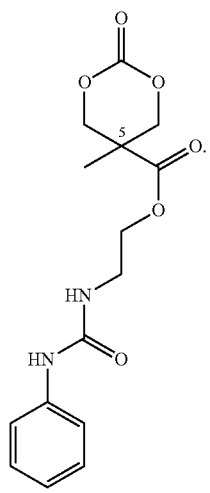 [SMILES: CC1(C(=O)OCCNC(=O)Nc2ccccc2)COC(=O)OC1]

39. The micelle of claim 32, wherein the micelle is a loaded micelle comprising 5 wt. % to 50 wt. % of a non-covalently bound biologically active material selected from the group consisting of genes, nucleotides, proteins, peptides, drugs, and combinations thereof based on total dry weight of the loaded micelle.

40. The micelle of claim 32, further comprising a biodegradable second block copolymer, wherein the second block copolymer comprises a second hydrophilic block derived from a second polyether alcohol, and a second hydrophobic block derived by ring opening polymerization of a second cyclic carbonyl monomer initiated by the second polyether alcohol; wherein no side chain of the second hydrophobic block comprises a covalently bound biologically active material selected from the group consisting of genes, nucleotides, proteins, peptides, drugs, and combinations thereof, the second block copolymer comprises a second hydrophobic block comprising a side chain carboxylic acid group, and the second block copolymer is 60% biodegraded within 180 days in accordance with ASTM D6400.

41. A method of treating a cell, comprising:
contacting a cell with an aqueous mixture comprising nanoparticles of a loaded micelle, the loaded micelle comprising:
a biodegradable first block copolymer, the first block copolymer comprising a hydrophilic block derived from a polyether alcohol, and a hydrophobic block comprising a first repeat unit derived by ring opening polymerization of a first cyclic carbonyl monomer initiated by the polyether alcohol, wherein the first repeat unit comprises a side chain comprising a functional group selected from the group consisting of i) urea groups and ii) mixtures of urea groups and carboxylic acid groups; and
a biologically active material selected from the group consisting of genes, nucleotides, proteins, peptides, drugs, and combinations thereof;
wherein the first block copolymer is suitable for sequestering the biologically active material by a non-covalent interaction, no side chain of the hydrophobic block is covalently bound to the biologically active material, and the first block copolymer is 60% biodegraded within 180 days in accordance with ASTM D6400.

42. The method of claim 41, wherein the biologically active material is a drug.

43. The method of claim 41, wherein said contacting is in vitro, ex vivo, or in vivo.

44. The method of claim 41, wherein the loaded micelles have a cytotoxicity of from 0% to 20%.

* * * * *